US010406120B2

(12) United States Patent
Liu et al.

(10) Patent No.: US 10,406,120 B2
(45) Date of Patent: Sep. 10, 2019

(54) METHODS AND COMPOSITIONS FOR TREATING KIDNEY DISORDERS

(71) Applicant: Golden Biotechnology Corporation, Jersey City, NJ (US)

(72) Inventors: Sheng-Yung Liu, New Taipei (TW); San-Bao Hwang, Iowa City, IA (US)

(73) Assignee: Golden Biotechnology Corporation, Jersey City, NJ (US)

( * ) Notice: Subject to any disclaimer, the term of this patent is extended or adjusted under 35 U.S.C. 154(b) by 0 days.

(21) Appl. No.: 15/058,341

(22) Filed: Mar. 2, 2016

(65) Prior Publication Data

US 2016/0184239 A1   Jun. 30, 2016

Related U.S. Application Data

(63) Continuation of application No. 13/980,791, filed on Oct. 2, 2013, now abandoned.

(51) Int. Cl.
*A61K 31/122* (2006.01)
*A61K 31/015* (2006.01)
*A61K 36/07* (2006.01)

(52) U.S. Cl.
CPC .......... *A61K 31/122* (2013.01); *A61K 31/015* (2013.01); *A61K 36/07* (2013.01)

(58) Field of Classification Search
CPC ..... A61K 31/122; A61K 31/015; A61K 36/07
USPC ........................................ 514/311, 688, 690
See application file for complete search history.

(56) References Cited

U.S. PATENT DOCUMENTS

| 7,342,137 | B1 | 3/2008 | Liu et al. |
| 7,385,088 | B1 | 6/2008 | Liu et al. |
| 7,501,454 | B2 * | 3/2009 | Liu .................. C07C 403/02 514/690 |
| 2008/0312334 | A1 | 12/2008 | Liu et al. |
| 2008/0312335 | A1 | 12/2008 | Liu et al. |
| 2008/0312474 | A1 | 12/2008 | Liu et al. |

FOREIGN PATENT DOCUMENTS

| EP | 2221291 A1 | 8/2010 |
| EP | 2233463 A1 | 9/2010 |
| JP | 2009-019020 A | 1/2009 |
| TW | 201034657 A | 10/2010 |

OTHER PUBLICATIONS

Pei-Yi Tsai, et al., "Antroquinonol reduces oxidative stress by enhancing the Nrf2 signaling pathway and inhibits inflammation and sclerosis in focal segmental glomerulosclerosis mice," Free Radical Biology and Medicine, vol. 50, No. 11, Mar. 2, 2011, pp. 1503-1516.

Jia-Ming Chang, et al., "An Extract of Antrodia camphorate Mycelia Attenuates the Progression of Nephritis in Systemic Lupus Erythematosus-Prone NZB/W F1 Mice," Evidence Based Complementary and Alternative Medicine, eCAM published Sep. 2, 2008.
You-Cheng Hseu, et al., Antrodia camphorate suppresses lipopolysaccharide-induced nuclear factor-kB activation in transgenic mice evaluated by bioluminescence imaging, Food and Chemical Toxicology 48 (8-9), pp. 2319-2325, Aug. 1, 2010.
Sien-Sing Yang, et al., "New Constituents with iNOS Inhibitory Activity from Mycelium of Androdia camphorata," Plant Med., 75, pp. 512-516, Feb. 2, 2009.
Chang, Jia-Ming et al., "The Anti-hepatitis B Virus of Boehmeria nivea Extract in HB-viremia SCID Mice," Evidence Based Complementary Alternative Medicine, vol. 7 Issue 2: pp. 189-195, Jan. 2008.
Chao, T-K et al., "The endogenous immune response modulates the course of IgA-immune complex mediated nephropathy," Kidney International, vol. 70 Issue 2: pp. 283-297, Jul. 2006.
Chen, Hung-Chun et al., "Oxidative Metabolism of Polymorphonuclear Leukocytes (PMN) in Patients With IgA Nephropathy," Journal of Clinical Laboratory Analysis vol. 6 Issue 1: pp. 35-39, 1992.
Lee, Tzong-Hui et al., "A New Cytotoxic Agent from Solid-State Fermented Mycelium of Antrodia camphorata," Planta Med, vol. 73 Issue 13: pp. 1412-1415, Sep. 2007. Georg Thieme Verlag KG Stuttgart. New York.
Shui, Hao-Ai et al., "Osteopontin as an injury marker expressing in epithelial hyperplasia lesions helpful in prognosis of focal segmental glomerulosclerosis," Translational Research, vol. 150 Issue 4: pp. 216-222, Oct. 2007.
Shui, Hao-Ai et al., "Fibronectin in blood invokes the development of focal segmental glomerulosclerosis in mouse model," Nephrology Dialysis Transplantation, vol. 21 Issue 7: pp. 1794-1802, Mar. 2006. Oxford University Press on behalf of ERA-EDTA.
Ka, Shuk-Man et al., "Glomerular crescent-related biomarkers in a murine model of chronic graft versus host disease," Nephrology Dialysis Transplantation, vol. 21 Issue 2: pp. 288-298, Feb. 2006. Oxford University Press on behalf of ERA-EDTA.
Wu, Chia-Chao et al., "H0-1 induction ameliorates experimental murine membranous nephropathy : anti-oxidative, anti-apoptotic and immunomodulatory effects," Nephrology Dialysis Transplantation, vol. 23 Issue 10: pp. 3082-3090, Oct. 2008.
Ka, Shuk-Man et al., "Decoy Receptor 3 Ameliorates an Autoimmune Crescentic Glomerulonephritis Model in Mice," Journal of the American Society of Nephrology, vol. 18 Issue 9: pp. 2473-2485, Sep. 2007.
Wu, C-C et al., "Melatonin prevents endotoxin-induced circulatory failure in rats," Journal of Pineal Research, vol. 30 Issue 3: pp. 147-156, Sep. 2001. Munksgaard. Copenhagen.
Kretzler, Matthias et al., "Podocyte damage is a critical step in the development of glomerulosclerosis in the uninephrectomised-desoxycorticosterone hypertensive rat," Virchows Archiv An International Journal of Pathology, vol. 425 Issue 2: pp. 181193, Sep. 1994. Springer International. Berlin, Germany.

(Continued)

*Primary Examiner* — Pancham Bakshi
(74) *Attorney, Agent, or Firm* — Chang-Hsing Liang

(57) ABSTRACT

The present invention provides methods for treating glomerulosclerosis such as focal segmental glomerulosclerosis (FSGS) or glomerulonephritis such as immunoglobulin A nephropathy (IgAN) by cyclohexenone compounds.

11 Claims, 37 Drawing Sheets

(56) References Cited

OTHER PUBLICATIONS

Lai, Kar Neng, "Future Directions in the Treatment of IgA Nephropathy," Nephron, vol. 92 Issue 2: pp. 263-270, Oct. 2002. S. Karger Ag. Basel.

Lai, Kar Neng et al., "Heat-Aggregated IgA Prepared from Patients with IgA Nephropathy Increases Priming of Human Neutrophils to Produce Inositol Triphosphate following Fmet-Leu-Phe Stimulation in vitro," Nephron, vol. 69 Issue 1: pp. 1-8, Jan. 1995. S. Karger Ag. Basel.

Kashem, Abul et al., "Fcα R expression on polymorphonuclear leukocyte and superoxide generation in IgA nephropathy," Kidney International, vol. 45 Issue 3: pp. 868-875, Mar. 1994.

Falk, Michael C. et al., "Infiltration of the kidney by αl3 and 78T cells: Effect on progression in IgA nephropathy," Kidney International, vol. 47: pp. 177-185 Jan. 1995.

Van Es, La et al., "GMP-17-positive T-lymphocytes in renal tubules predict progression in early stages of IgA nephropathy," Kidney International, vol. 73 Issue 12: pp. 1426-1433, Jun. 2008.

Torres, DD et al., "The ratio of epidermal growth factor to monocyte chemotactic peptide-1 in the urine predicts renal prognosis in IgA nephropathy," Kidney International, vol. 73 Issue 3: pp. 327-333, Feb. 2008.

Walsh, Michael et al., "Histopathologic Features Aid in Predicting Risk for Progression of IgA Nephropathy," Clinical Journal of the American Society of Nephrology, vol. 5 Issue 3: pp. 425-430 Mar. 2010.

\* cited by examiner

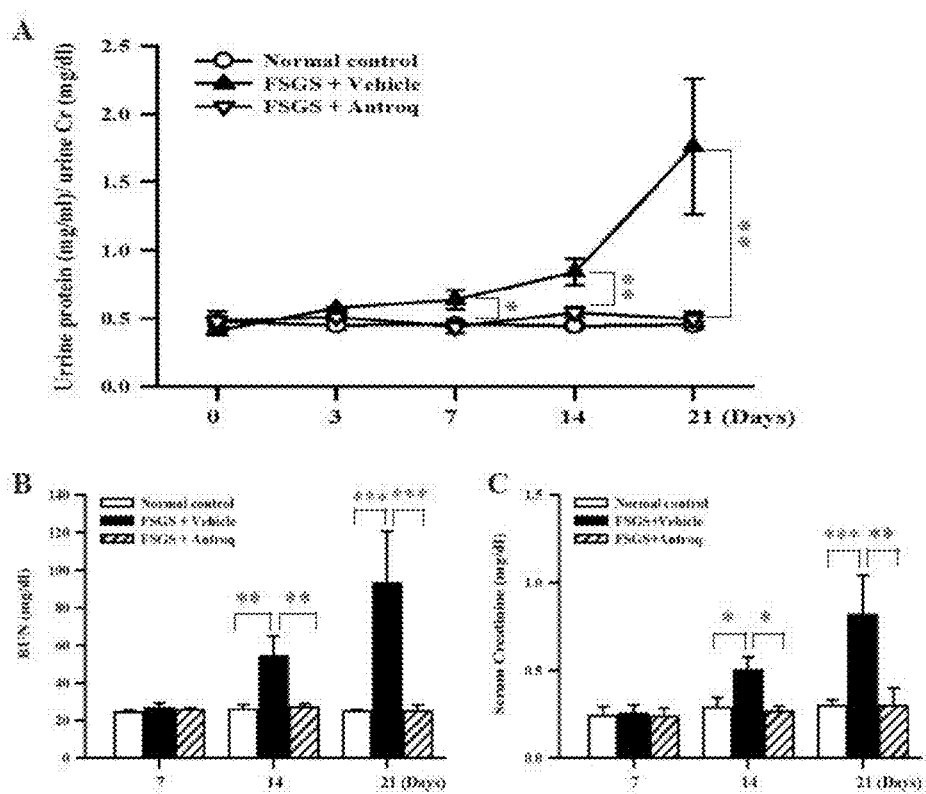
FIG. 1A-C

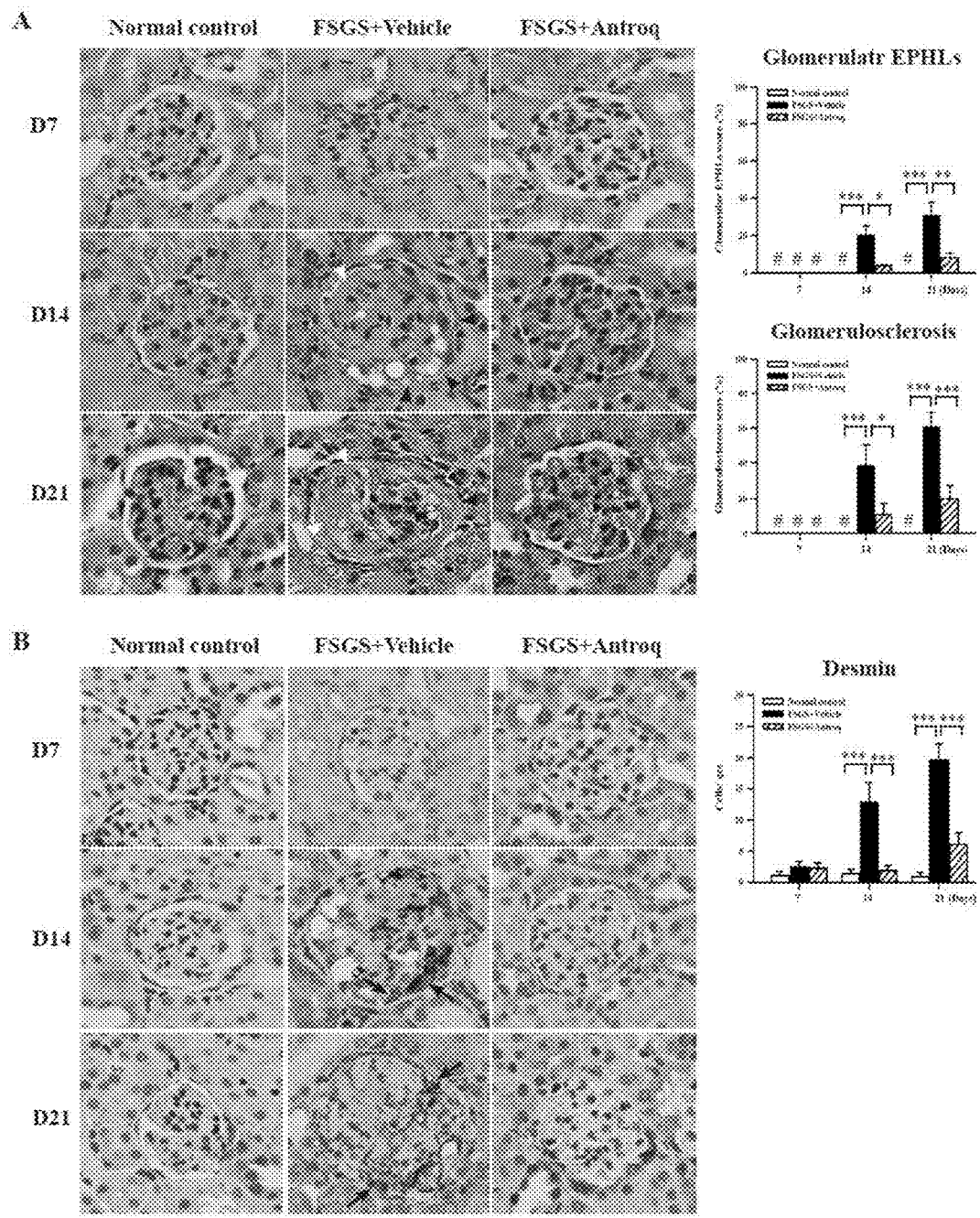
FIG. 2A-B

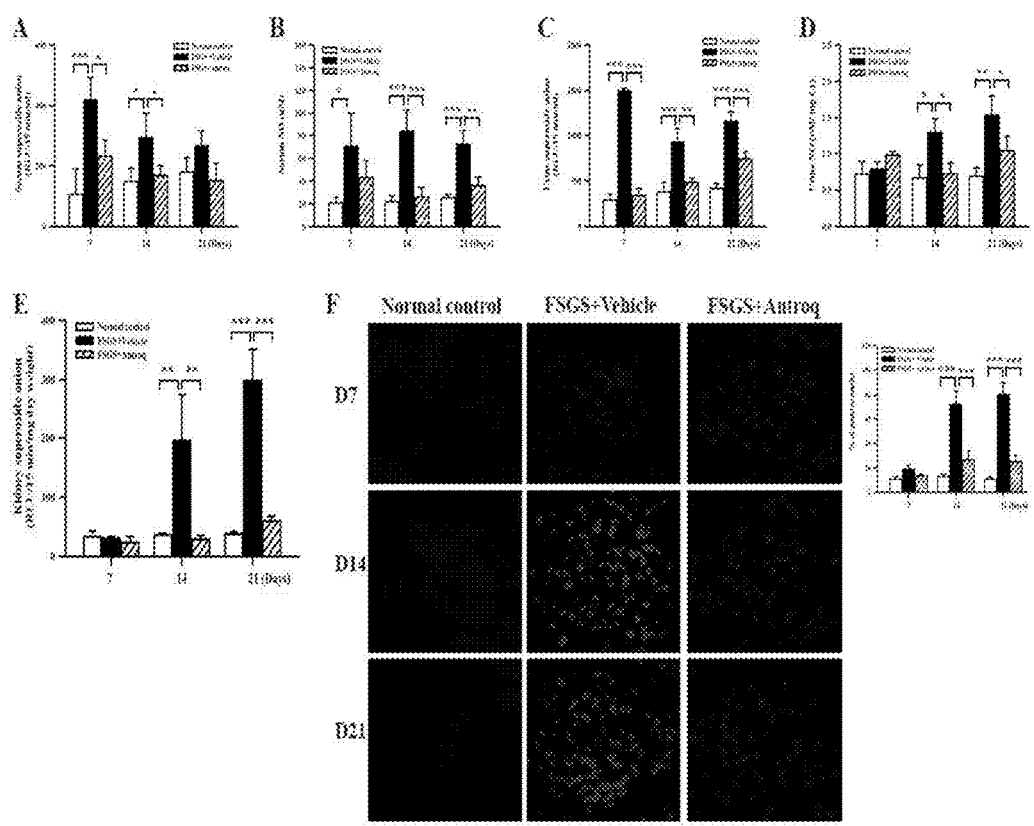
FIG. 3A-F

FIG. 4A-E
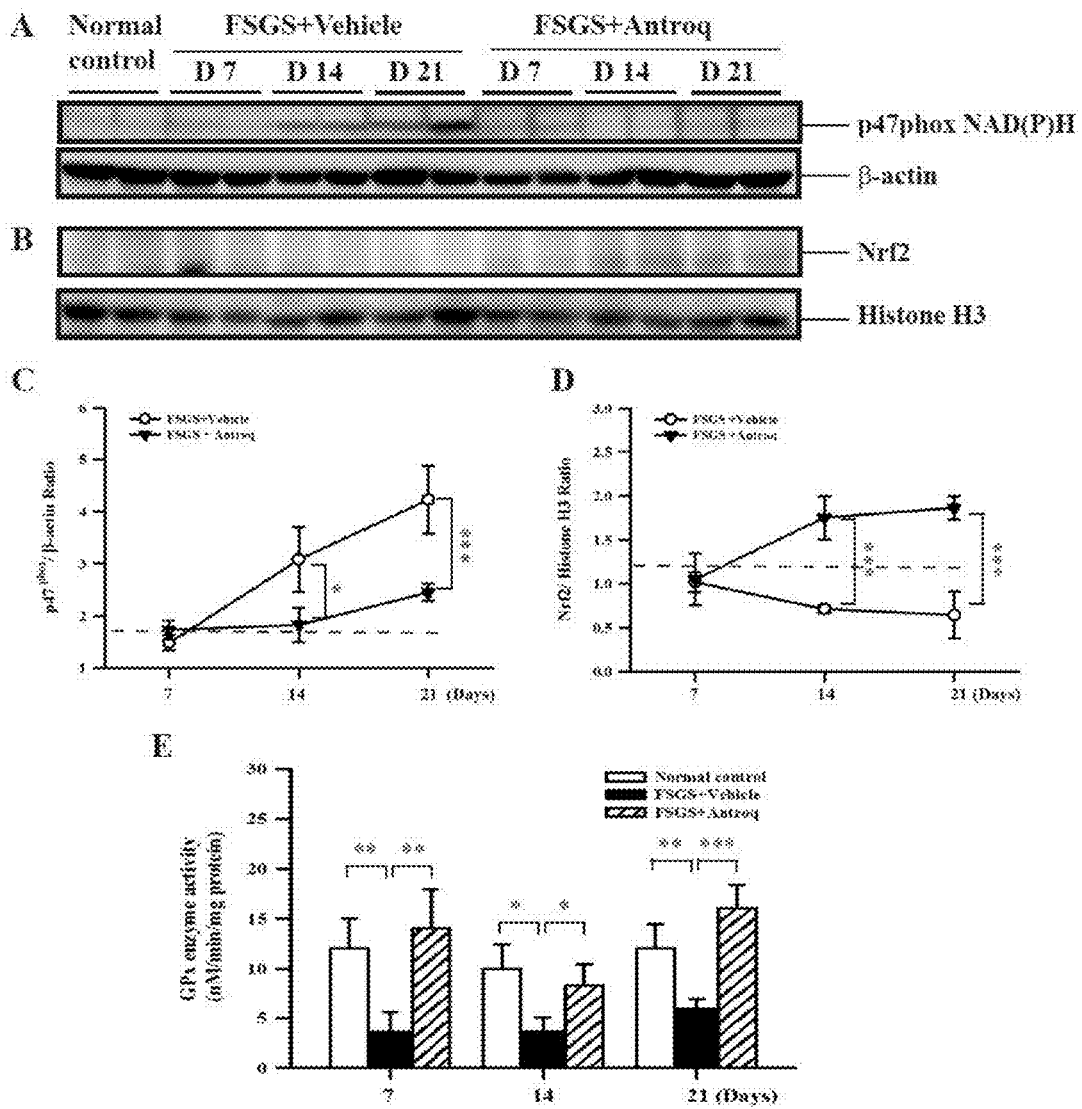

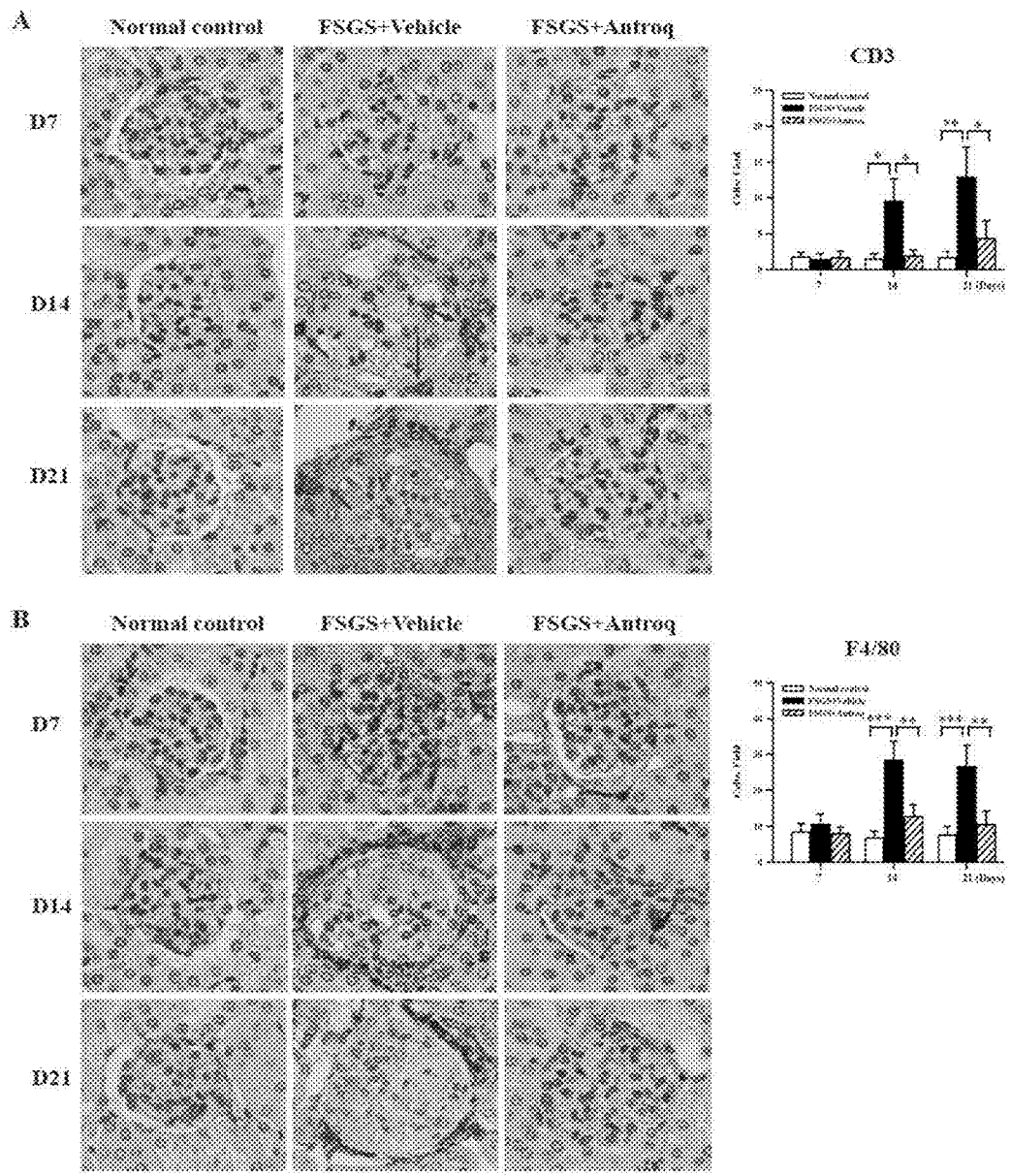
FIG. 5A-B

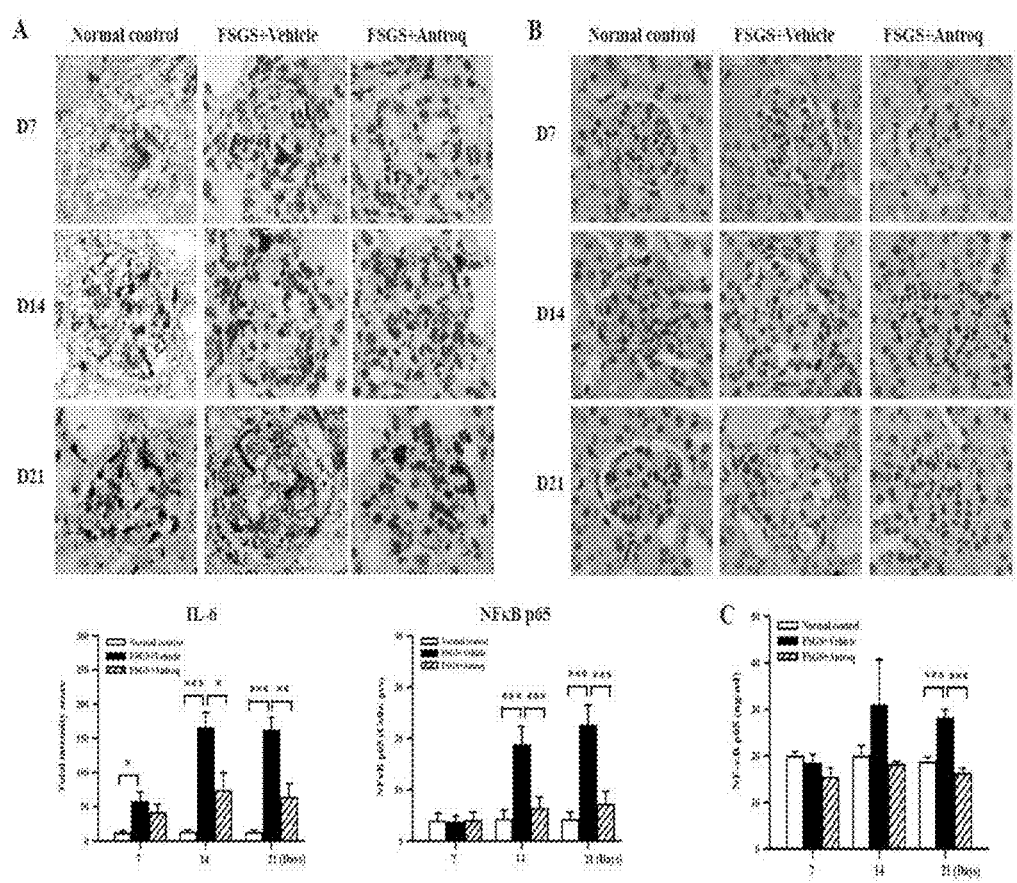
FIG. 6A-C

FIG. 7A-C
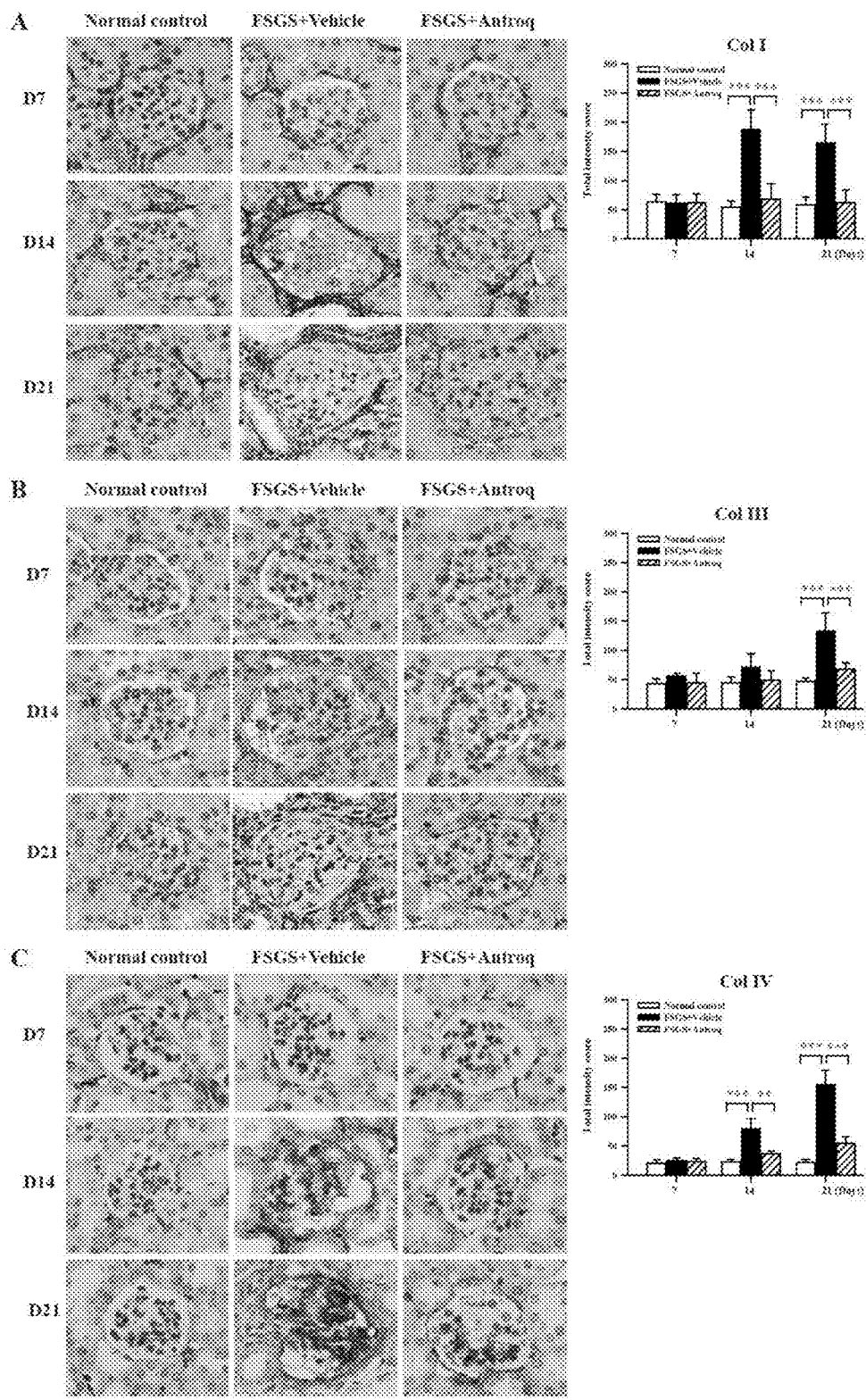

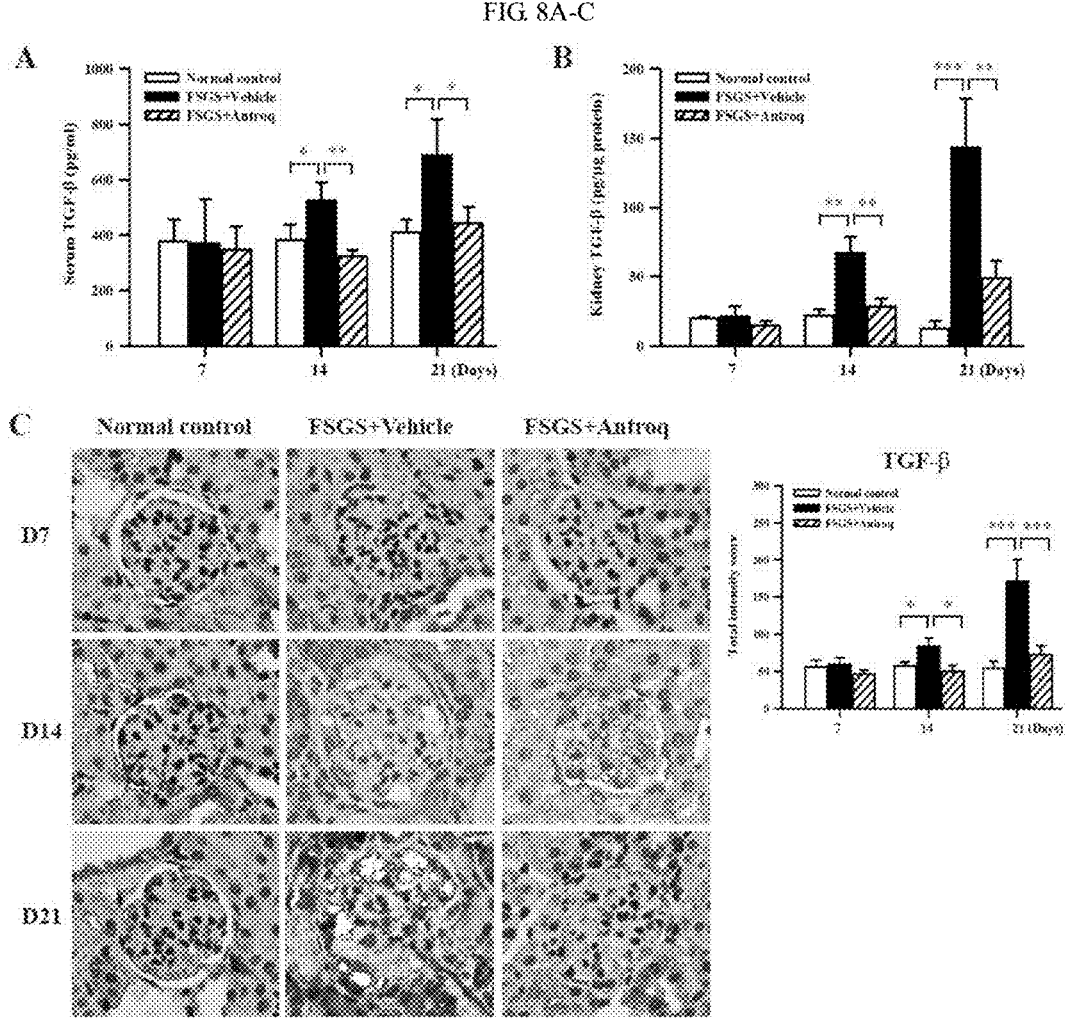
FIG. 8A-C

FIG. 9A-B
9A
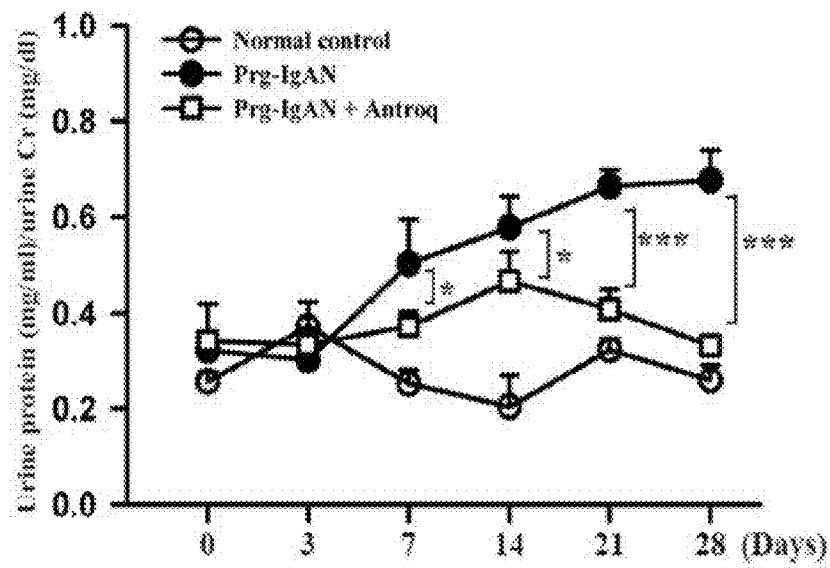
9B
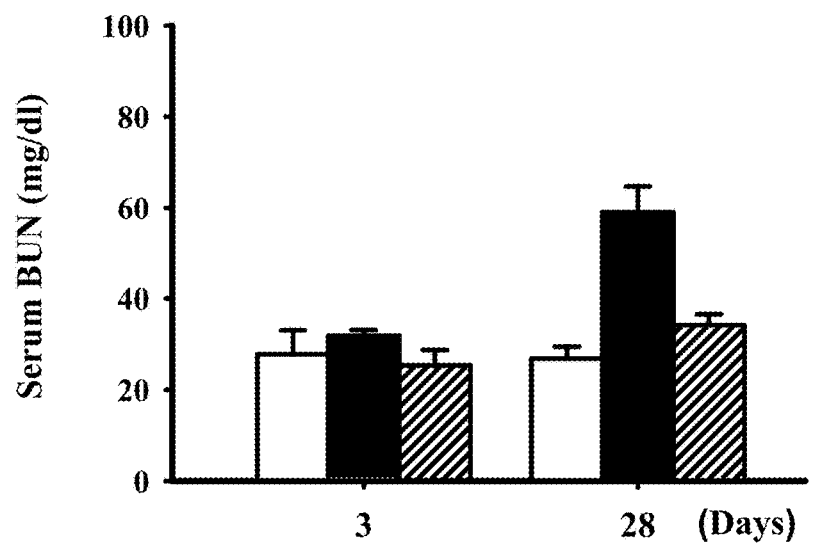

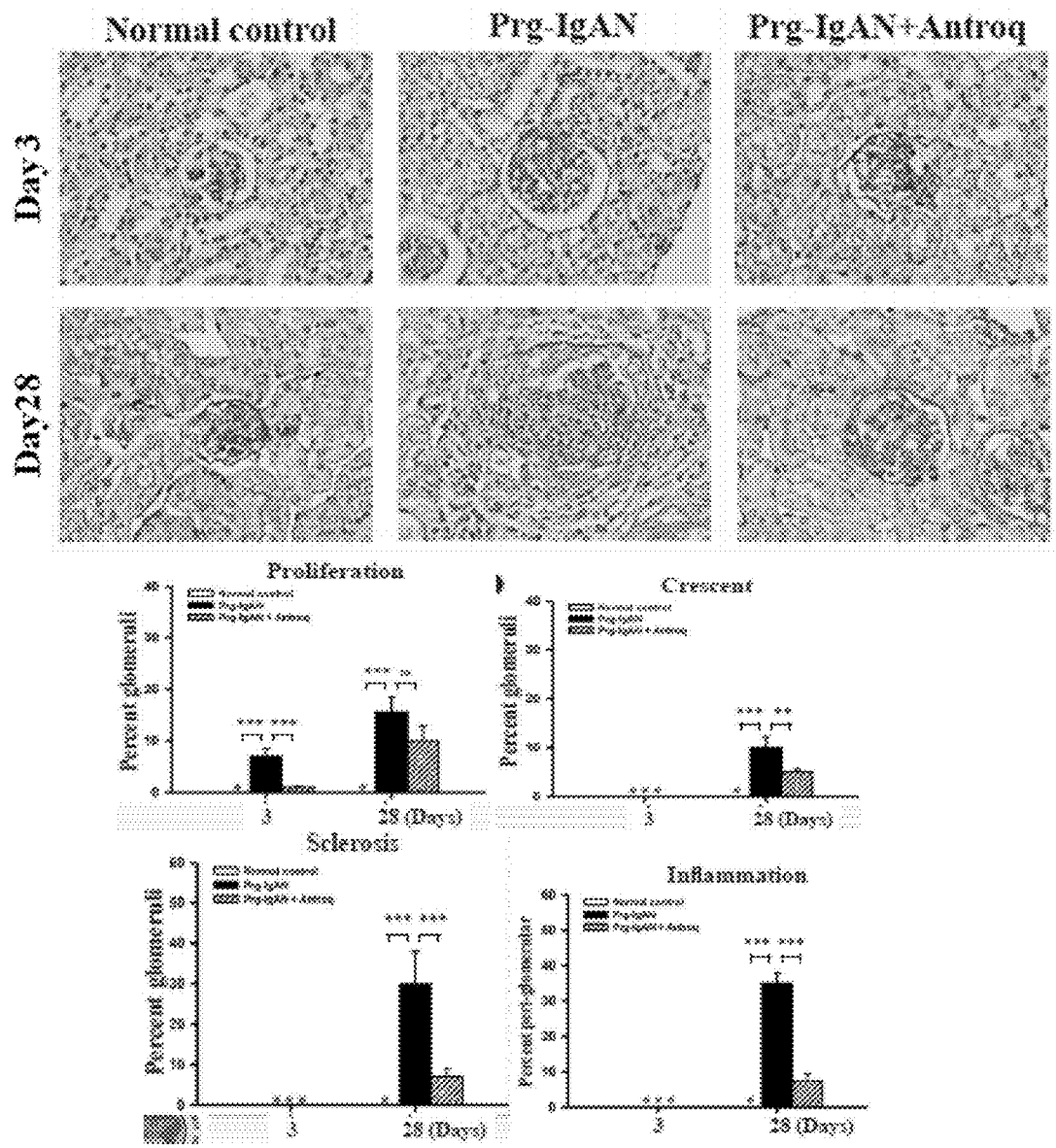

FIG. 10A-B
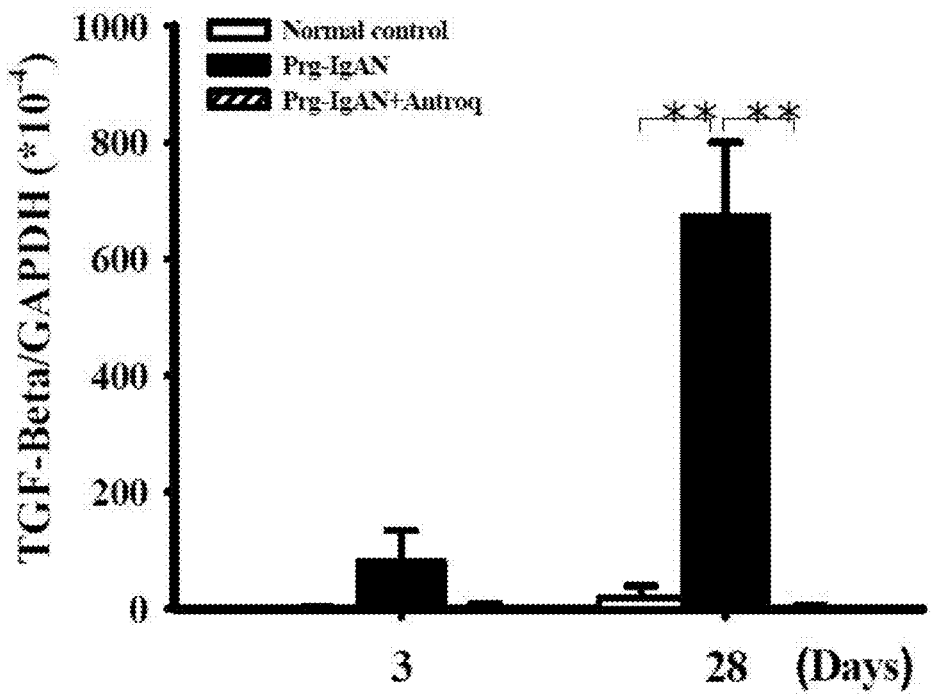
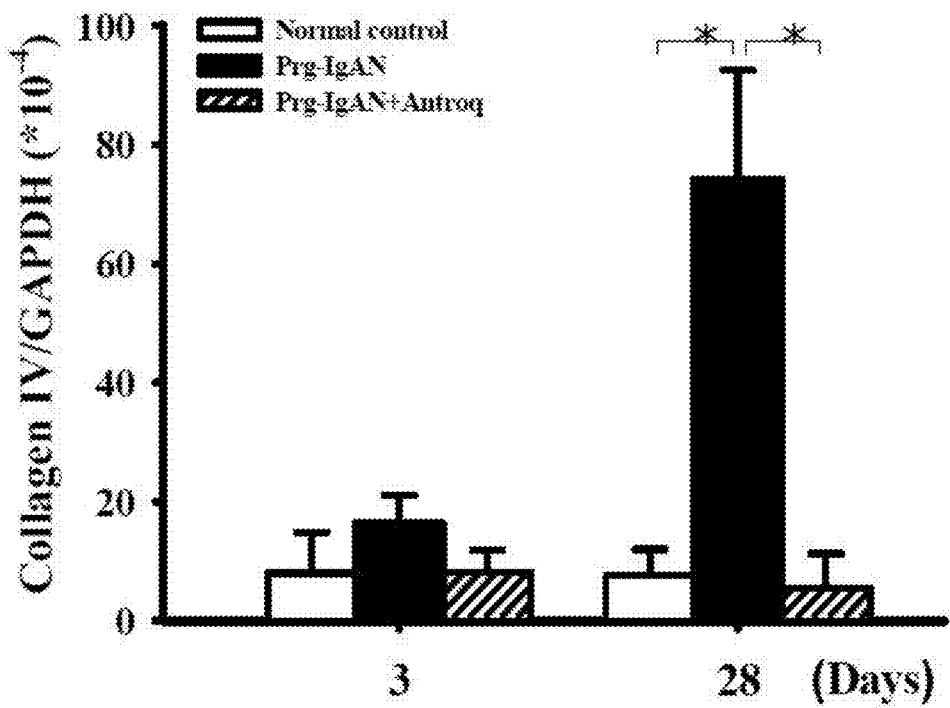

FIG. 11A-B
11A
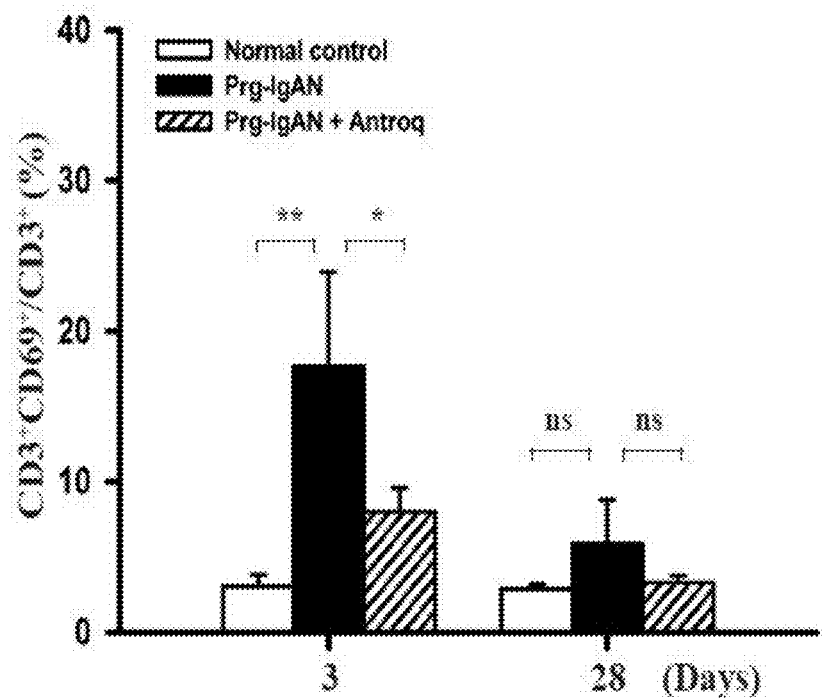
11B
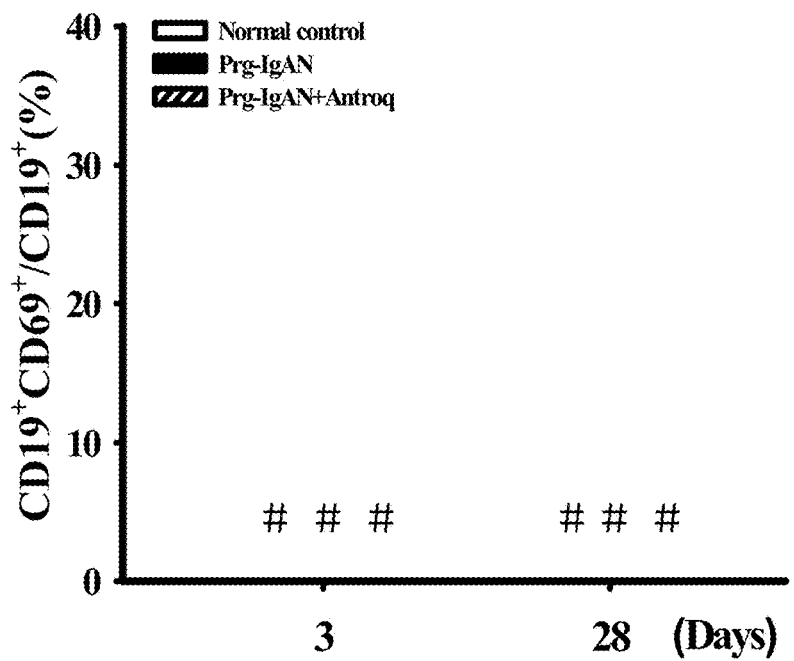

FIG. 12A-B
12A
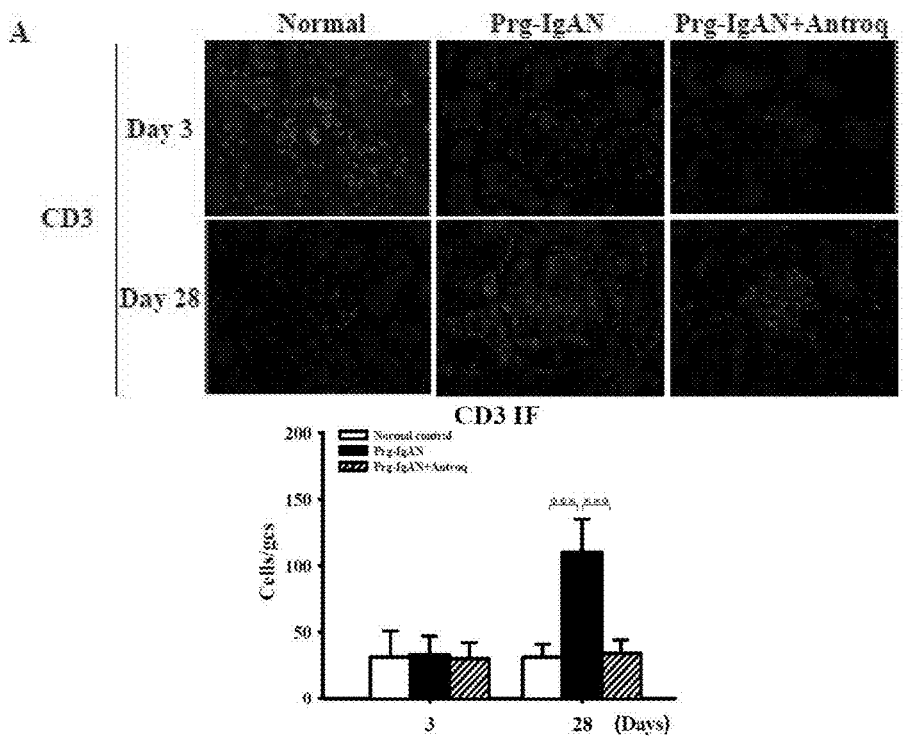
12B
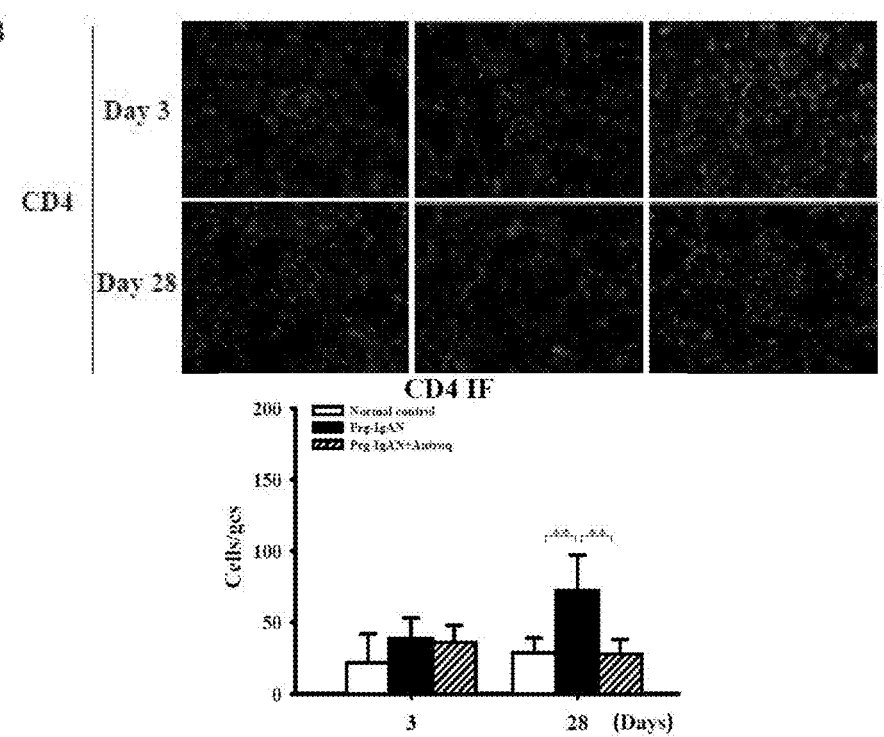

FIG. 13A-B
13A
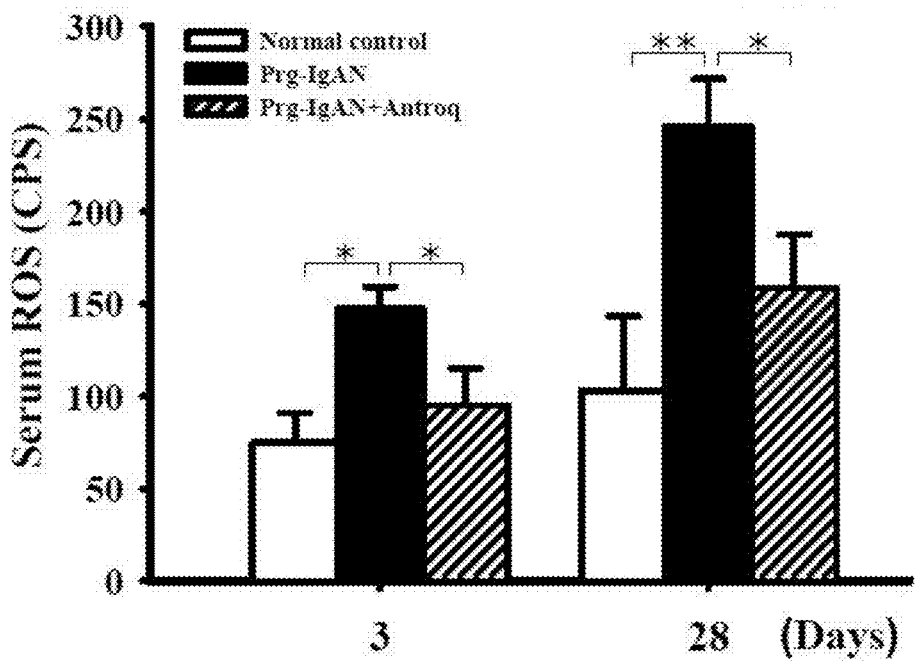
13B
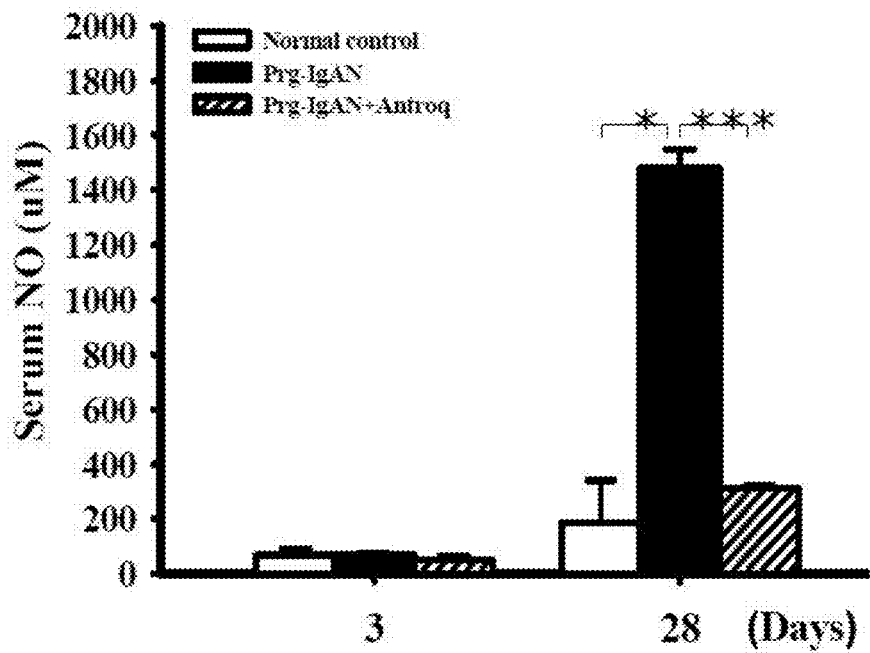

FIG. 13C-D
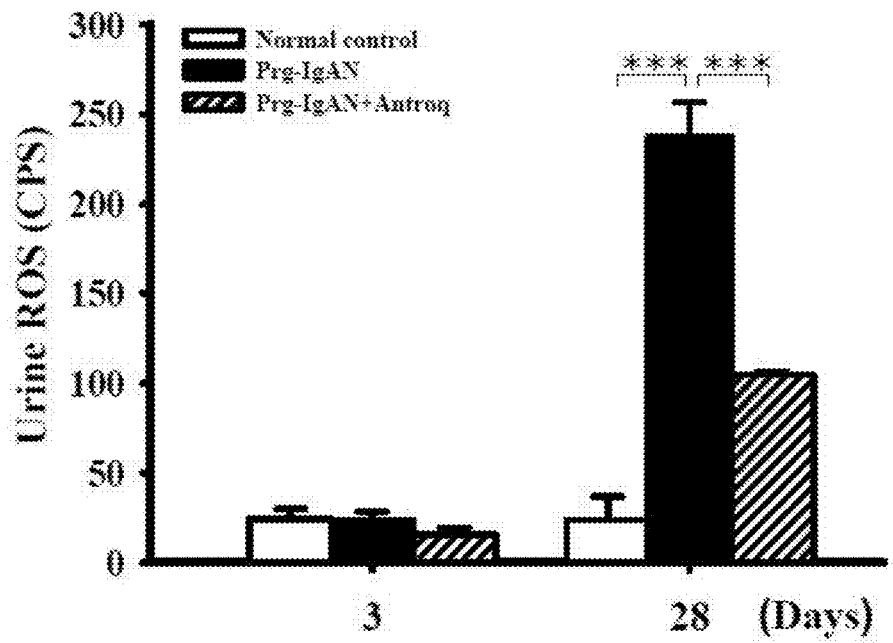
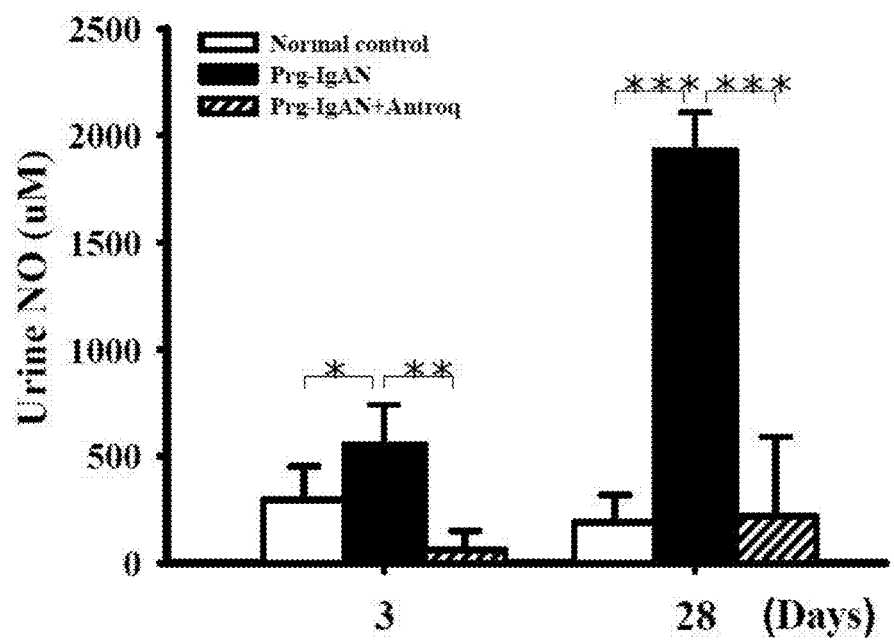

FIG. 13E-F
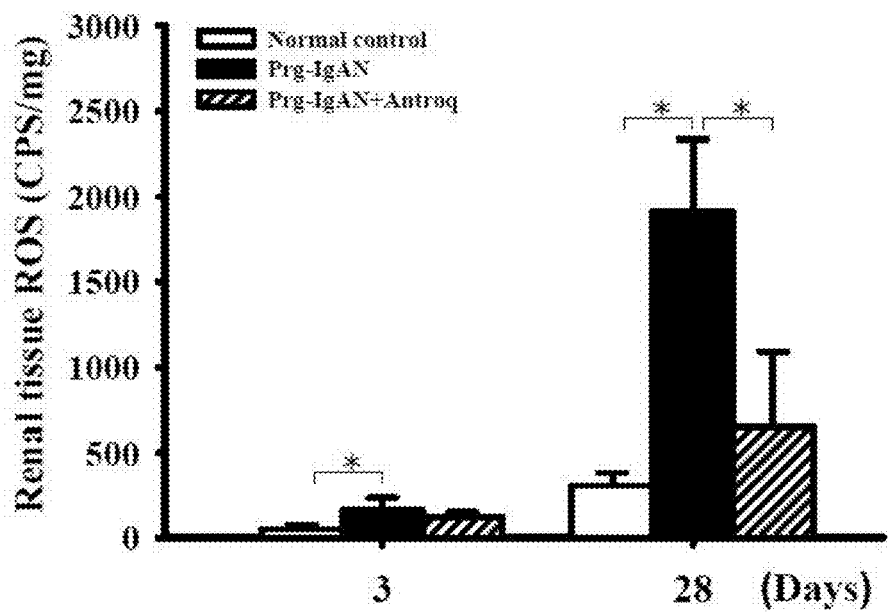
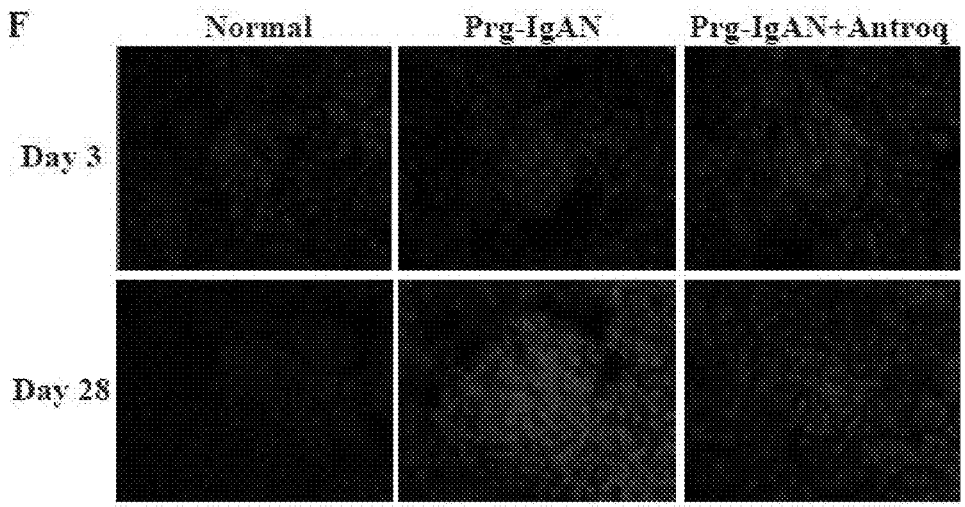
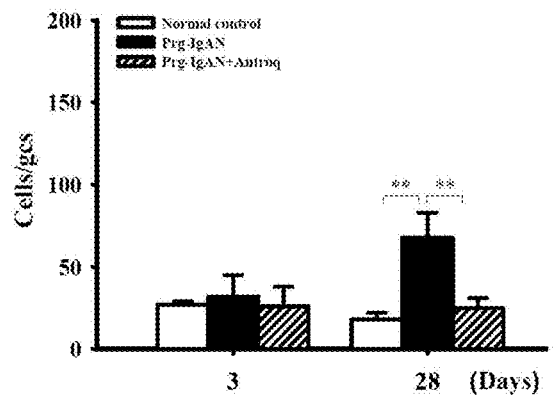

FIG. 14A-B
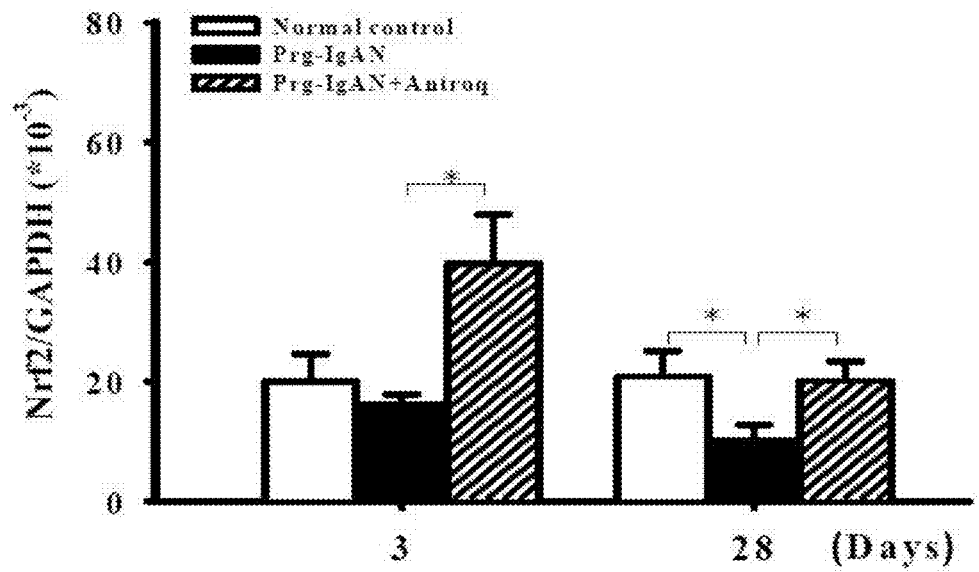
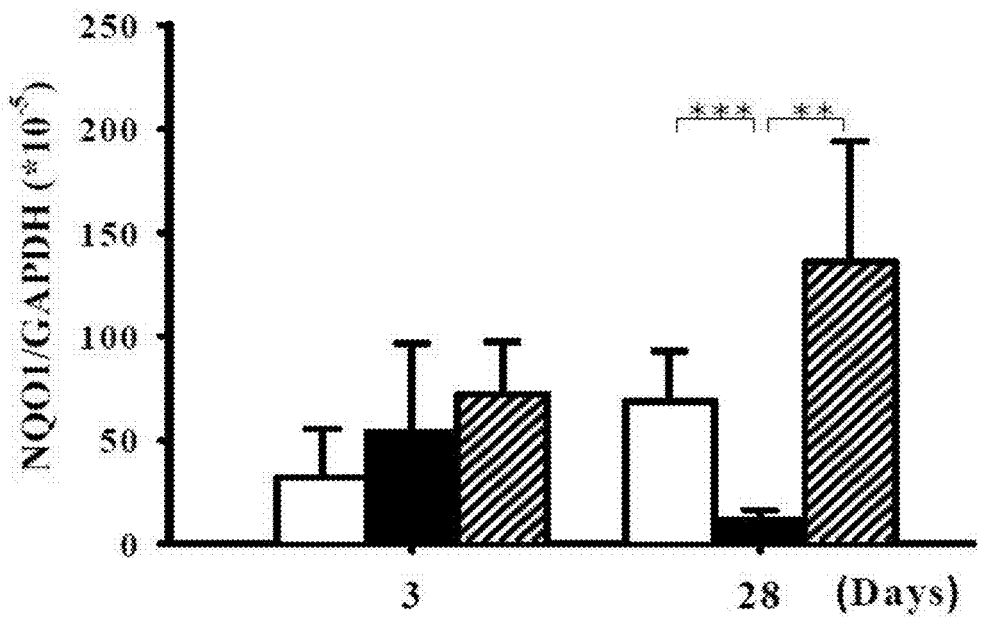

FIG. 14C-D
14C
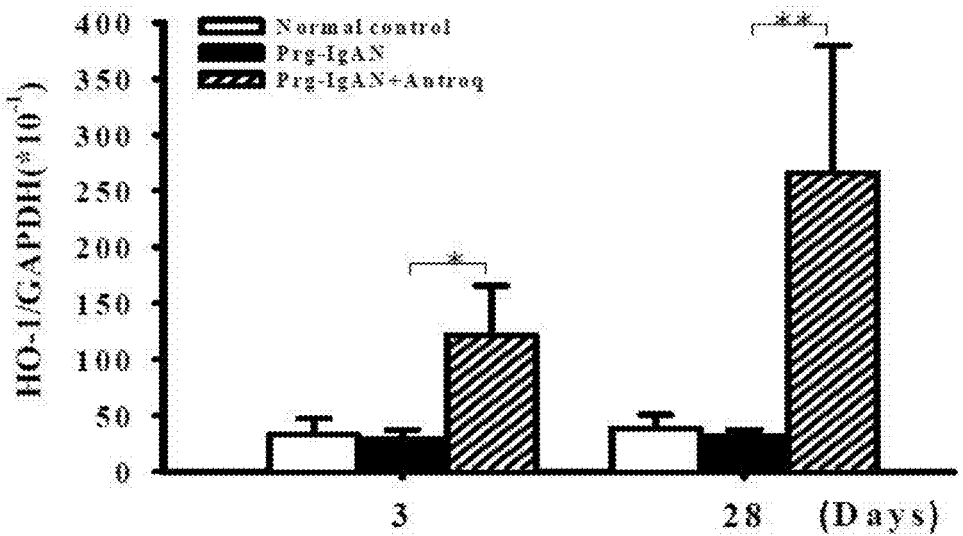
14D
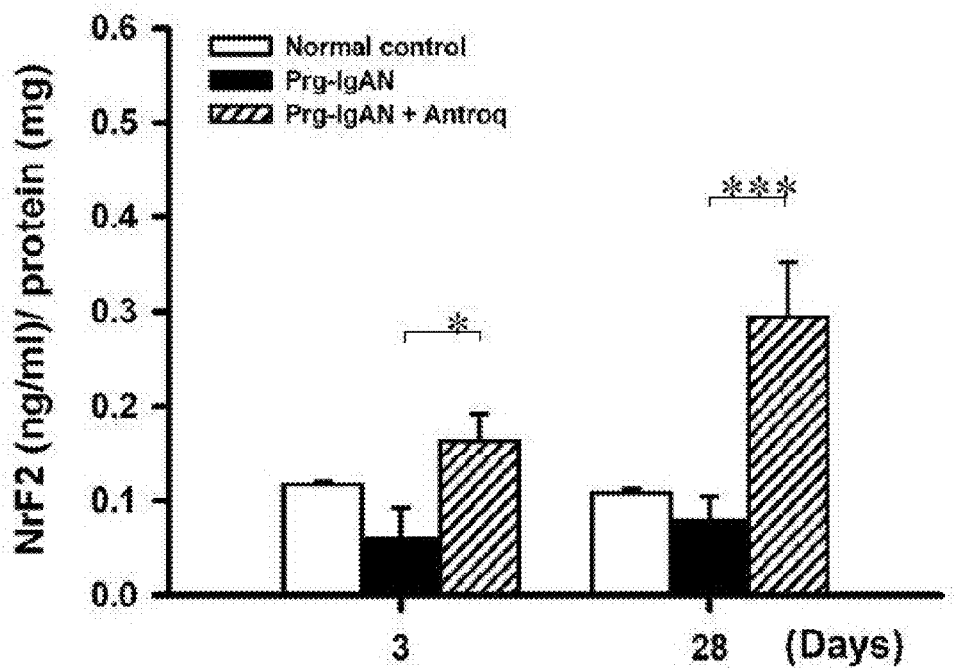

FIG. 14E-F
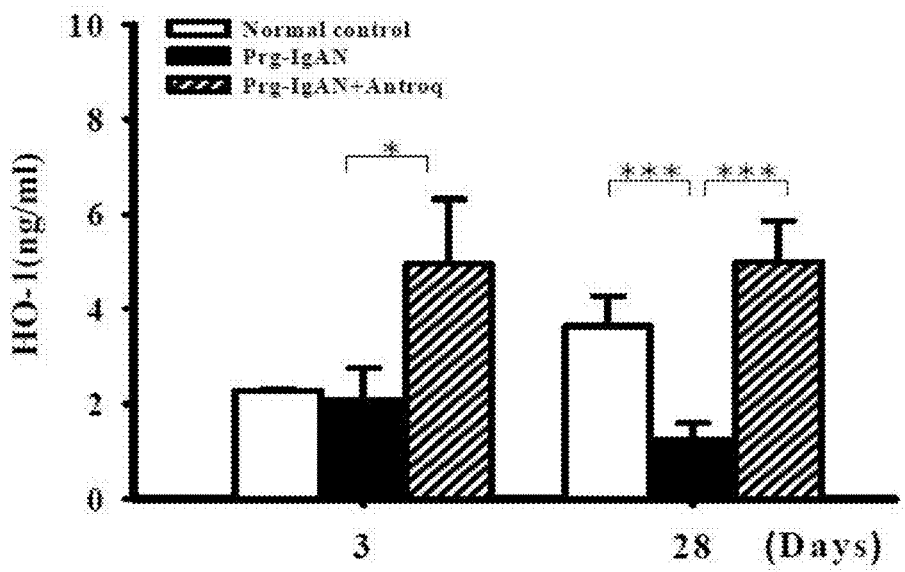
14E
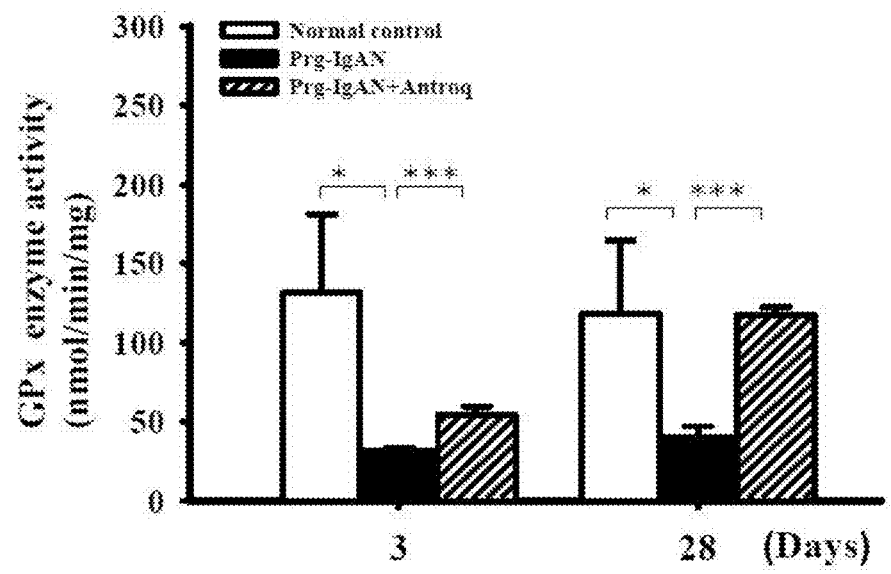
14F

FIG. 15A-B
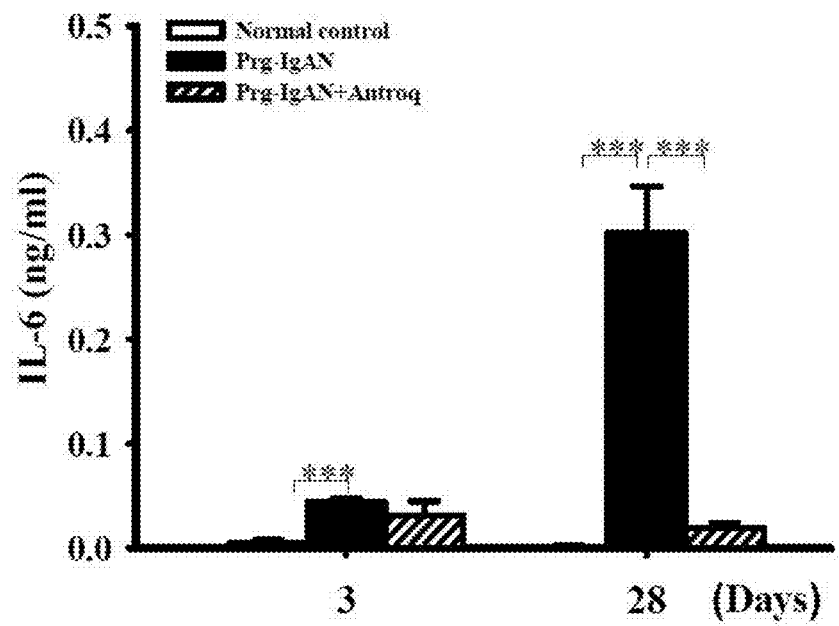
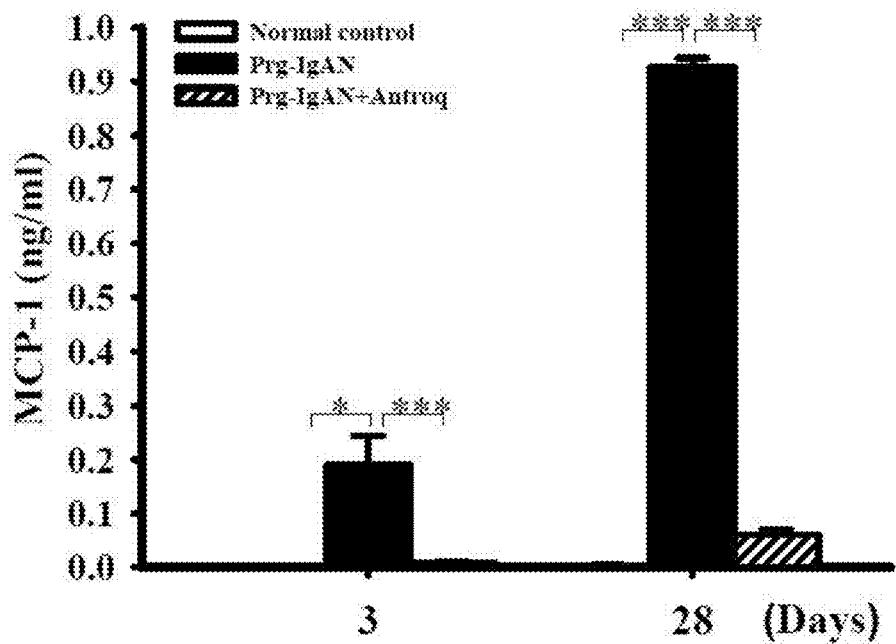

FIG. 15C-D
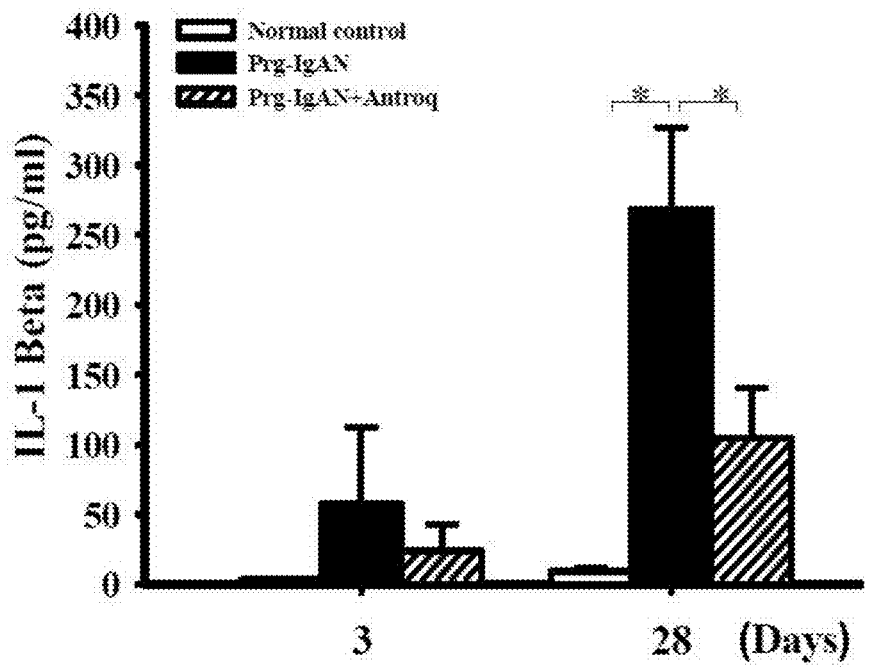
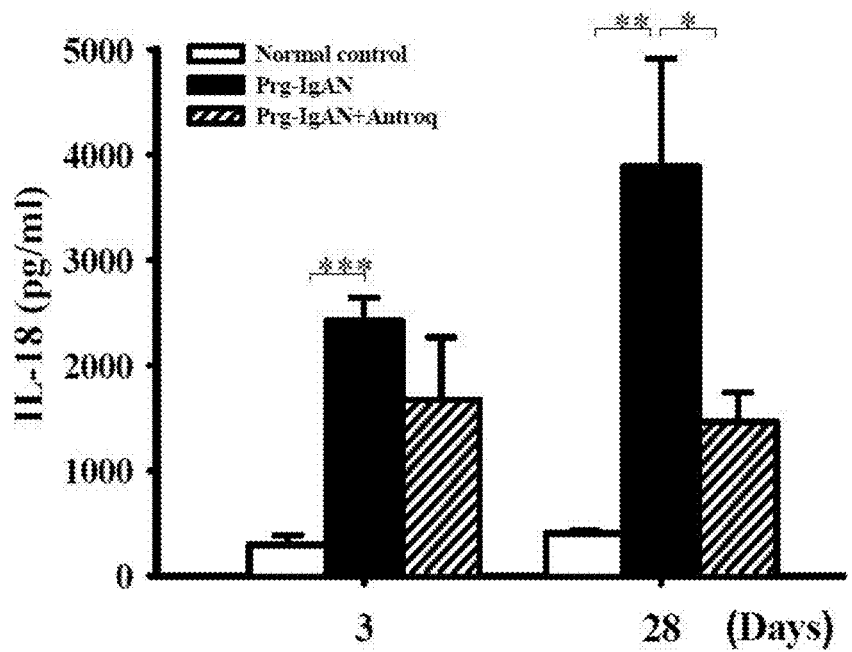

FIG. 16A-B
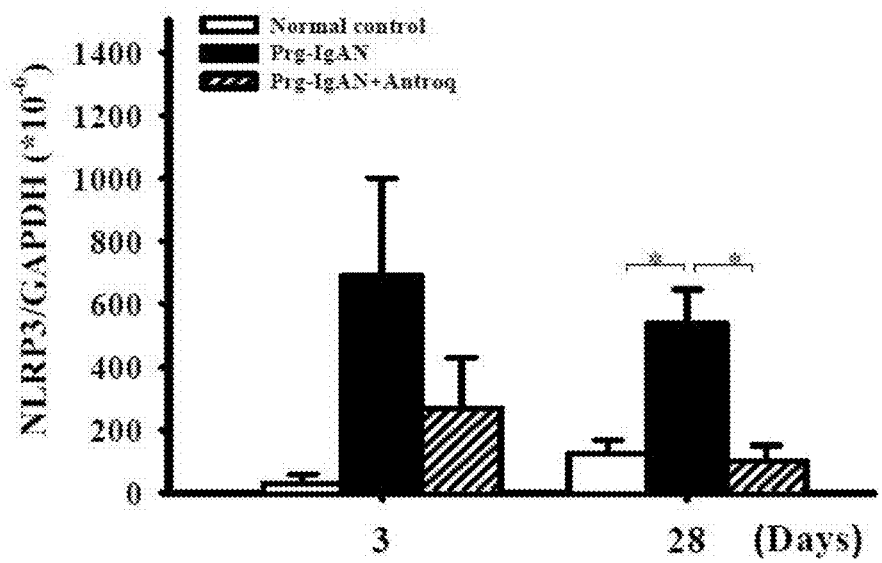
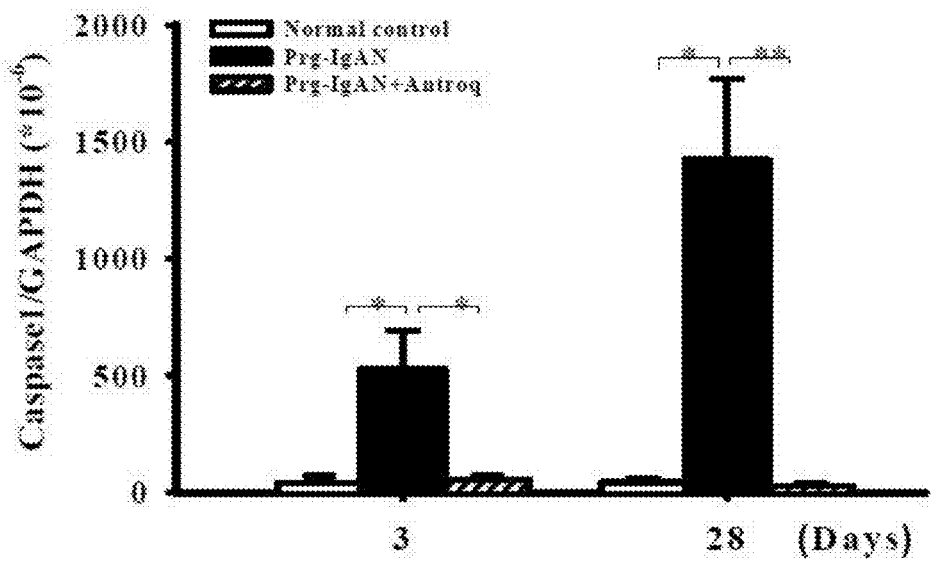

FIG. 16C-D
16C
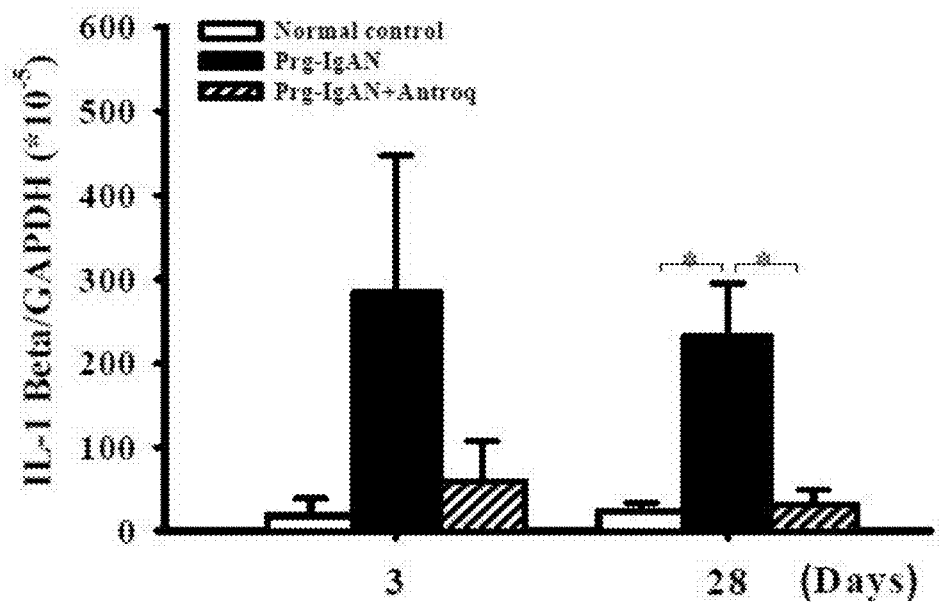
16D
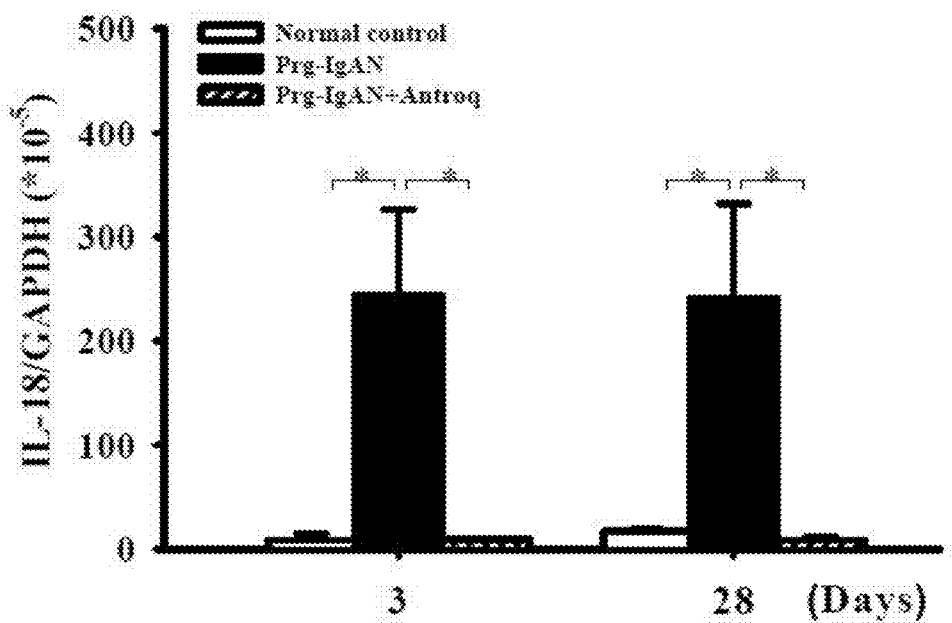

FIG. 16E-F
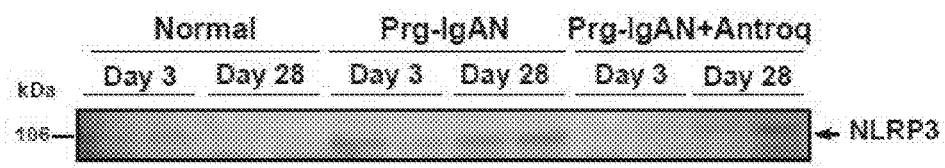
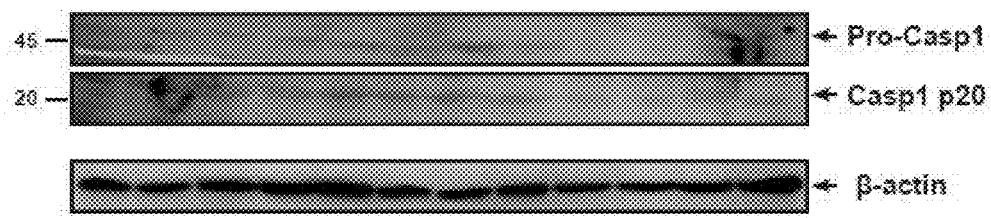

FIG. 17A-B
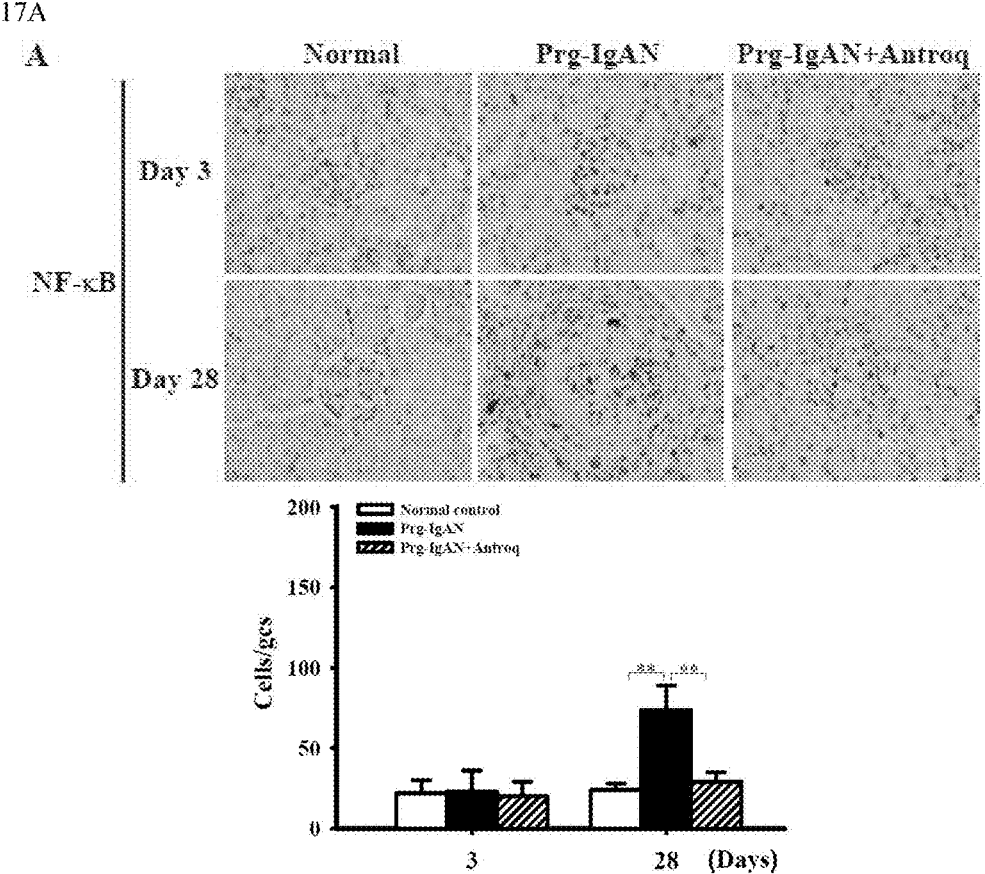
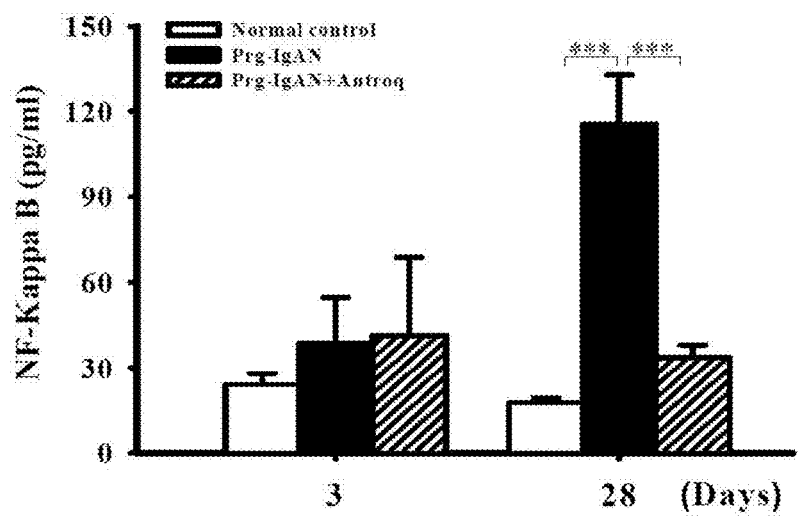

FIG. 17C-D
17C
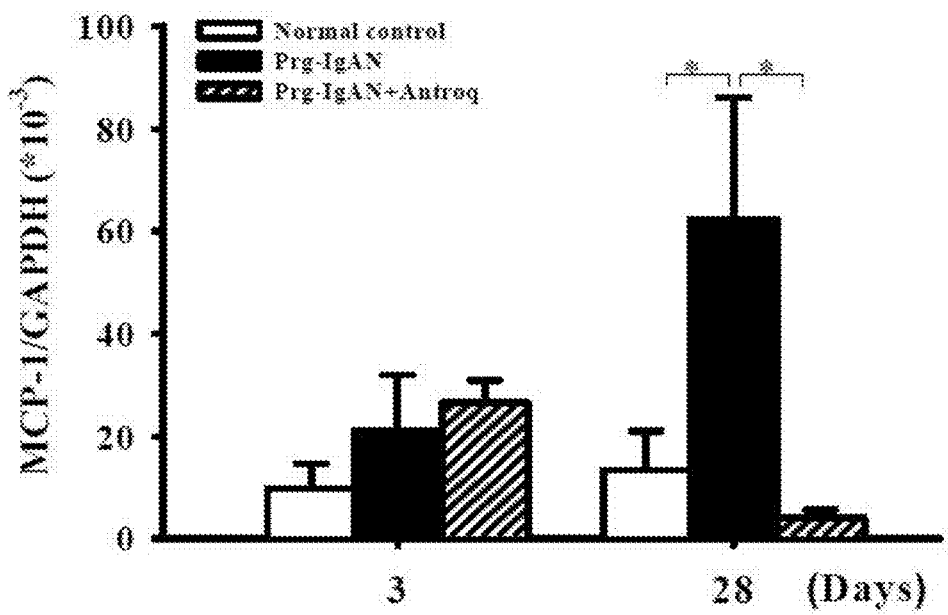
17D
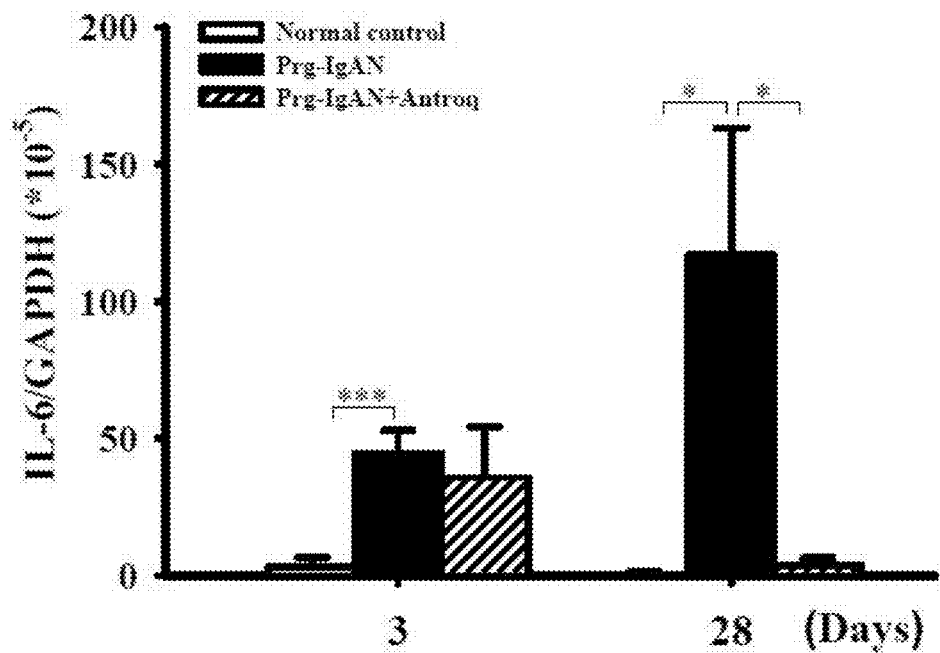

FIG. 17E-F
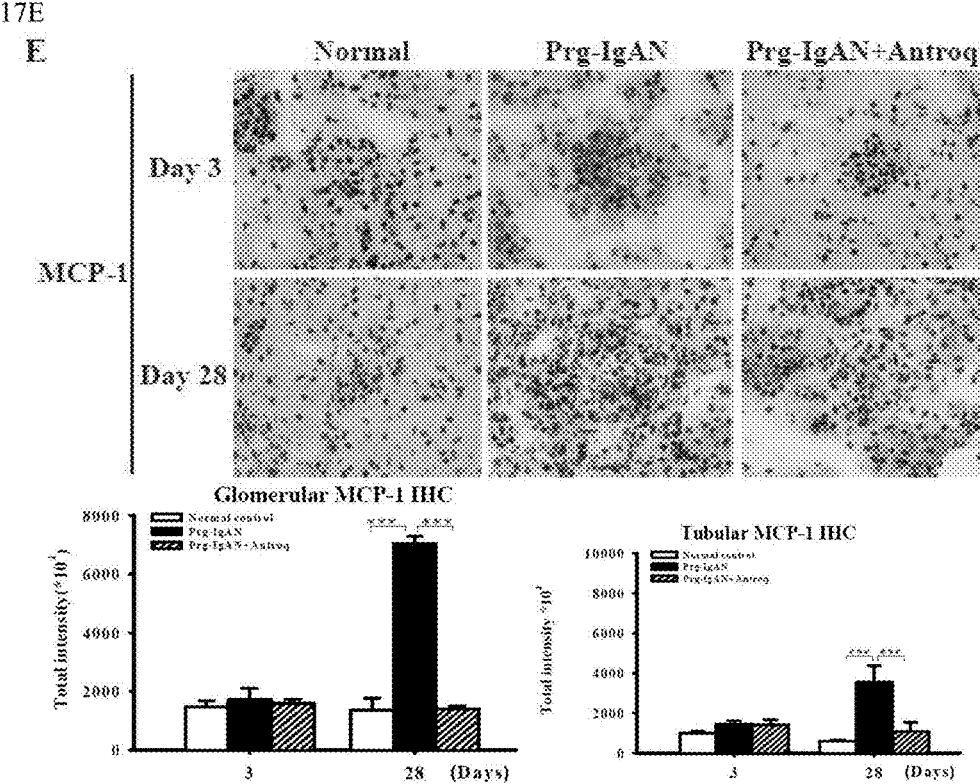
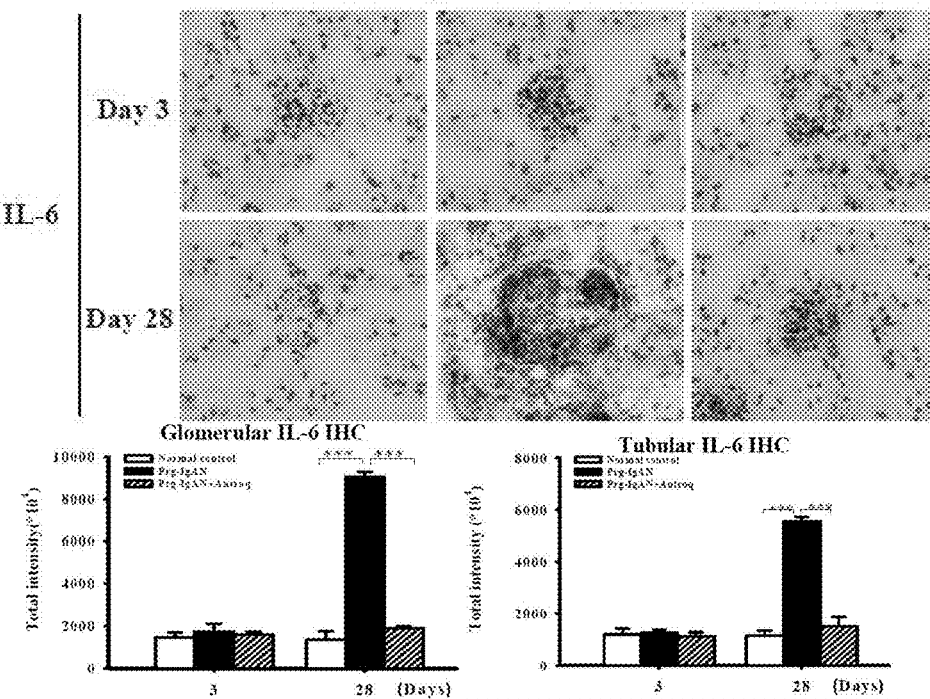

FIG. 18A-B
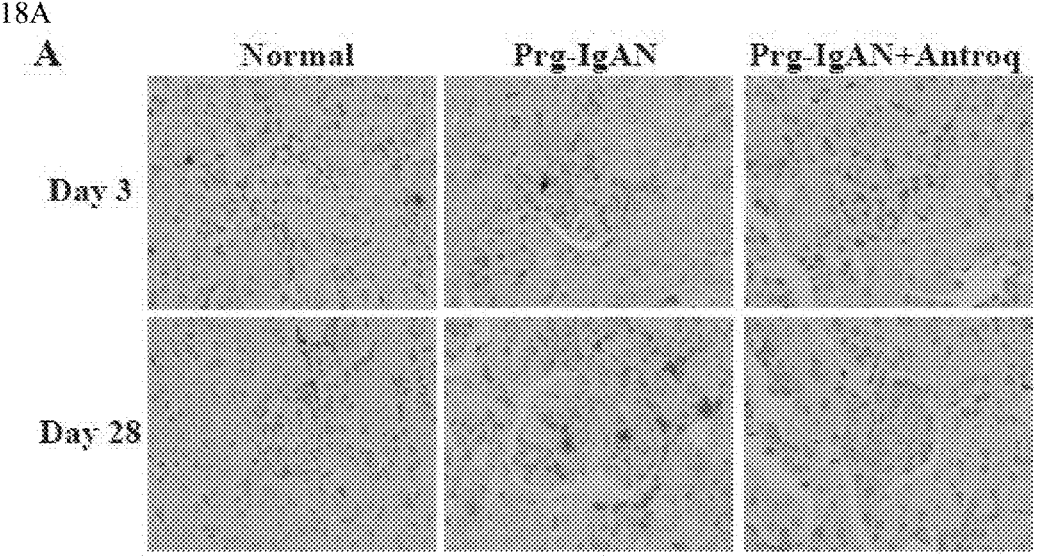
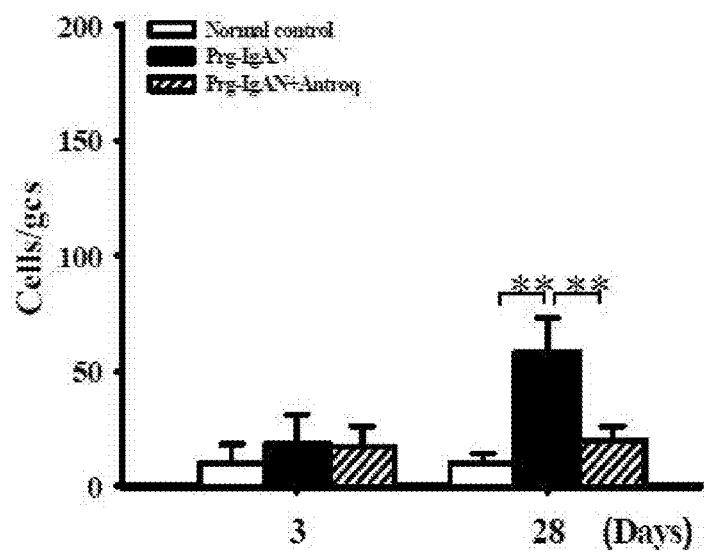

METHODS AND COMPOSITIONS FOR TREATING KIDNEY DISORDERS

CROSS-REFERENCE

This application is a continuation application of U.S. application Ser. No. 13/980,791, a National Phase Application of PCT/US2012/022118, which claims the benefit of U.S. Application No. 61/435,201, filed Jan. 21, 2011, and U.S. Application No. 61/544,910, filed Oct. 7, 2011, each of which is incorporated herein by reference in its entirety.

BACKGROUND OF THE INVENTION

Many diseases or disorders affect kidney function by attacking the glomeruli. Glomerular diseases include many conditions with a variety of genetic and environmental causes, but they fall into two major categories, Glomerulonephritis and Glomerulosclerosis.

Glomerulosclerosis refers to a hardening of the glomerulus in the kidney. It is a general term to describe scarring of the kidneys' tiny blood vessels, the glomeruli, the functional units in the kidney that filter urine from the blood. Proteinuria (large amounts of protein in urine) is one of the signs of glomerulosclerosis. Scarring disturbs the filtering process of the kidneys and allows protein to leak from the blood into urine. However, glomerulosclerosis is one of many causes of proteinuria. A kidney biopsy may be necessary to determine whether a patient has glomerulosclerosis or another kidney problem. Glomerulosclerosis, more specifically, can refer to focal segmental glomerulosclerosis (FSGS) and nodular diabetic glomerulosclerosis.

Focal segmental glomerulosclerosis (FSGS) is defined by the characteristic lesions of focal glomerular sclerosis and foot process effacement. The reported frequency of end-stage renal disease in patients with FSGS ranges widely from 13 to 78% in studies with up to 20 years of follow-up. Although the etiology and pathogenesis of FSGS remains unclear, it is believed to mainly arise from an intrinsic insult to the glomerular epithelial cell that activates complex interactions within the glomerulus, whereby resulting in glomerulosclerosis.

Nodular diabetic glomerulosclerosis or intercapillary glomerulonephritis, also known as diabetic nephropathy (nephropatia diabetica) or Kimmelstiel-Wilson syndrome is a progressive kidney disease caused by angiopathy of capillaries in the kidney glomeruli. It is characterized by nephrotic syndrome and diffuse glomerulosclerosis. It is due to longstanding diabetes mellitus, and is a prime indication for dialysis in many countries.

At present, although corticosteroids and immunemodulatory agents are commonly used to treat patients with primary FSGS, the outcome of therapy in terms of progression of the renal lesions is poor, in addition to their various side effects and these regimens of treatment are based more on empirical assumptions than pathogenetic evidence. (See for example, Matalon, et al., *Semin Nephrol,* 20: 309-317, 2000; Braun, et al., *Cochrane Database Syst Rev: CD*003233, 2008).

Glomerulonephritis describes the inflammation of the membrane tissue in the kidney that serves as a filter, separating wastes and extra fluid from the blood.

Acceleration and progression during the course of Immunoglobulin A nephropathy (IgAN), the most common type of primary glomerulonephritis, is relatively unpredictable and clinically remains a challenge in terms of prophylaxis and treatment, and has been considered to be a key step in subsequent development of chronic renal failure of the glomerular disorder. In this regard, abnormal enhancement of both systemic T cell activation and lymphocyte/macrophage/neutrophil infiltration in the kidney of IgAN patients has been considered as a major detrimental process in converting IgAN into chronic renal failure (Kamei, et al., *Clin. J. Am. Soc. Nephrol.* 2011, 14; Chan, et al., *Clin. Exp. Nephrol.* 2004, 8:297-303; Chao, et al., *Kidney Int.* 70:283-297 (2006); Lai, K. N., *Nephron.* 92:263-270 (2002)), although other immunological, clinical, and pathological factors may also be attributable. Furthermore, oxidative stress has been highly implicated in the development and progression of IgAN in patients and animal models; reactive oxygen species (ROS) has been reported to play an immediate pathogenic role in the development of a wide range of human and experimental glomerular disorders, including IgAN.

Although glucocorticoid steroids has been employed to treat IgAN patients, their efficacy of preserving renal function and reducing proteinuria in IgAN remains unclear, and adverse side effects are still a problematic concern because of potential uncontrollable immunosuppressive effects for long term use.

SUMMARY OF THE INVENTION

In one aspect provides herein methods for the treatment of glomerular diseases (e.g., glomerulosclerosis or glomerulonephritis) in a subject comprising administering to the subject an effective amount of a cyclohexenone compound having the structure:

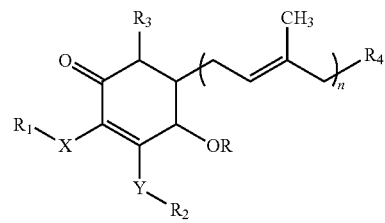

wherein each of X and Y independently is oxygen, $NR_5$ or sulfur;
R is a hydrogen or $C(=O)C_1-C_8$alkyl;
each of $R_1$, $R_2$ and $R_3$ independently is a hydrogen, methyl or $(CH_2)_m—CH_3$;
$R_4$ is $NR_5R_6$, $OR_5$, $OC(=O)R_7$, $C(=O)OR_5$, $C(=O)R_5$, halogen, 5 or 6-membered lactone, $C_1-C_8$alkyl, $C_2-C_8$alkenyl, $C_2-C_8$alkynyl, aryl, glucosyl, wherein the 5 or 6-membered lactone, $C_1-C_8$alkyl, $C_2-C_8$alkenyl, $C_2-C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1-C_8$ alkyl, $C_2-C_8$ alkenyl, $C_2-C_8$ alkynyl, $C_3-C_8$ cycloalkyl, $C_1-C_8$ haloalkyl, and $C_1-C_8$ alkoxy;
each of $R_5$ and $R_6$ is independently a hydrogen or $C_1-C_8$alkyl;
$R_7$ is a $C_1-C_8$alkyl, $OR_5$ or $NR_5R_6$;
m=1-12; and
n=1-12; or a pharmaceutically acceptable salt, metabolite, solvate or prodrug thereof.

In another aspect provides herein methods for attenuating renal dysfunction or glomerular lesions in a subject comprising administering to the subject an effective amount of a cyclohexenone compound having the structure:

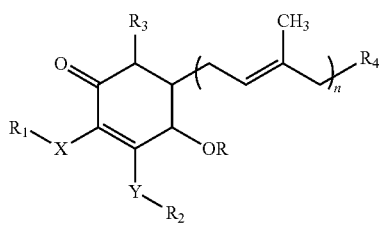

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods for enhancing renal nuclear factor E2-related factor 2 (Nrf2) activity in a subject comprising administering to the subject an effective amount of a cyclohexenone compound having the structure:

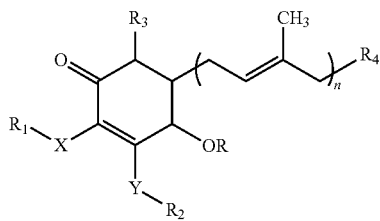

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods for inhibiting renal NF-κB activation and/or transforming growth factor (TGF)-β1 protein expression in a subject comprising administering to the subject an effective amount of a cyclohexenone compound having the structure:

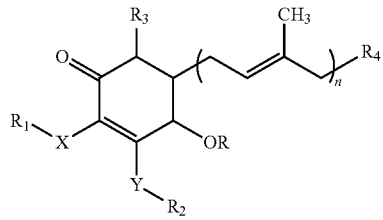

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods for inhibiting ROS/NO and/or p47$^{phox}$ in a subject comprising administering to the subject an effective amount of a cyclohexenone compound having the structure:

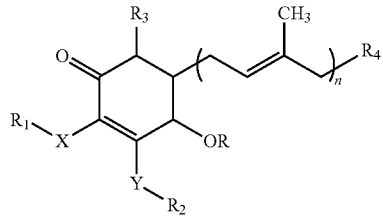

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods for reducing $CD3^+/CD69^+$ T cells in a subject comprising administering to the subject an effective amount of a cyclohexenone compound having the structure:

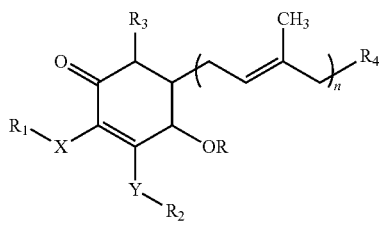

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods for enhancing glutathione peroxidase (GPx) activity in the kidney comprising administering to a subject an effective amount of a cyclohexenone compound having the structure:

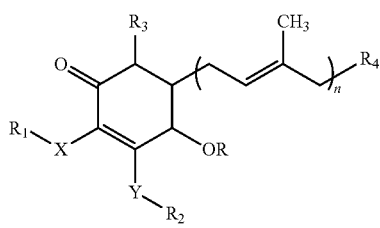

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods for reducing pro-inflammatory cytokines in a subject comprising administering to the subject an effective amount of a cyclohexenone compound having the structure:

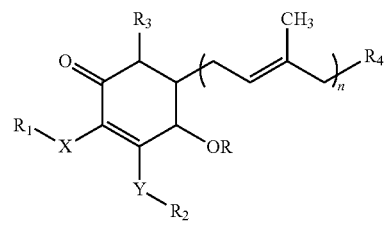

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods for reducing renal caspase-1 protein expression and/or inhibiting renal NLRP3 activation in the kidney comprising administering to a subject an effective amount of a cyclohexenone compound having the structure:

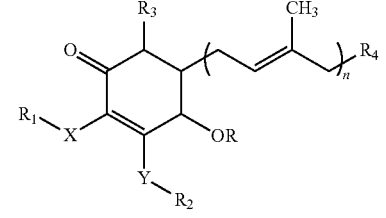

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

R₄ is NR₅R₆, OR₅, OC(=O)R₇, C(=O)OR₅, C(=O)R₅, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from NR₅R₆, OR₅, OC(=O)R₇, C(=O)OR₅, C(=O)R₅, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of R₅ and R₆ is independently a hydrogen or $C_1$-$C_8$alkyl;

R₇ is a $C_1$-$C_8$alkyl, OR₅ or NR₅R₆;

m=1-12; and n=1-12; or a pharmaceutically acceptable salt, metabolite, solvate or prodrug thereof.

In yet another aspect provides herein methods for reducing renal NF-κB level in the kidney comprising administering to a subject an effective amount of a cyclohexenone compound having the structure:

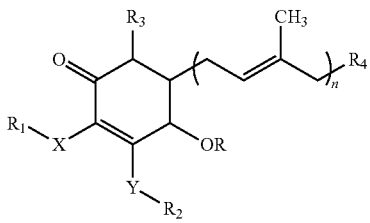

wherein each of X and Y independently is oxygen, NR₅ or sulfur;

R is a hydrogen or C(=O)$C_1$-$C_8$alkyl;

each of R₁, R₂ and R₃ independently is a hydrogen, methyl or $(CH_2)_m$—$CH_3$;

R₄ is NR₅R₆, OR₅, OC(=O)R₇, C(=O)OR₅, C(=O)R₅, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from NR₅R₆, OR₅, OC(=O)R₇, C(=O)OR₅, C(=O)R₅, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of R₅ and R₆ is independently a hydrogen or $C_1$-$C_8$alkyl;

R₇ is a $C_1$-$C_8$alkyl, OR₅ or NR₅R₆;

m=1-12; and n=1-12; or a pharmaceutically acceptable salt, metabolite, solvate or prodrug thereof.

In yet another aspect provides herein method for inhibiting apoptosis in the kidney comprising administering to a subject an effective amount of a cyclohexenone compound having the structure:

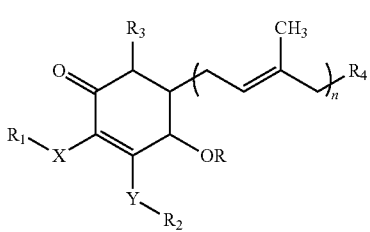

wherein each of X and Y independently is oxygen, NR₅ or sulfur;

R is a hydrogen or C(=O)$C_1$-$C_8$alkyl;

each of R₁, R₂ and R₃ independently is a hydrogen, methyl or $(CH_2)_m$—$CH_3$;

R₄ is NR₅R₆, OR₅, OC(=O)R₇, C(=O)OR₅, C(=O)R₅, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from NR₅R₆, OR₅, OC(=O)R₇, C(=O)OR₅, C(=O)R₅, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of R₅ and R₆ is independently a hydrogen or $C_1$-$C_8$alkyl;

R₇ is a $C_1$-$C_8$alkyl, OR₅ or NR₅R₆;

m=1-12; and n=1-12; or a pharmaceutically acceptable salt, metabolite, solvate or prodrug thereof.

In another aspect provides herein methods for protecting or preventing kidney from glomerulosclerosis and/or interstitial fibrosis and/or glomerulonephritis in a subject comprising administering to the subject an effective amount of a cyclohexenone compound having the structure

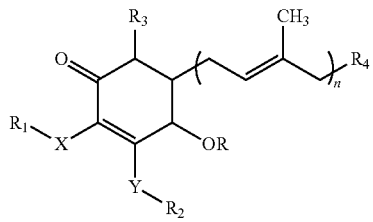

which decreases the expression levels of TGF-β1 protein and collagen I, III and IV protein accumulation in the kidney, wherein each of X and Y independently is oxygen, NR₅ or sulfur;

R is a hydrogen or C(=O)$C_1$-$C_8$alkyl;

each of R₁, R₂ and R₃ independently is a hydrogen, methyl or $(CH_2)_m$—$CH_3$;

R₄ is NR₅R₆, OR₅, OC(=O)R₇, C(=O)OR₅, C(=O)R₅, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from NR₅R₆, OR₅, OC(=O)R₇, C(=O)OR₅, C(=O)R₅, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of R₅ and R₆ is independently a hydrogen or $C_1$-$C_8$alkyl;

R₇ is a $C_1$-$C_8$alkyl, OR₅ or NR₅R₆;

m=1-12; and n=1-12; or a pharmaceutically acceptable salt, metabolite, solvate or prodrug thereof.

In yet another aspect provides methods for the treatment of focal segmental glomerulosclerosis (FSGS) in a subject, which comprises administering to the subject a therapeutically effective amount of a cyclohexenone compound having the structure

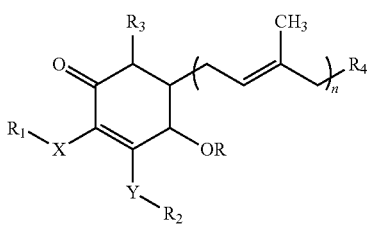

that (i) enhances Nrf2 activity and/or (ii) suppresses NF-κB-dependent inflammatory and TGF-β1-mediated fibrosis in the kidney, wherein R is a hydrogen or $C(=O)C_1\text{-}C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)R_5$, halogen, 5 or 6-membered lactone, $C_1\text{-}C_8$alkyl, $C_2\text{-}C_8$alkenyl, $C_2\text{-}C_8$alkynyl, aryl, glucosyl, wherein the 5 or 6-membered lactone, $C_1\text{-}C_8$alkyl, $C_2\text{-}C_8$alkenyl, $C_2\text{-}C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1\text{-}C_8$ alkyl, $C_2\text{-}C_8$ alkenyl, $C_2\text{-}C_8$ alkynyl, $C_3\text{-}C_8$ cycloalkyl, $C_1\text{-}C_8$ haloalkyl, and $C_1\text{-}C_8$ alkoxy;
each of $R_5$ and $R_6$ is independently a hydrogen or $C_1\text{-}C_8$alkyl;
$R_7$ is a $C_1\text{-}C_8$alkyl, $OR_5$ or $NR_5R_6$;
m=1-12; and
n=1-12; or a pharmaceutically acceptable salt, metabolite, solvate or prodrug thereof.

In yet another aspect provides methods for the treatment of glomerulonephritis in a subject, which comprises administering to the subject a therapeutically effective amount of a cyclohexenone compound having the structure

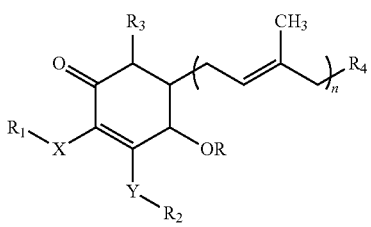

that (i) blocking renal NLRP3 inflammasome activation and/or (ii) inhibiting the increase in T cell activation, wherein each of X and Y independently is oxygen, $NR_5$ or sulfur;

R is a hydrogen or $C(=O)C_1\text{-}C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)R_5$, halogen, 5 or 6-membered lactone, $C_1\text{-}C_8$alkyl, $C_2\text{-}C_8$alkenyl, $C_2\text{-}C_8$alkynyl, aryl, glucosyl, wherein the 5 or 6-membered lactone, $C_1\text{-}C_8$alkyl, $C_2\text{-}C_8$alkenyl, $C_2\text{-}C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1\text{-}C_8$ alkyl, $C_2\text{-}C_8$ alkenyl, $C_2\text{-}C_8$ alkynyl, $C_3\text{-}C_8$ cycloalkyl, $C_1\text{-}C_8$ haloalkyl, and $C_1\text{-}C_8$ alkoxy;
each of $R_5$ and $R_6$ is independently a hydrogen or $C_1\text{-}C_8$alkyl;
$R_7$ is a $C_1\text{-}C_8$alkyl, $OR_5$ or $NR_5R_6$;
m=1-12; and
n=1-12; or a pharmaceutically acceptable salt, metabolite, solvate or prodrug thereof.

In yet another aspect provides methods for maintaining immunoglobulin A nephropathy (IgAN) in remission in a subject, which comprises administering to the subject an effective amount of a cyclohexenone compound having the structure

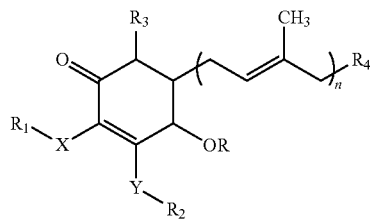

that (i) enhances Nrf2 activity and/or (ii) suppresses NF-κB-dependent inflammatory and TGF-β1-mediated fibrosis in the kidney, wherein each of X and Y independently is oxygen, $NR_5$ or sulfur;
R is a hydrogen or $C(=O)C_1\text{-}C_8$alkyl;
each of $R_1$, $R_2$ and $R_3$ independently is a hydrogen, methyl or $(CH_2)_m$—$CH_3$;
$R_4$ is $NR_5R_6$, $OR_5$, $OC(=O)R_7$, $C(=O)OR_5$, $C(=O)R_5$, halogen, 5 or 6-membered lactone, $C_1\text{-}C_8$alkyl, $C_2\text{-}C_8$alkenyl, $C_2\text{-}C_8$alkynyl, aryl, glucosyl, wherein the 5 or 6-membered lactone, $C_1\text{-}C_8$alkyl, $C_2\text{-}C_8$alkenyl, $C_2\text{-}C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1\text{-}C_8$ alkyl, $C_2\text{-}C_8$ alkenyl, $C_2\text{-}C_8$ alkynyl, $C_3\text{-}C_8$ cycloalkyl, $C_1\text{-}C_8$ haloalkyl, and $C_1\text{-}C_8$ alkoxy;
each of $R_5$ and $R_6$ is independently a hydrogen or $C_1\text{-}C_8$alkyl;
$R_7$ is a $C_1\text{-}C_8$alkyl, $OR_5$ or $NR_5R_6$;
m=1-12; and
n=1-12; or a pharmaceutically acceptable salt, metabolite, solvate or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A-C show illustrative results from the exemplary cyclohexenone Compound 1 to reduce urinary protein and improve renal function. (1A) Urinary protein time-course studies. (1B) Serum blood urea nitrogen (BUN) levels. (1C) Serum creatinine levels. The data are the mean±SEM for six mice per group. *p<0.05, p<0.01, *p<0.005. #Not detectable.

FIG. 2A-B show illustrative results of the renal histopathology development prevention by the exemplary cyclohexenone Compound 1. (2A) Kidney histopathological evaluation by H&E staining on day 7, 14, and 21 of treatment. (2B) Detection of podocyte injury in glomeruli by immunohistochemical staining of desmin on day 7, 14, and 21 of treatment. The black arrow head, white arrow head, and arrow indicate the epithelial hyperplasia lesions (EPHLs), sclerosis, and podocytes, respectively. Original magnification, 400×. Semi-quantitative analysis is shown in the right panel. The data are the mean±SEM for six mice per group. *$p<0.05$, $p<0.01$, *$p<0.005$. #Not detectable.

FIG. 3A-F show illustrative results that an exemplary cyclohexenone Compound 1 protects against ROS/NO production in FSGS mice. (3A) Superoxide anion levels in serum. (3B) NO levels in serum. (3C) Superoxide anion levels in urine. (3D) NO levels in urine. (3E) Superoxide anion levels in kidney protein. (3F) kidney in-situ ROS production demonstrated by dihydroethidium (DHE) labeling. Original magnification, 400×. Semi-quantitative analysis is shown in the right panel. The data are the mean±SEM for six mice per group. *$p<0.05$, $p<0.01$, *$p<0.005$.

FIG. 4A-E show illustrative results from the exemplary cyclohexenone Compound 1 enhancing nuclear Nrf2 expression and decreasing cytosolic p47$^{phox}$ expression in the kidney. (4A) Representative Western blots of cytosolic p47$^{phox}$ and (4B) nuclear Nrf2 in kidney tissues. β-Actin and Histone H3 were used as internal controls for cytosolic and nuclear proteins, respectively. (4C) Quantification of the p47$^{phox}$/β-actin ratio and (4D) the Nrf2/ Histone H3 ratio. (4E) GPx activity in the kidney. The data are the mean±SEM for six mice per group. *$p<0.05$, $p<0.01$, *$p<0.005$.

FIG. 5A-B show illustrative results of T cell and macrophage infiltration with the exemplary cyclohexenone Compound 1. (5A) Detection of CD3$^+$ T cells or (5B) F4/80 monocytes/macrophages by immunohistochemical staining. Original magnification, 400×. The red arrow indicate the CD3$^+$ T cells. Semi-quantitative analysis is shown in the right panel. The data are the mean±SEM for six mice per group. *$p<0.05$, $p<0.01$, *$p<0.005$.

FIG. 6A-C show illustrative results from the exemplary cyclohexenone Compound 1 suppressing IL-6 expression and NF-κB activation in the kidney. (6A) Detection of IL-6 protein and (6B) NF-κB p65 by immunohistochemical staining. Original magnification, 400×. Semi-quantitative analysis is shown in the lower panel. (4C) Kidney NF-κB activity. The data are the mean±SEM for six mice per group. *$p<0.05$, $p<0.01$, *$p<0.005$.

FIG. 7A-C show illustrative results from the exemplary cyclohexenone Compound 1 for the prevention of collagen I, III and IV accumulation in the kidney. (7A) Detection of collagen I, (7B) collagen III, or (7C) collagen IV by immunohistochemical staining. Original magnification, 400×. Semi-quantitative analysis is shown in the right panel. The data are the mean±SEM for six mice per group. $p<0.01$, *$p<0.005$.

FIG. 8A-C show illustrative results from the exemplary cyclohexenone Compound 1 for the prevention of TGF-β1 expression in serum and kidney tissues. (8A) TGF-β1 levels in serum. (8B) TGF-β1 levels in kidney protein. (8C) Detection of TGF-β1 by immunohistochemical staining. Original magnification, 400×. Semi-quantitative analysis is shown in the right panel. The data are the mean±SEM for six mice per group. *$p<0.05$, $p<0.01$, *$p<0.005$.

FIG. 9A-9E show illustrative results from the exemplary cyclohexenone Compound 1 to reduce urinary protein and improve renal function and severe renal histopathology in AcP-IgAN mice. (9A) Urine protein time-course studies. (9B) Serum blood urea nitrogen (BUN) levels. (9C) Serum creatinine levels. Kidney histopathological evaluation by H&E staining (9D) and PAS staining (9E) at day 3 and 28 of treatment. Original magnification, 400×. The scoring of the percentage of glomeruli affected by the indicated parameter is shown in the lower panels. The data are the mean±SEM for six mice per group. *$p<0.05$, $p<0.01$, *$p<0.005$. #Not detectable.

FIG. 10A-D show illustrative results of both mRNA and protein levels of TGF-β1 and Col-IV in the AcP-IgAN mice fed with the exemplary Compound 1. Detection renal mRNA levels of TGF-β1 (10A) and collagen I (10B) by real-time PCR. Detection renal protein levels of TGF-β1 (10C) and collagen I (10D) by immunohistochemical staining. Original magnification, 400×. The scoring is shown in the lower panels. The data are the mean±SEM for six mice per group. $p<0.01$, *$p<0.005$.

FIG. 11A-C show illustrative results of cell mediated immunity in the pathogenesis of IgAN by cytometry in splenocytes. Percentage of CD3$^+$CD69$^+$ cells in CD3$^+$ splenocytes (11A) or CD19$^+$ CD69$^+$ cells in CD19$^+$ splenocytes (11B) at day 3 and 28 of treatment. (11C) T cell proliferation. The data are the mean±SEM for six mice per group. *$p<0.05$, $p<0.01$, *$p<0.005$. #Not detectable.

FIG. 12A-F show illustrative results of evaluation of the phenotypic expression of mononuclear leukocytes that infiltrated in the kidney of the Acp-IgAN mice. (12A-C) Detection of CD3$^+$ T cells (12A), CD4$^+$ T cells (12B), or CD8$^+$ T cells (12C) by immunofluorescence staining. (12D-F) Detection of CD11b macrophages/neutrophils (12D), CD11c dendritic cells (12E), or F4/80 monocytes/macrophages (12F) by immunohistochemical staining. Original magnification, 400×. The scoring is shown in the lower panels. The data are the mean±SEM for six mice per group. *$p<0.05$, $p<0.01$, *$p<0.005$. #Not detectable.

FIG. 13A-F show illustrative results that the exemplary cyclohexenone Compound 1 protects against ROS/NO production in AcP-IgAN mice. (FIGS. 13A and 13B) Serum levels of superoxide anion (13A) or NO (13B). (FIGS. 13C and 13D) Urine levels of superoxide anion (13C) or NO (13D). (FIG. 13E) Superoxide anion levels in the kidney. (FIG. 13F) Kidney in situ ROS production demonstrated by dihydroethidium (DHE) labeling. Original magnification, 400×. The scoring is shown in the right panel. The data are the mean±SEM for six mice per group. *$p<0.05$, $p<0.01$, *$p<0.005$.

FIG. 14A-F show illustrative results of the expression levels of both mRNA and protein of Nrf2 in AcP-IgAN mice. (14A-C) Detection renal mRNA levels of Nrf2 (14A), NQO1 (14B), or HO-1 (14C) by real-time PCR. (14D-E) Detection renal levels of nuclear Nrf2 (14D) or cytosolic HO-1 (14E) by ELISA. (14F) GPx activity in the kidney. The data are the mean±SEM for six mice per group. *$p<0.05$, $p<0.01$, *$p<0.005$.

FIG. 15A-D show illustrative results of serum levels of inflammatory cytokines in AcP-IgAN mice. (15A) IL-6. (15B) MCP-1. (15C) IL-1β. (15D) IL-18. The data are the mean±SEM for six mice per group. *$p<0.05$, $p<0.01$, *$p<0.005$.

FIG. 16A-F show illustrative results of renal NLRP3 inflammasome activation in AcP-IgAN mice. (16A-D) Detection renal mRNA levels of NLRP3 (16A), caspase-1 (16B), IL-1β (16C), or IL-18 (16D) by real-time PCR. (16E-F) Representative Western blots of NLRP3 (16E) or caspase-1 (Casp1) (16F) in kidney tissues. The appearance of the Casp1 p20 subunit indicates activation. β-actin was used as internal control. *p<0.05, p<0.01, *p<0.005.

FIG. 17A-F show illustrative results from the exemplary cyclohexenone Compound 1 suppressing IL-6 and MCP-1 expression and NF-κB activation in the kidney of AcP-IgAN mice. (17A) Detection of NF-κB p65 by immunohistochemical staining. Original magnification, 400×. The scoring is shown in the lower panel. (17B) Measurement of kidney NF-κB activity using an ELISA-based TransAM NF-κB kit. (17C-D) Detection renal mRNA levels of MCP-1 (17C) and IL-6 (17D) by real-time PCR. (17E-F) Detection renal protein levels of MCP-1 (17E) and IL-6 (17F) by immunohistochemical staining. Original magnification, 400×. The scoring is shown in the lower panels. The data are the mean±SEM for six mice per group. *p<0.05, p<0.01, *p<0.005.

FIG. 18A-B show illustrative results of apoptosis in the kidney of AcP-IgAN mice. (A) Apoptosis was detected in the kidney by terminal deoxynucleotidyl transferase-mediated dUTP nick-end labeling (TUNEL). Original magnification, 400×. (B) Scoring of apoptosis-positive cells in the kidney. The data are the mean±SEM for six mice per group. *p<0.05, p<0.01, *p<0.005.

DETAILED DESCRIPTION OF THE INVENTION

Figure 9C:
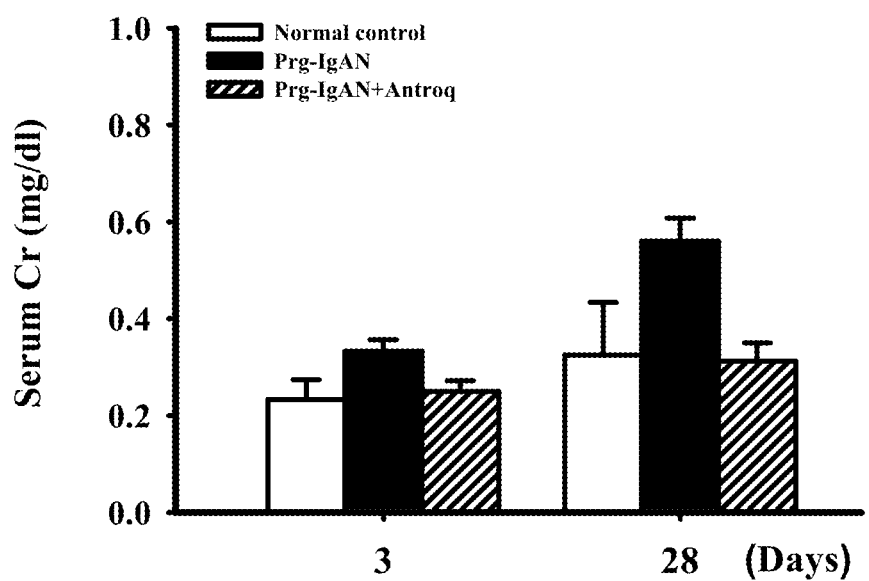

Glomerular diseases include many conditions with a variety of genetic and environmental causes, but they fall into two major categories, Glomerulonephritis and Glomerulosclerosis. Glomerulosclerosis especially FSGS is believed to mainly arise from an intrinsic insult to the glomerular epithelial cell that activates complex interactions within the glomerulus. These complex interactions may include oxidative stress, inflammation with macrophage recruitment, and factors promoting matrix production and/or matrix degradation. High levels of both systemic T cell activation and neutrophil/lymphocyte/macrophage infiltration in the kidney has been increasingly implicated in the acceleration and progression of immunoglobulin A nephropathy (IgAN), the most frequent type of primary glomerulonephritis. So far, however, both prevention and treatment for an aggressive and exacerbated stage of IgAN remains largely under investigation. Provided herein are methods for the treatment of kidney disorders, especially glomerulosclerosis or glomerulonephritis by administering a cyclohexenone compound provided herein to a subject (e.g. a human). The cyclohexenone compound provides therapeutic effects to a subject (especially in the kidney) for treating glomerulosclerosis (see Examples 1-6, and 14) and/or glomerulonephritis (see Examples 7-13, and 14).

In some embodiments, there are provided methods for the treatment of glomerular diseases (such as glomerulosclerosis or glomerulonephritis) in a subject. The methods comprise administering to the subject a therapeutically effective amount of a cyclohexenone compound having the structure:

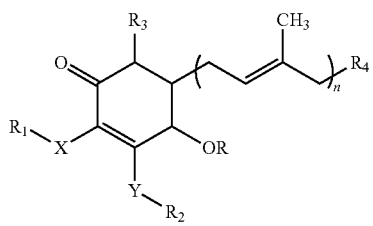

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, there are provided methods for the treatment of glomerulosclerosis. In certain embodiments, glomerulosclerosis is focal segmental glomerulosclerosis (FSGS) or nodular diabetic glomerulosclerosis. In certain embodiments, glomerulosclerosis is focal segmental glomerulosclerosis (FSGS). In some embodiments, the cyclohexenone compound blocks oxidative stress. In certain embodiments, the oxidative stress is blocked by reducing TGF-β1 and extracellular matrix protein expression. In some embodiments, the subject is human. In certain embodiments, the oxidative stress is reduced by enhancing nuclear factor E2-related factor 2 (Nrf2) activity.

In some embodiments, there are provided methods for the treatment of glomerulonephritis. In certain embodiments, glomerulonephritis is immunoglobulin A nephropathy (IgAN). In some embodiments, the cyclohexenone compound reduces CD3$^+$/CD69$^+$ T cells in the subject. In certain embodiments, the cyclohexenone compound reduces proinflammatory cytokines in the subject. In certain embodiments, the pro-inflammatory cytokines comprise MCP-1, IL-6, IL-1β, IL-18, or combinations thereof. In some embodiments, the subject is human.

In some embodiments, the cyclohexenone compound having the structure

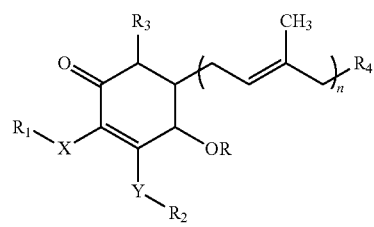

is prepared synthetically or semi-synthetically from any suitable starting material. In other embodiments, the cyclohexenone compound is prepared by fermentation, or the like. For example, Compound 1 (also known as Antroquinonol® or "Antroq") or Compound 3, in some instances, is prepared from 4-hydroxy-2,3-dimethoxy-6-methylcyclohexa-2,5-dienone. The non-limited exemplary compounds are illustrated below.

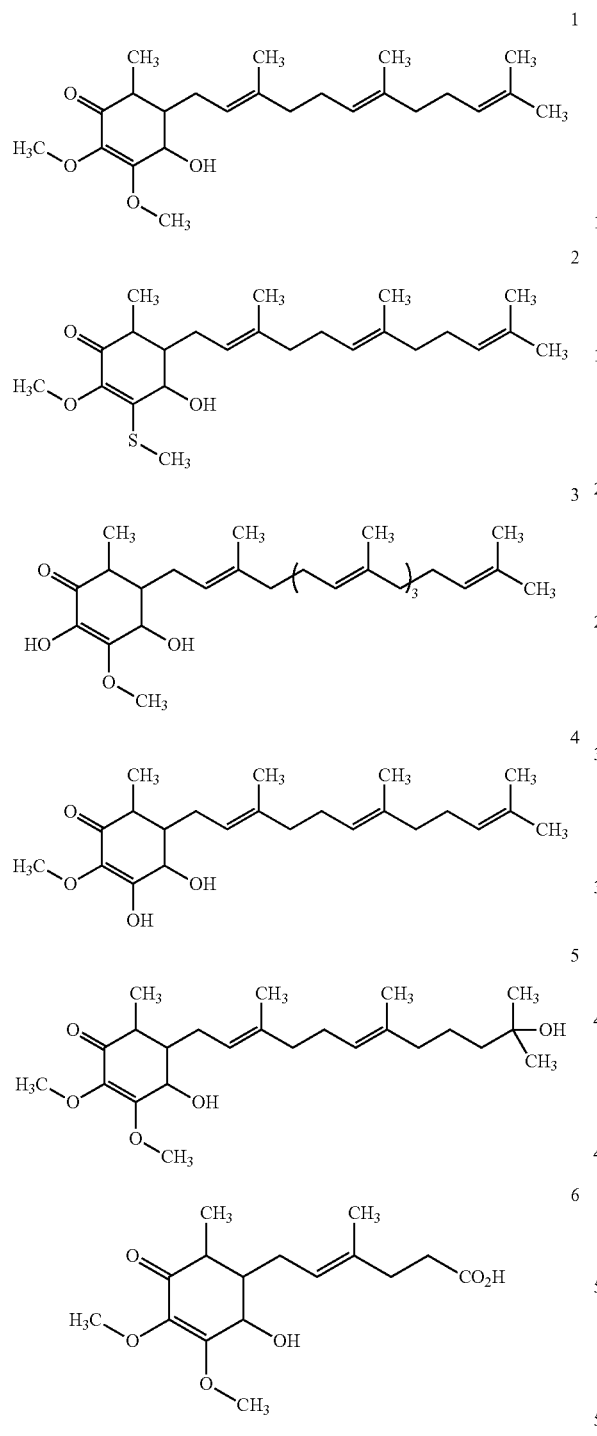
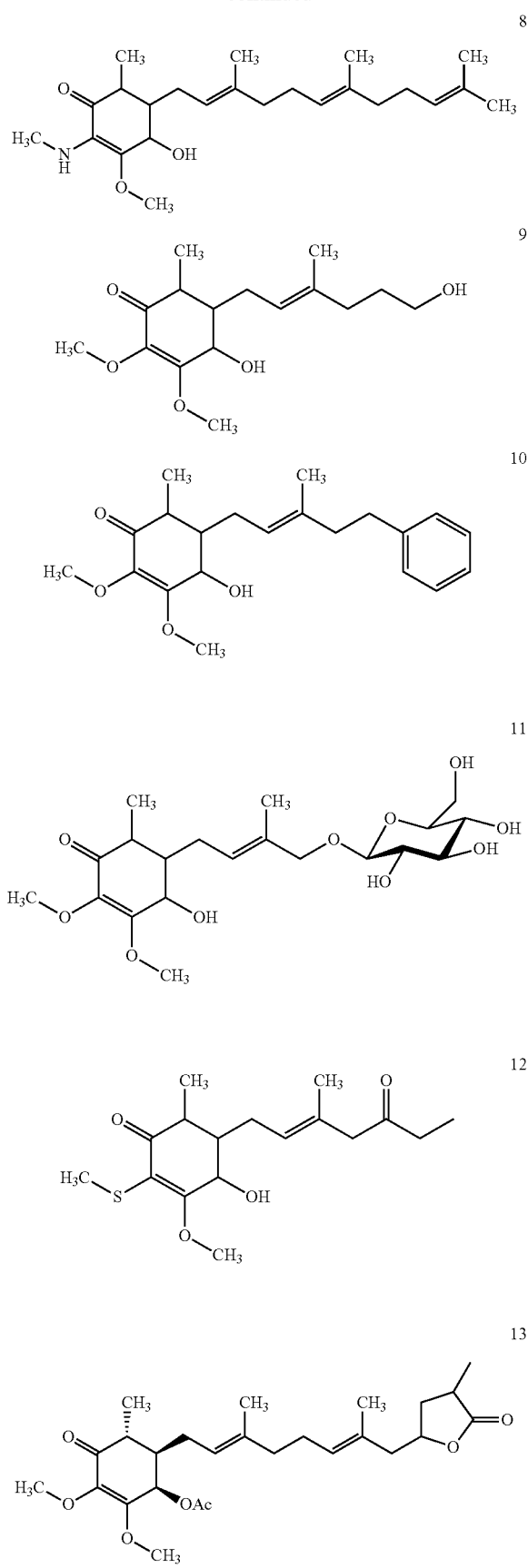

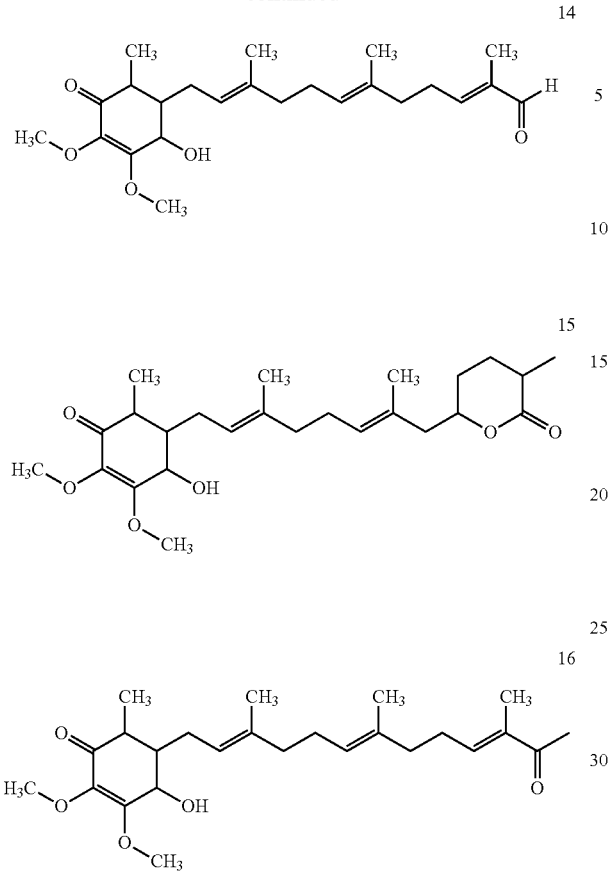

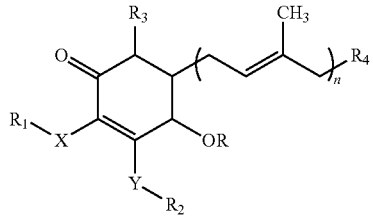

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the glomerular lesions comprise epithelial hyperplasia lesion (EPHL).

In some embodiments, the subject is human.

In some embodiments, the cyclohexenone compounds provided herein possess the therapeutic effects of enhancing nuclear factor E2-related factor 2 (Nrf2) activity but suppressing NF-κB-dependent inflammatory and TGF-β1-mediated fibrosis pathways in the kidney. See Examples 5, 6 and 14.

In some embodiments provide methods for enhancing renal nuclear factor E2-related factor 2 (Nrf2) activity in a subject comprising administering to the subject an effective amount of a cyclohexenone compound having the structure:

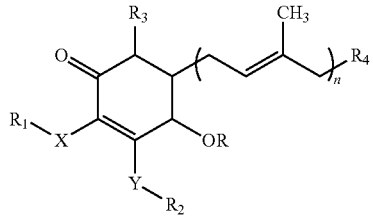

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents In other embodiments, the cyclohexenone compound having the structure

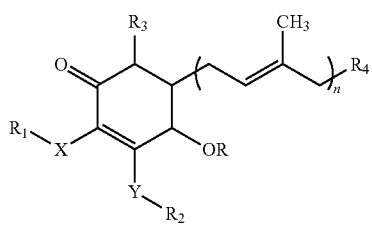

is isolated from the organic solvent extracts of *Antrodia camphorate*. In some embodiments, the organic solvent is selected from alcohols (e.g., methanol, ethanol, propanol, or the like), esters (e.g., methyl acetate, ethyl acetate, or the like), alkanes (e.g., pentane, hexane, heptane, or the like), halogenated alkanes (e.g., chloromethane, chloroethane, chloroform, methylene chloride, and the like), and the like. For example, exemplary Compounds 1-7 are isolated from organic solvent extracts. In certain embodiments, the organic solvent is alcohol. In certain embodiments, the alcohol is ethanol. In some embodiments, the cyclohexenone compound is isolated from the aqueous extracts of *Antrodia camphorata*.

In some embodiments, there are provided methods for attenuating renal dysfunction or glomerular lesions in a subject comprising administering to the subject an effective amount of a cyclohexenone compound having the structure:

selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the subject is human.

In some embodiments provide methods for inhibiting renal NF-κB activation and/or transforming growth factor (TGF)-β1 protein expression in a subject comprising administering to the subject an effective amount of a cyclohexenone compound having the structure:

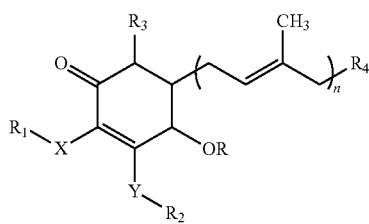

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the subject is human.

In some embodiments, administration of the cyclohexenone compound provided herein (e.g., Compound 1) inhibits ROS/NO and $p47^{phox}$ NAD(P)H oxidase production in the kidney, but clearly enhances Nrf2 signaling pathway responsible for the effects of the cyclohexenone compound on the FSGS subject. See Examples 3, 5 and 14.

In some embodiments provide methods for inhibiting ROS/NO and/or $p47^{phox}$ in a subject comprising administering to the subject an effective amount of a cyclohexenone compound having the structure:

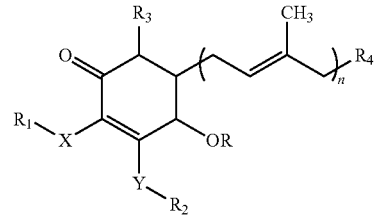

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the subject is human.

In some embodiments provide methods for reducing $CD3^+/CD69^+$ T cells in a subject comprising administering to the subject an effective amount of a cyclohexenone compound having the structure:

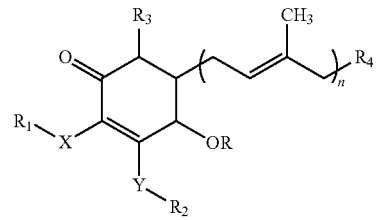

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

In some embodiments, the subject is human.

It was observed that the control FSGS mice showed significantly enhanced GPx activity on day 7 after the disease induction (Examples 4 and 14). Oxidative stress and its constant companion inflammation are also common features of chronic kidney disease (Kim, et al., *Am J Physiol Renal Physiol*, 298: F662-671, 2010; Yoon, et al., *Kidney Int*, 71: 167-172, 2007) and play a critical part in progression of glomerularsclerosis. Of note, oxidative stress and inflammation are intimately related as each of them recruits and amplifies the other to trigger a vicious cycle. For instance, oxidative stress can induce inflammation by activating NF-κB and subsequent production of pro-inflammatory cytokines and chemokines whereby leading to leukocyte activation and production and releasing ROS/NO, while these events promote oxidative stress in return. (Anrather, et al., *J Biol Chem*, 281: 5657-5667, 2006; Vaziri, et al., *Nat Clin Pract Nephrol*, 2: 582-593, 2006; Rodrigo, et al., *Free Radic Biol Med*, 33: 409-422, 2002) In addition, the inflammatory response to activation of NF-κB and consequent induction of cyclooxygenase-2, inducible nitric oxide synthase, IL-6, and TNF-α is more intense in Nrf2 knockout mice compared with the wild type mice (Chen, et al., *Am J Physiol Heart Circ Physiol*, 290: H1862-1870, 2006; Li, et al., *Biochem Pharmacol*, 76: 1485-1489, 2008) It also has been reported that deficiency of HO-1, which is regulated by Nrf2, has been shown to accentuate glomerulonephritis. (Datta, et al., *J Am Soc Nephrol*, 10: 2540-2550, 1999)

In some embodiments, administration of the cyclohexenone compound provided herein (e.g., Compound 1) significantly reduces renal IL-6 expression and blocks NF-κB activation in the kidney. This was confirmed by significantly inhibited infiltration of T cells and macrophages into the kidney in the FSGS+Antroq mice. (Examples 5, 11 and 14) In some embodiments, the effect is a mechanism responsible for preventing interstitial inflammation and EPHLs, the latter being a key index for the renal progression of FSGS. (D'Agati, V *Semin Nephrol*, 23: 117-134, 2003; Nagata, et al., *Lab Invest*, 80: 869-880, 2000)

In some embodiments provide methods for enhancing glutathione peroxidase (GPx) activity in the kidney comprising administering to a subject an effective amount of a cyclohexenone compound having the structure:

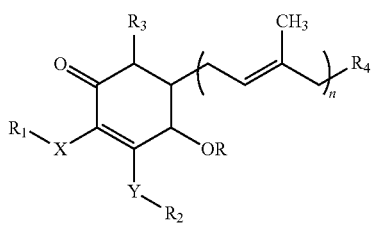

wherein each of X and Y independently is oxygen, $NR_5$ or sulfur;
R is a hydrogen or C(=O)$C_1$-$C_8$alkyl;
each of $R_1$, $R_2$ and $R_3$ independently is a hydrogen, methyl or $(CH_2)_m$—$CH_3$;
$R_4$ is $NR_5R_6$, $OR_5$, OC(=O)$R_7$, C(=O)$OR_5$, C(=O)$R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, OC(=O)$R_7$, C(=O)$OR_5$, C(=O)$R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

In some embodiments, the subject is human.

In some embodiments provide methods for reducing pro-inflammatory cytokines in a subject comprising administering to the subject an effective amount of a cyclohexenone compound having the structure

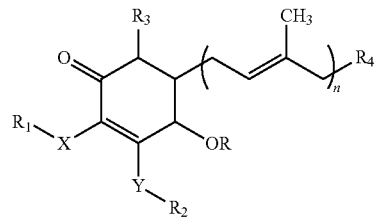

wherein each of X and Y independently is oxygen, $NR_5$ or sulfur;
R is a hydrogen or C(=O)$C_1$-$C_8$alkyl;
each of $R_1$, $R_2$ and $R_3$ independently is a hydrogen, methyl or $(CH_2)_m$—$CH_3$;
$R_4$ is $NR_5R_6$, $OR_5$, OC(=O)$R_7$, C(=O)$OR_5$, C(=O)$R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, OC(=O)$R_7$, C(=O)$OR_5$, C(=O)$R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

In certain embodiments, the pro-inflammatory cytokines comprise MCP-1, IL-6, IL-1β, IL-18, or combinations thereof. In some embodiments, the subject is human.

In some embodiments provide methods for reducing renal caspase-1 protein expression and/or inhibiting renal NLRP3 activation in the kidney comprising administering to a subject an effective amount of a cyclohexenone compound having the structure:

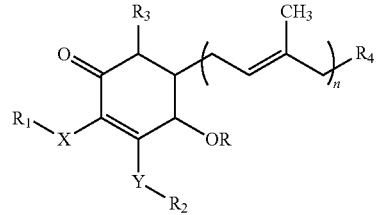

wherein each of X and Y independently is oxygen, $NR_5$ or sulfur;

R is a hydrogen or $C(=O)C_1-C_8$alkyl;

each of $R_1$, $R_2$ and $R_3$ independently is a hydrogen, methyl or $(CH_2)_m-CH_3$;

$R_4$ is $NR_5R_6$, $OR_5$, $OC(=O)R_7$, $C(=O)OR_5$, $C(=O)R_5$, halogen, 5 or 6-membered lactone, $C_1-C_8$alkyl, $C_2-C_8$alkenyl, $C_2-C_8$alkynyl, aryl, glucosyl, wherein the 5 or 6-membered lactone, $C_1-C_8$alkyl, $C_2-C_8$alkenyl, $C_2-C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1-C_8$ alkyl, $C_2-C_8$ alkenyl, $C_2-C_8$ alkynyl, $C_3-C_8$ cycloalkyl, $C_1-C_8$ haloalkyl, and $C_1-C_8$ alkoxy;

each of $R_5$ and $R_6$ is independently a hydrogen or $C_1-C_8$alkyl;

$R_7$ is a $C_1-C_8$alkyl, $OR_5$ or $NR_5R_6$;

m=1-12; and n=1-12; or a pharmaceutically acceptable salt, metabolite, solvate or prodrug thereof.

The subject, in some embodiments, is human.

In some embodiments provide methods for reducing renal NF-κB activation in the kidney comprising administering to a subject an effective amount of a cyclohexenone compound having the structure:

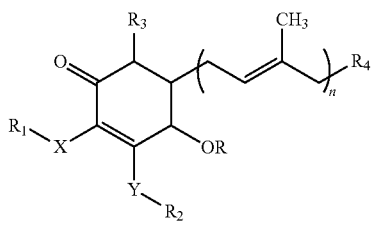

wherein each of X and Y independently is oxygen, $NR_5$ or sulfur;

R is a hydrogen or $C(=O)C_1-C_8$alkyl;

each of $R_1$, $R_2$ and $R_3$ independently is a hydrogen, methyl or $(CH_2)_m-CH_3$;

$R_4$ is $NR_5R_6$, $OR_5$, $OC(=O)R_7$, $C(=O)OR_5$, $C(=O)R_5$, halogen, 5 or 6-membered lactone, $C_1-C_8$alkyl, $C_2-C_8$alkenyl, $C_2-C_8$alkynyl, aryl, glucosyl, wherein the 5 or 6-membered lactone, $C_1-C_8$alkyl, $C_2-C_8$alkenyl, $C_2-C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1-C_8$ alkyl, $C_2-C_8$ alkenyl, $C_2-C_8$ alkynyl, $C_3-C_8$ cycloalkyl, $C_1-C_8$ haloalkyl, and $C_1-C_8$ alkoxy;

each of $R_5$ and $R_6$ is independently a hydrogen or $C_1-C_8$alkyl;

$R_7$ is a $C_1-C_8$alkyl, $OR_5$ or $NR_5R_6$;

m=1-12; and n=1-12; or a pharmaceutically acceptable salt, metabolite, solvate or prodrug thereof.

In some embodiments, the subject is human.

In some embodiments, there are provided methods for inhibiting apoptosis in the kidney comprising administering to a subject an effective amount of a cyclohexenone compound having the structure:

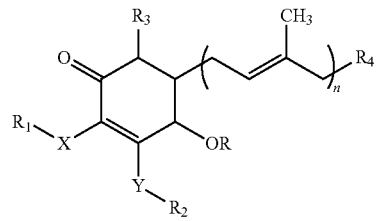

wherein each of X and Y independently is oxygen, $NR_5$ or sulfur;

R is a hydrogen or $C(=O)C_1-C_8$alkyl;

each of $R_1$, $R_2$ and $R_3$ independently is a hydrogen, methyl or $(CH_2)_m-CH_3$;

$R_4$ is $NR_5R_6$, $OR_5$, $OC(=O)R_7$, $C(=O)OR_5$, $C(=O)R_5$, halogen, 5 or 6-membered lactone, $C_1-C_8$alkyl, $C_2-C_8$alkenyl, $C_2-C_8$alkynyl, aryl, glucosyl, wherein the 5 or 6-membered lactone, $C_1-C_8$alkyl, $C_2-C_8$alkenyl, $C_2-C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1-C_8$ alkyl, $C_2-C_8$ alkenyl, $C_2-C_8$ alkynyl, $C_3-C_8$ cycloalkyl, $C_1-C_8$ haloalkyl, and $C_1-C_8$ alkoxy;

each of $R_5$ and $R_6$ is independently a hydrogen or $C_1-C_8$alkyl;

$R_7$ is a $C_1-C_8$alkyl, $OR_5$ or $NR_5R_6$;

m=1-12; and n=1-12; or a pharmaceutically acceptable salt, metabolite, solvate or prodrug thereof.

The subject in some instances is human.

In some embodiments, there are provided methods for protecting or preventing kidney from glomerulosclerosis and/or interstitial fibrosis and/or glomerulonephritis in a subject comprising administering to the subject an effective amount of a cyclohexenone compound having the structure

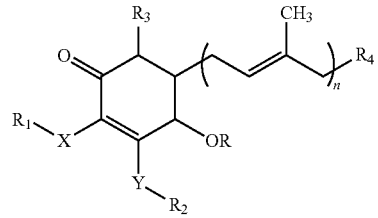

which decreases the expression levels of TGF-β1 protein and collagen I, III and IV protein accumulations in the kidney, wherein each of X and Y independently is oxygen, $NR_5$ or sulfur;

R is a hydrogen or $C(=O)C_1-C_8$alkyl;

each of $R_1$, $R_2$ and $R_3$ independently is a hydrogen, methyl or $(CH_2)_m-CH_3$;

$R_4$ is $NR_5R_6$, $OR_5$, $OC(=O)R_7$, $C(=O)OR_5$, $C(=O)R_5$, halogen, 5 or 6-membered lactone, $C_1-C_8$alkyl, $C_2-C_8$alkenyl, $C_2-C_8$alkynyl, aryl, glucosyl, wherein the 5 or 6-membered lactone, $C_1-C_8$alkyl, $C_2-C_8$alkenyl, $C_2-C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1-C_8$ alkyl, $C_2-C_8$ alkenyl, $C_2-C_8$ alkynyl, $C_3-C_8$ cycloalkyl, $C_1-C_8$ haloalkyl, and $C_1-C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the subject is human.

Oxidative stress caused by combination of increased production of reactive oxygen species (ROS) and/or nitric oxide (NO) and impaired antioxidant capacity, leads to promote necrosis, apoptosis, inflammation, fibrosis, and other disorders of kidney. (See for example, Kim, et al., *Am J Physiol Renal Physiol*, 298: F662-671, 2010) Recent advance in the dissection of renal fibrosis/sclerosis mechanisms has provided evidence that NAD(P)H oxidase enzyme complex of infiltrating leukocytes and intrinsic renal cells plays an important role in the production of superoxide in renal lesions. (MID; Jones, et al., *J Am Soc Nephrol*, 5: 1483-1491, 1995; Radeke, et al., *J Biol Chem*, 266: 21025-21029, 1991) Blockade of oxidative stress can ameliorate renal sclerosis through anti-inflammatory and anti-apoptosis process. Besides, nuclear factor E2-related factor 2 (Nrf2) is found to be a critical transcription factor that binds to the antioxidant response element in the promoter region of a number of genes encoding numerous antioxidant and phase 2 enzymes, such as glutathione peroxidase (GPx), catalase, and superoxide dismutase, in several types of cells and tissues. (Itoh, et al., *Biochem Biophys Res Commun*, 236: 313-322, 1997; Nguyen, et al., *J Biol Chem*, 284: 13291-13295, 2009) The Nrf2-mediated regulation of cellular antioxidant production and anti-inflammatory machinery play an important role against oxidative stress, and Nrf2 signaling pathway has been demonstrated to play a protective role against renal fibrosis in rat tubular epithelial cells (Shin, et al., *Free Radic Biol Med*, 48: 1051-1063, 2010) and streptozotocin-induced diabetic nephropathy (Jiang, et al., *Diabetes*, 59: 850-860, 2010) via transforming growth factor (TGF)-β1 associated epithelial-mesenchymal transition.

The expression of profibrotic cytokines, particularly TGF-β1 is pivotal determinants for renal sclerosis/fibrosis. (Ka, et al., *J Am Soc Nephrol*, 18: 1777-1788, 2007; Lan, H Y. *Front Biosci*, 13: 4984-4992, 2008; Zhao, et al., *Am J Nephrol*, 28: 548-554, 2008) Blocking of oxidative stress has been reported to ameliorate glomerulosclerosis by reducing TGF-β1 and extracellular matrix proteins expression (Hahn, et al., *Pediatr Nephrol*, 13: 195-198, 1999; Kashihara, et al., *Curr Med Chem*.; Manning, et al., *Am J Nephrol*, 25: 311-317, 2005) Also, anti-oxidative stress signaling pathway involving Nrf2 transcription factor and its related phase II enzymes has been shown to play a renal protective role against fibrosis in rat tubular epithelial and streptozotocin-induced diabetic nephropathy.

In some embodiments, treatment with the cyclohexenone compound provided herein (e.g., Compound 1) decreases the expression levels of TGF-β1 protein and its downstream collagen I, III, and IV protein accumulations in the kidney (Examples 6 and 14); this suggests the cyclohexenone compound provided herein is able to protect kidney from glomerulosclerosis and interstitial fibrosis as shown in the treated FSGS mice by blocking TGF-β1-mediated fibrosis pathway.

In some embodiments provide methods for the treatment of focal segmental glomerulosclerosis (FSGS), which comprises administering to a subject an effective amount of a cyclohexenone compound having the structure

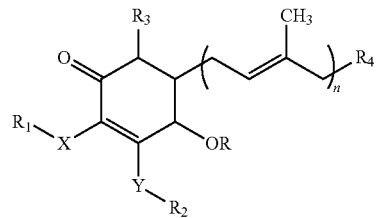

that (i) enhances Nrf2 activity and/or (ii) suppresses NF-κB-dependent inflammatory and TGF-β1-mediated fibrosis in the kidney, wherein each of X and Y independently is oxygen, $NR_5$ or sulfur;

R is a hydrogen or C(=O)$C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, OC(=O)$R_7$, C(=O)$R_7$, C(=O)$OR_5$, C(=O)$R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, OC(=O)$R_7$, C(=O)$OR_5$, C(=O)$R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the subject is human.

In some embodiments provide methods for the treatment of glomerulonephritis in a subject, which comprises administering to the subject an effective amount of a cyclohexenone compound having the structure

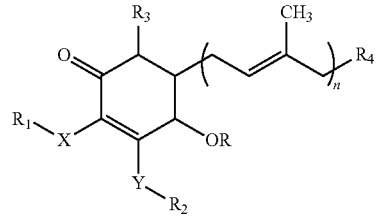

that (i) blocking renal NLRP3 inflammasome activation and/or (ii) inhibiting the increase in T cell activation, wherein each of X and Y independently is oxygen, $NR_5$ or sulfur;

R is a hydrogen or C(=O)$C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, OC(=O)$R_7$, C(=O)$R_7$, C(=O)$OR_5$, C(=O)$R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, OC(=O)$R_7$, C(=O)$OR_5$, C(=O)$R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In accordance with the present invention, the exemplary cyclohexenone Compound 1 altered T cell activity and prevented renal inflammation in the AcP-IgAN mice, the exemplary cyclohexenone compounds are suitable to maintain IgAN in remission.

In certain embodiments, provided herein are methods for maintaining immunoglobulin A nephropathy (IgAN) in remission in a subject, which comprises administering to the subject an effective amount of a cyclohexenone compound having the structure

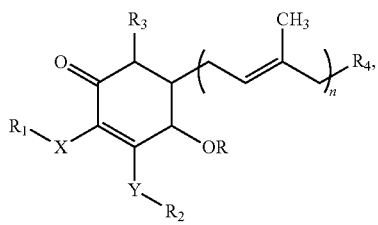

wherein each of X and Y independently is oxygen, $NR_5$ or sulfur;

R is a hydrogen or C(=O)$C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, OC(=O)$R_7$, C(=O)$OR_5$, C(=O)$R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, OC(=O)$R_7$, C(=O)$OR_5$, C(=O)$R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched, or straight chain.

The "alkyl" group may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one, two, three, four, five, or six carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, cyclopropylmethyl, cyclobutylmethyl, cyclopentylmethyl, cyclohexylmethyl, and the like. In one aspect, an alkyl is a $C_1$-$C_6$ alkyl.

The term "alkylene" refers to a divalent alkyl radical. Any of the above mentioned monovalent alkyl groups may be an alkylene by abstraction of a second hydrogen atom from the alkyl. In one aspect, an alkelene is a $C_1$-$C_6$alkylene. In another aspect, an alkylene is a $C_1$-$C_4$alkylene. Typical alkylene groups include, but are not limited to, —$CH_2$—, —CH($CH_3$)—, —C($CH_3$)$_2$—, —$CH_2CH_2$—, —$CH_2$CH($CH_3$)—, —$CH_2$C($CH_3$)$_2$—, —$CH_2CH_2CH_2$—, —$CH_2CH_2CH_2CH_2$—, and the like.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). In one aspect, an arylene is a $C_6$-$C_{10}$ arylene. Exemplary arylenes include, but are not limited to, phenyl-1,2-ene, phenyl-1,3-ene, and phenyl-1,4-ene.

The term "aromatic" refers to a planar ring having a delocalized π-electron system containing 4n+2 π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "halo" or, alternatively, "halogen" or "halide" means fluoro, chloro, bromo or iodo.

The term "lactone" refers to a cyclic ester which can be seen as the condensation product of an alcohol group —OH and a carboxylic acid group —COOH in the same molecule. It is characterized by a closed ring consisting of two or more carbon atoms and a single oxygen atom, with a ketone group =O in one of the carbons adjacent to the other oxygen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (═O) moieties, such as pyrrolidin-2-one.

Combination Treatments

In general, the compositions described herein and, in embodiments where combinational therapy is employed, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

Combinations of compounds (i.e., the cyclohexenone compound described herein) with other sterols and/or immunosuppressives are intended to be covered. In some embodiments, examples of immunosuppressives include, but are not limited to, the following: glucocorticoids, cytostatics, antibodies, drugs acting on immunophilins, and other drugs such as interferons, opioids, TNF binding proteins and mycophenolate.

In some embodiments provide a composition for early treatment of kidney disorders (such as glomerulonephritis, glomerulosclerosis, and the like) comprising an effective amount of a cyclohexenone compound having the structure:

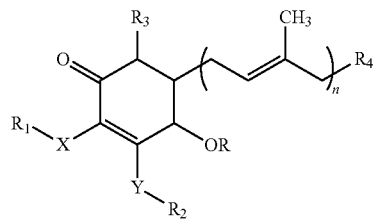

and one or more sterols and/or immunosuppressives, wherein each of X and Y independently is oxygen, $NR_5$ or sulfur; R is a hydrogen or $C(═O)C_1-C_8$alkyl; each of $R_1$, $R_2$ and $R_3$ independently is a hydrogen, methyl or $(CH_2)_m$—$CH_3$; $R_4$ is $NR_5R_6$, $OR_5$, $OC(═O)R_7$, $C(═O)OR_5$, $C(═O)R_5$, halogen, 5 or 6-membered lactone, $C_1-C_8$alkyl, $C_2-C_8$alkenyl, $C_2-C_8$alkynyl, aryl, glucosyl, wherein the 5 or 6-membered lactone, $C_1-C_8$alkyl, $C_2-C_8$alkenyl, $C_2-C_8$alkynyl, aryl, and glucosyl are optionally substituted with one or more substituents selected from $NR_5R_6$, $OR_5$, $OC(═O)R_7$, $C(═O)OR_5$, $C(═O)R_5$, $C_1-C_8$ alkyl, $C_2-C_8$ alkenyl, $C_2-C_8$ alkynyl, $C_3-C_8$ cycloalkyl, $C_1-C_8$ haloalkyl, and $C_1-C_8$ alkoxy; each of $R_5$ and $R_6$ is independently a hydrogen or $C_r$ $C_8$alkyl; $R_7$ is a $C_1-C_8$alkyl, $OR_5$ or $NR_5R_6$; m=1-12; and n=1-12; or a pharmaceutically acceptable salt, metabolite, solvate or prodrug thereof. In some embodiments, the kidney disorder is glomerulosclerosis (e.g., renal fibrosis or sclerosis in FSGS). In other embodiments, the kidney disorder is glomerulonephritis (e.g., immunoglobulin A nephropathy (IgAN)).

"Glucocorticoids" refers to a class of steroid hormones that bind to the glucocorticoid receptor (GR), which is present in almost every vertebrate animal cell. The name glucocorticoid derives from their role in the regulation of the metabolism of glucose, their synthesis in the adrenal cortex, and their steroidal structure. Examples of glucocorticoids include, but are not limited to, hydrocortisone (Cortisol), cortisone acetate, prednisone, prednisolone, methylprednisolone, dexamethasone, betamethasone, triamcinolone, beclometasone, fludrocortisone acetate, deoxycorticosterone acetate (DOCA), and aldosterone.

Examples of drugs acting on immunophilins include, but not limited to cyclosporin, tacrolimus, voclosporin and other calcineurin inhibitors, and sirolimus.

Certain Pharmaceutical and Medical Terminology

The term "acceptable" with respect to a formulation, composition or ingredient, as used herein, means having no persistent detrimental effect on the general health of the subject being treated.

*Antrodia* is a genus of fungi in the family Meripilaceae. *Antrodia* species have fruiting bodies that typically lie flat or spread out on the growing surface, with the hymenium exposed to the outside; the edges may be turned so as to form narrow brackets. Most species are found in temperate and boreal forests, and cause brown rot. Some of the species in this genus are have medicinal properties, and have been used in Taiwan as a Traditional medicine.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound (i.e., a cyclohexenone compound described herein) and a co-agent, are both administered to a patient simultaneously in the form of a single entity or dosage. The term "non-fixed combination" means that the active ingredients, e.g. a compound (i.e., a cyclohexenone compound described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., a cyclohexenone compound described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Composition/Formulation

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: *The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

Provided herein are pharmaceutical compositions comprising a compound (i.e., a cyclohexenone compound described herein) and a pharmaceutically acceptable diluent(s), excipient(s), or carrier(s). In certain embodiments, the compounds described are administered as pharmaceutical compositions in which a compound (i.e., a cyclohexenone compound described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., a cyclohexenone compound described herein).

A pharmaceutical composition, as used herein, refers to a mixture of a compound (i.e., a cyclohexenone compound described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., a cyclohexenone compound described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., a cyclohexenone compound described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., a cyclohexenone compound described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound (i.e., a cyclohexenone compound described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., a cyclohexenone compound described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., cyclohexenone compounds described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., a cyclohexenone compound described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL, 0.6 mL, 1.0 mL or other suitable volume of solution at about a concentration of 0.5 mg to 50 mg of a compound (i.e., a cyclohexenone compound described herein) per 1 mL of solution. Each injector is capable of delivering only one dose of the compound.

In still other embodiments, the compounds (i.e., cyclohexenone compounds described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds (i.e., cyclohexenone compounds described herein) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound (i.e., a cyclohexenone compound described herein) is accomplished by means of iontophoretic patches and the like. In certain embodiments, transdermal patches provide controlled delivery of a compound (i.e., a cyclohexenone compound described herein). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound (i.e., a cyclohexenone compound described herein); (2) a penetration enhancer; and (3) an aqueous adjuvant. In addition, transdermal formulations can include additional components such as, but not limited to, gelling agents, creams and ointment bases, and the like. In some embodiments, the transdermal formulations further include a woven or nonwoven backing material to enhance absorption and prevent the removal of the transdermal formulation from the skin. In other embodiments, the transdermal formulations described herein maintain a saturated or supersaturated state to promote diffusion into the skin.

In other embodiments, the compounds (i.e., cyclohexenone compounds described herein) are formulated for administration by inhalation. Various forms suitable for administration by inhalation include, but are not limited to, aerosols, mists or powders. Pharmaceutical compositions of a compound (i.e., a cyclohexenone compound described herein) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatins for use in an inhaler or insufflator are formulated containing a powder mix of the compound and a suitable powder base such as lactose or starch.

Intranasal formulations are known in the art and are described in, for example, U.S. Pat. Nos. 4,476,116, 5,116,817 and 6,391,452, each of which is specifically incorporated herein by reference. Formulations, which include a compound (i.e., a cyclohexenone compound described herein), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are found in sources such as REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein, may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

In still other embodiments, the compounds (i.e., cyclohexenone compounds described herein) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., a cyclohexenone compound described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., cyclohexenone compounds described herein) described herein as an active ingredient. The active ingredient is in free-acid or free-base form, or in a pharmaceutically acceptable salt form. In addition, the methods and pharmaceutical compositions described herein include the use crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., cyclohexenone compounds described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., cyclohexenone compounds described herein). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

EXAMPLE

Example 1

Preparation of the Exemplary Compound 1

The exemplary Compound 1 (i.e., Antroq) was isolated from the solid-state fermented mycelium of *Antrodia camphorata* followed the known method. (Lee, et al., *Planta Med*, 73: 1412-1415, 2007) Compound 1 is effective at a range of 10-50 mg/kg body weight, based on a previous study and empirical use. (Chang, et al., *Evid Based Complement Alternat Med*, 2008) Unless indicating otherwise, 50 mg/kg body weight of Compound 1 was used as a dosage in the following experiments.

Alternatively, the exemplary Compound 1 may be prepared from 4-hydroxy-2,3-dimethoxy-6-methylcyclohexa-2,5-dienone or the like. Similarly, other cyclohexenone compounds having the structure

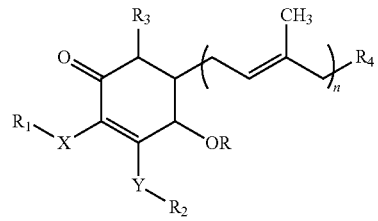

are isolated from *Antrodia camphorata* or prepared synthetically or semi-synthetically from the appropriate starting materials. An ordinary skilled in the art would readily utilize appropriate conditions for such synthesis.

Example 2

Establishment of the FSGS Model and Experimental Protocol

Experiments described herein were performed on 8-week-old female BALB/c mice. The FSGS mice were injected intravenously with a single dose of adriamycin (0.1 mg/10 g body weight). The mice were given Compound 1 six hours before adriamycin injection by gavage daily till sacrifice. BALB/c mice intraperitoneal injected with normal saline were used as normal controls, while ASLN mice given vehicle (corn oil) by gavage were used as disease controls. Mice were killed at day 7, 14, or 21 after disease induction, and spleen, renal cortical tissue, and blood samples collected and stored appropriately until analysis. All animal experiments were performed with the ethical approval of the Institutional Animal Care and Use Committee of The National Defense Medical Center, Taiwan and performed according to the ethical rules in the NIH Guide for the Care and Use of Laboratory Animals.

Clinical and Renal Function Evaluation

Urine samples were collected in metabolic cages at day 3, 7, 14, and 21, and urine protein was determined as described previously. (Shui, et al., *Nephrol Dial Transplant*, 21: 1794-1802, 2006) Serum samples were collected at day 7, 14, or 21 when mice were sacrificed to measure serum levels of BUN and Cr.

Pathologic Evaluation

Formalin-fixed and paraffin-embedded renal sections were prepared as described in Shui et al. for renal pathologic evaluation. (Shui, et al., *Transl Res*, 150: 216-222, 2007) Renal pathology and scoring of renal lesions were performed according to the known method disclosed in Shui. For evaluations of EPHL and sclerosis, at least 50 glomeruli in renal tissue sections for each case were examined. The number of glomeruli with EPHLs was expressed as a percentage of the total number of evaluated glomeruli according to methods disclosed before (see for example, Shui, et al., *Nephrol Dial Transplant*, 21: 1794-1802, 2006; Ka, et al., *Nephrol Dial Transplant*, 21: 288-298, 2006).

For IHC, formalin-fixed and paraffin-embedded renal sections were prepared and incubated with primary antibodies against mouse Desmin (Lab Vision, CA, USA), CD3 (pan-T cell; Serotec, N.C., USA), F4/80 (monocytes/macrophages; Serotec), IL-6 (R&D Systems, MN, USA), NF-κB p65 (Cell Signaling Technology, MA, USA), collagen I, III, and IV (Southern Biotech, AL, USA), or TGF-β1 (Santa Cruz Biotechnology, CA, USA), biotinylated second antibodies (Dako, Glostrup, Denmark), and avidin-biotin-peroxidase complex (Dako). Semi-quantitative evaluation of staining was performed.

Example 3

ROS and NO Determination

Kidney in-situ superoxide anion production was determined by DHE labeling according to the known method. (Wu, et al., *Nephrol Dial Transplant*, 2008, 23: 3082-3090, or Ka, et al., *J. Am. Soc. Nephrol.* 2007, 18:2473-2485) Fluorescent images were quantified by counting the percentage of positive nuclei in the total nuclei per kidney cross section. Sera and kidney tissues were assessed for superoxide anion according to the known method. (Wu, et al., *J Pineal Res*, 2001, 30: 147-156, or Ka, et al., *J. Am. Soc. Nephrol.* 2007, 18:2473-2485) For ROS levels of serum, urine, and renal tissue, the samples were incubated with Krebs-HEPES buffer, and lucigenin (Sigma-Aldrich Chemical Co, MO) at 1.25 mM was used as substrate. Luminescence counts were obtained in duplicate at 15 sec intervals by a microplate luminometer (Hidex Microplate Luminometer, Finland), as previously described (Kretzler, et al.,. *Virchows Arch*, 425: 181-193, 1994). The superoxide anion activity was expressed as relative luminescence units (RLU) per 15 min per mg of organ dry weight (i.e., RUL/15 min/mg) or RLU/15 min/ml.

NO levels in serum were detected with NO Detection kit (iNtRON Biotechnology, Seongnam, Korea), based on diazotization (Griess method), according to the manufacturer's instructions.

Example 4

Measurement of Cellular GPx Activity in the Kidney

GPx activity in renal tissues was measured using a commercial Glutathione Peroxidase Assay kit (Cayman, Mich., USA) according to the manufacturer's instructions Enzyme activity was expressed relative to the protein concentration of glomerular homogenates.

Example 5

Western Blot Analysis of Nrf2 and p47$^{phox}$

The preparation of cytoplasmic and nuclear proteins of renal tissues was extracted using the Nuclear Extract Kit (Active Motif, Tokyo, Japan) according to the manufacturer's instructions. Target proteins in the cytoplasmic and/or nuclear fractions of kidney tissue were measured by Western blot analysis using rabbit antibodies against mouse Nrf2, or p47$^{phox}$ (Santa Cruz). Antibodies to histone H3 (Cell Signaling, CO, USA) and β-actin (Santa Cruz) were used for measuring the housekeeping proteins for nuclear and cytosolic target proteins, respectively.

Example 6

Measurement of TGF-β1

The TGF-β1 protein levels in serum and renal tissue were measured using the commercial ELISA kits (R&D Systems), according to the manufacturer's instructions. Samples were acidified with 1 N HCl and neutralized with 1.2 N NaOH/0.5 M HEPES to assay for the amount of TGF-β1.

Example 7

AcP-IgAN Model in B Cell-deficient Mice

B cell-deficient mice (B6.129S2-Igh-6tm1Cgn/J) were obtained from the Academia Sinica (Professor John T. Kung, Institute of Molecular Biology), and maintained at the animal center of the National Defense Medical Center, Taipei, Taiwan. AcP-IgAN was induced in the mice by daily injection of purified IgA anti-phosphorylcholine antibodies and pneumococcal C-polysaccharide (PnC) as described previously (Chao, et al., *Kidney Int.* 70:283-297; 2006). All animal experiments were performed with the approval of the Institutional Animal Care and Use Committee of The National Defense Medical Center, Taiwan, and were consistent with the NIH *Guide for the Care and Use of Laboratory Animals*.

Clinical and Pathological Evaluation

Body weight of the mice was measured weekly. Urine samples were collected in metabolic cages weekly, and urine protein determined followed the know methods (Chao, et al., *Kidney Int.* 70:283-297; 2006). Serum samples were collected at day 3 and day 28 to measure serum levels of blood urea nitrogen (BUN) and creatinine (Cr).

For renal histopathology, the tissues were fixed in 10% buffered formalin and embedded in paraffin, and then sections (4 μm) were prepared and stained with hematoxylin and eosin (H&E). The proportion of glomeruli showing proliferation, crescent formation, sclerosis, or peri-glomerular inflammation was counted in 50 randomly sampled glomeruli by light microscopy at the magnification of 400×.

Example 8

Immunofluorescence (IF), Immunohistochemistry (IHC), and Detection of Apoptosis

For IF, frozen renal tissues were prepared as described previously and incubated with fluorescein isothiocyanate (FITC)-conjugated goat anti-mouse IgA or C3 antibodies (Cappel, N.C.). Scoring of staining intensity was performed as described in Chao, et al., *Kidney Int.* 70:283-297 (2006).

For IHC, formalin fixed and paraffin embedded tissue sections or frozen sections were incubated with against IL-6 (R&D Systems, MN), MCP-1 (Santa Cruz, Calif.), F4/80 (monocytes/macrophages; Serotec, N.C.), collagen IV (Southern Biotech, AL), TGF-β1 (Santa Cruz), phopsho-NFκB p65 (Cell Signaling, MA), CD3 (pan-T cell; Serotec), CD4 (T helper cell; BioLegend, CA), CD8 (cytotoxic T cell), CD11b (macrophages/neutrophils), or CD11c (dendritic cells) (BD Biosciences, CA) antibodies. The FITC-conjugated, Alexa Fluor 488-conjugated (Invitrogen, CA) or horseradish peroxidase (HRP) conjugated secondary antibodies (DAKO, Denmark) were then applied to the sections. Hematoxylin or 4',6-diamidino-2-phenylindole (DAKO) was used in the counter staining for nuclei.

For the detection of apoptosis, terminal deoxynucleotidyl transferase-mediated dUTP nick-end labeling (TUNEL) was employed. Formalin-fixed and paraffin-embedded tissue sections were stained with ApopTag plus peroxidase in situ apoptosis detection kit (Chemicon, CA) according to the manufacturer's instructions. For scoring, the cortical renal area (including glomerular and peri-glomerular areas) were examined and expressed as cells/glomerular cross-section.

Example 9

Flow Cytometry

Splenocytes from the mice were treated with Tris-buffered ammonium chloride to eliminate erythrocytes, washed, resuspended in RPMI 1640 supplemented with 10% fetal calf serum, HEPES buffer, L-glutamine, and penicillin/streptomycin (all from Invitrogen). The cells were stained with either surface marker for T or B cell activation. FITC-conjugated anti-mouse CD3, CD4, CD8, or CD19 (B cell) antibodies and phycoerythrin (PE)-conjugated anti-mouse CD69 antibodies (all from BD Biosciences) were analyzed with FACSCalibur (BD Biosciences).

Example 10

T Cell Proliferation Analysis

Splenocytes from the mice were prepared as described as above, then were cultured in triplicate in wells (5×10$^5$ cells in 200 µl/well) in 96-well flat-bottomed microtiter plates previously coated overnight at 4° C. with 0.25 µg/ml of anti-mouse CD3 antibody (BD Biosciences). After 48 hr, the cultures were pulsed with 1 µCi of 3H-methyl thymidine (Amersham Pharmacia Biotech, NJ), harvested 16 hr later, and the incorporated 3H-methyl thymidine measured using a TopCount (Packard, PerkinElmer, MA).

Example 11

Enzyme-linked Immunosorbant Assay (ELISA) of IL-1β, IL-6, IL-18 and MCP-1

Serum levels of IL-1β (eBiosceience, CA), IL-6 (eBiosceience), IL-18 (MBL, Japan), and MCP-1 (eBiosceience) were measured using commercial ELISA kits according to the manufacturer's instructions.

Nuclear proteins were extracted using a nuclear extract kit (Active Motif, Japan). Phospho-NF-κB p65 and nuclear factor-erythroid-2-related factor 2 (NrF2) were measured in renal tissue nuclear protein extracts using Trans-AM ELISA assay kits (Active Motif), according to the manufacturer's instructions. Renal cytosolic protein extracts using RIPA buffer (Cell signaling). Cytosolic glutathione peroxidase (GPx) (Cayman, Mich.) and cytosolic heme oxygenase-1 (HO-1) (Enzo Life Sciences, NY) were measured using commercial ELISA kits according to the manufacturer's instructions. Both were expressed relative to the protein concentration in the lysate.

In all ELISAs, the absorbance at 450 nm was measured using an ELISA plate reader (Bio-Tek, MA).

Example 12

Real-time PCR Analysis

Total cortical kidney RNA was extracted with TriZOL reagents (Invitrogen) from cortical tissue of the kidney. For first-strand cDNA synthesis, 1.5 µg of total RNA was used in a single-round reverse transcriptase reaction. The reaction mixture consisted of 0.9 µl of Oligo (dT) 12 to 18 primer, 1.0 mM deoxyribonucleotide triphosphate (dNTP), 1 µl first strand buffer, 0.4 mM dithiothreitol, 80 U of RNaseout recombinant ribonuclease inhibitor, and 300 U of superscript II RNase H (Invitrogen). Real-time PCR was performed on an ABI Prism 7700 Sequence Detection System (Applied Biosystems, CA). All of the probes and primers were Assays-on-Demand Gene expression products (Applied Biosystems). Real-time PCR reactions were using 10 µl of cDNA, 12.5 µl of TaqMan Universal PCR Master Mix (Applied Biosystems), and 1.25 µl of the specific probe/primer mixed in a total volume of 25 µl. The thermal cycler conditions were as follows: 2 min at 50° C., 10 min at 95° C., 40 cycles of denaturation (15 s at 95° C.), and combined annealing/extension (1 min at 60° C.).

Example 13

Western Blot Analysis

Each protein sample was run on a 10% SDS-PAGE gel. The gel was electroblotted onto polyvinylidene difluoride nitrocellulose membrane (Amersham Int., UK); incubated for 1 h in blocking buffer (Tris-buffered saline that contained 5% skim milk); and incubated with rabbit against nacht domain-, leucine-rich repeat-, and pyrin domain (PYD)-containing protein 3 (NLRP3), caspase-1 or β-actin (all from Santa Cruz) antibodies at 4° C. overnight. After washing, the membrane was incubated with HRP-conjugated goat anti-rabbit (DAKO) antibody for 1 h at room temperature. The membrane-bound antibody detected was incubated with chemiluminescent reagent plus (PerkinElmer Life Sciences, MA) and captured on x-ray film.

Example 14

Data Analysis

The results are presented as the mean±SEM. Comparisons between two groups were performed using Student's t test. Differences among multiple groups were determined with the one-way analysis of variance (ANOVA) using Tukey's method for post hoc analysis. A p value <0.05 was considered statistically significant.

FSGS Model

As a disease control, FSGS mice treated with vehicle (i.e., control FSGS mice) showed increased urine protein levels from day 7 of the treatment and continued to rise up to the end of the study at day 21 (See FIG. 1A). This effect was greatly suppressed in Compound 1 treated FSGS mice (FSGS+Antroq mice) where the urine protein levels were similar to those in normal control mice. In addition, compared to control FSGS mice, which showed a significant and persistent increase serum levels of blood urea nitrogen (BUN) (FIG. 1B) and creatinine (Cr) (FIG. 1C) from day 14 to day 21, FSGS+Antroq (i.e. Compound 1) mice exhibited much better renal function. There was no significant difference in the levels of BUN or Cr levels among the normal control, control FSGS, and FSGS+Antroq mice on day 7.

Histopathological examination was performed on kidney sections at various time-points (FIG. 2A). In control FSGS mice, expansion of the extracellular matrix and deposition of hyaline mass in the glomeruli were occasionally seen on day 7 and these became obvious sclerotic lesions from day 14 to day 21, compared to normal control mice. Importantly, the mice exhibited a significant and steady increase in the percentage of glomeruli containing EPHL and peri-glomerular mononuclear leukocyte infiltration from day 14 to day 21, suggesting a progressive pathological status. In contrast, these progressive renal lesions were greatly reduced in FSGS+Antroq mice. Besides, podocyte injury and loss have been proposed as critical pathogenic events in the development of FSGS. To assess changes in podocyte phenotype during the Antroq treatment of FSGS, we studied the expression of desmin, a podocyte-specific marker by immunohistochemistry (IHC). As shown in FIG. 2B, FSGS+Antroq mice showed significantly reduced expression of desmin compared to control FSGS mice on both days 14 and 21, although mild desmin expression levels were observed compared to normal control mice on day 21.

These results show that the exemplary Compound 1 improves proteinuria, renal function, and renal lesions including epithelial hyperplasia lesion (EPHL), a severe index of glomerular injury.

Systemic Suppression of Oxidative Stress in Serum and Urine

The serum superoxide anion levels were significantly increased in control FSGS mice (FSGS+vehicle) compared with normal control mice on day 7 and day 14, and then slightly dropped on day 21, although still higher than normal control mice. Administration of the exemplary Compound 1 (Antroq) effectively attenuated the levels of superoxide anion to a level similar to that observed in normal control mice from day 7 to day 21 (FIG. 3A). In addition, serum NO levels in control FSGS mice were significantly increased on day 7 and remained high levels on day 14 and day 21. The high serum NO levels were significantly suppressed when the exemplary Compound 1 was administered to the FSGS mice (FSGS+Antroq) (FIG. 3B). The superoxide anion levels in urine significantly increased on day 7 and remained to day 21 in FSGS control mice, compared to normal control mice. In contrast, administration of the exemplary Compound 1 significantly lowered the levels of superoxide anion in FSGS+Antroq mice (FIG. 3C). Although urine NO levels in control FSGS mice were significantly increased from day 14 to day 21, again administration of the exemplary Compound 1 effectively blunted these effects in FSGS+Antroq mice (FIG. 3D). There was no detectable difference in urine levels of NO among normal control, FSGS+vehicle, and FSGS+antroq mice at day 7.

Local Inhibition of ROS Production in Kidney Tissues

As shown in FIG. 3E, the superoxide anion levels in the kidney of control FSGS mice were significantly increased on day 14 and continued to rise up to day 21, compared with normal control mice. Antroq administration effectively attenuated the levels of superoxide anion to a level similar to that observed in normal control mice on both day 14 and day 21.

To further localize ROS production in the kidney, in-situ ROS production in renal tissue was analyzed by using the dihydroethidium (DHE) assay. As shown in FIG. 3F, DHE fluorescence was significantly increased in the kidney, mainly in glomeruli and some renal tubules, of control FSGS mice from day 14 to day 21, showing increased in-situ ROS production compared to normal mice. In contrast, only very low DHE fluorescence was observed in FSGS+Antroq mice at both day 14 and day 21.

Nrf2-mediated Antioxidant Signaling Pathway

NAD(P)H oxidase subunit $p47^{phox}$ protein expression levels, Nrf2 translocation into nuclei (activation), and GPx activity in the kidney were further measured to determine the effects of Antroq on antioxidant signaling pathway.

As shown in FIG. 4A and C, protein levels of NAD(P)H oxidase subunit $p47^{phox}$ were significantly increased in control FSGS mice from day 14 to day 21 and these effects were abolished by administration of Antroq. In contrast, FSGS+Antroq mice showed strongly augmented Nrf2 translocation into nuclei compared to control FSGS mice or normal controls from day 14 and this remained high on day 21 (FIGS. 4B and D).

In addition, as shown in FIG. 4E, marked decreased of activity of GPx, one of the phase II enzymes downstream of Nrf2, was seen in control FSGS mice from day 7 to day 21, compared to normal control mice. However, compared with control FSGS mice, FSGS+Antroq mice showed recovered GPx activity in the kidney on day 7 and maintained until day 21 when the mice were sacrificed.

These results show the exemplary Compound 1 inhibits ROS/NO production, but enhances Nrf2 activation and GPx activity.

T Cell and Macrophage Infiltration

The interstitial recruitment of macrophages and lymphocytes as major source of inflammatory and profibrotic mediators plays an important role in progression of FSGS.[1,38] The effects of administering the exemplary Compound 1 on T cells and/or monocytes/macrophages infiltration in kidney were next assessed. Compared to control FSGS mice which showed that a profound T cells ($CD3^+$) and monocytes/macrophages ($F4/80^+$) infiltration was noted in the periglomerular region of the renal interstitium on day 14 and day 21, FSGS+ Antroq mice showed the similar pattern to normal control mice (FIGS. 5A and B).

IL-6 Production

The production of IL-6 in the kidney was further measured. As shown by IHC in FIG. 6A, the protein expression of IL-6 were significantly increased as early as day 7 and continued to rise up to day 21 till mice were sacrificed. However, FSGS+Antroq mice showed significantly reduced renal protein expression levels of and IL-6, compared with control FSGS mice.

Blocking of NF-κB Activation

The effects of the exemplary Compound 1 administration on NF-κB activation in kidney tissues were investigated. As shown in FIG. 6B, compared to control FSGS mice showed significantly stimulated the nuclear NF-κB p65 expression on day 14 and day 21, NF-κB activation in FSGS+Antroq mice were markedly inhibited. Consistent with the IHC, ELISA assay for renal tissue nuclear protein extracts also demonstrated that nuclear protein expression of NF-κB p65 was tend to increased on day 14 and significantly increased on day 21 in control FSGS mice compared to normal control mice. These effects was slightly blocked by Compound 1 (Antroq) administration on day 14 and significantly inhibited on day 21 in FSGS+Antroq mice. There was no significant difference in either control FSGS mice or FSGS+Antroq mice early on day 7 (FIG. 6C).

Thus, the blocking of NF-κB activation in the kidney provides beneficial effects on inflammation when the cyclohexenone compound provided herein is administered.

The effects of administration of the cyclohexenone compound provided herein on glomerulosclerosis in the FSGS model were further evaluated, focusing on fibrosis related proteins, collagen I, III, and IV. As shown in FIG. 7A-C, IHC demonstrated marked renal expression of collagen I and IV from day 14 to day 21, and collagen III on day 21 in control FSGS mice compared with normal control mice and that Compound 1 administration was associated with significant suppression of the expression of these proteins, their levels in FSGS+Antroq mice not being significantly different from those in normal control mice. TGF-β1 is a fundamental growth factor and cytokine in renal fibrosis and creascent formation. ELISA showed that compared with normal control mice, TGF-β1 protein in serum (FIG. 8A) and kidney tissues (FIG. 8B) were significantly upregulated on day 14 and dramatically increased on day 21 in control FSGS mice. However, administration of the exemplary Compound 1 greatly abrogated the increased TGF-β1 protein levels in both serum and kidney. IHC was further performed to determine the changes in expression levels of TGF-β1 protein in renal tissues. Similarly, FSGS+Antroq mice showed a significantly lower TGF-β1 protein expression in the kidney than control FSGS mice as demonstrated by IHC (FIG. 8C). As such, inhibition of TGF-β1 expression provides the beneficial effects on the treatment of glomerulosclerosis when the cyclohexenone compound provided herein is used.

IgAN Model

Figure 9D:
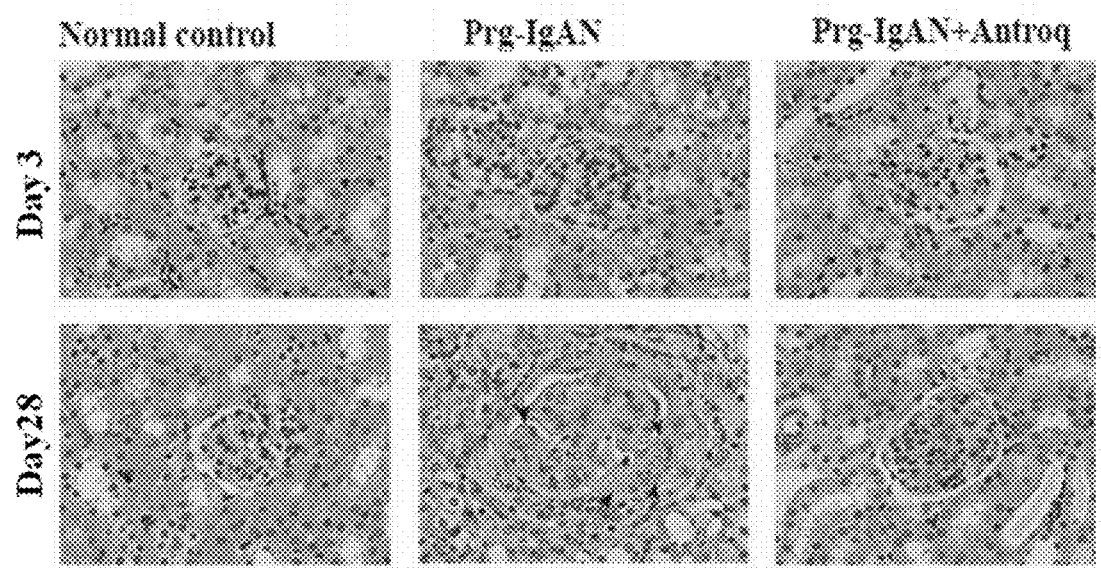
Figure 10C:
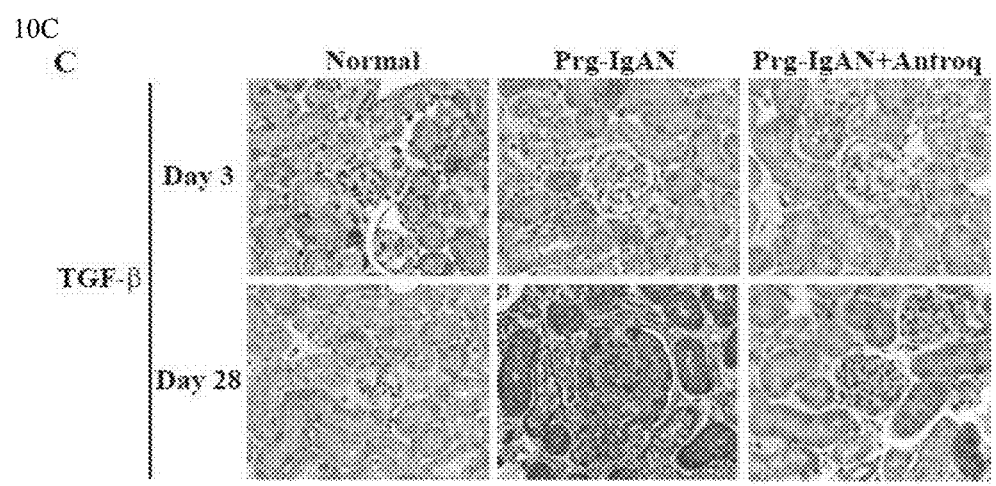
Figure 10D:
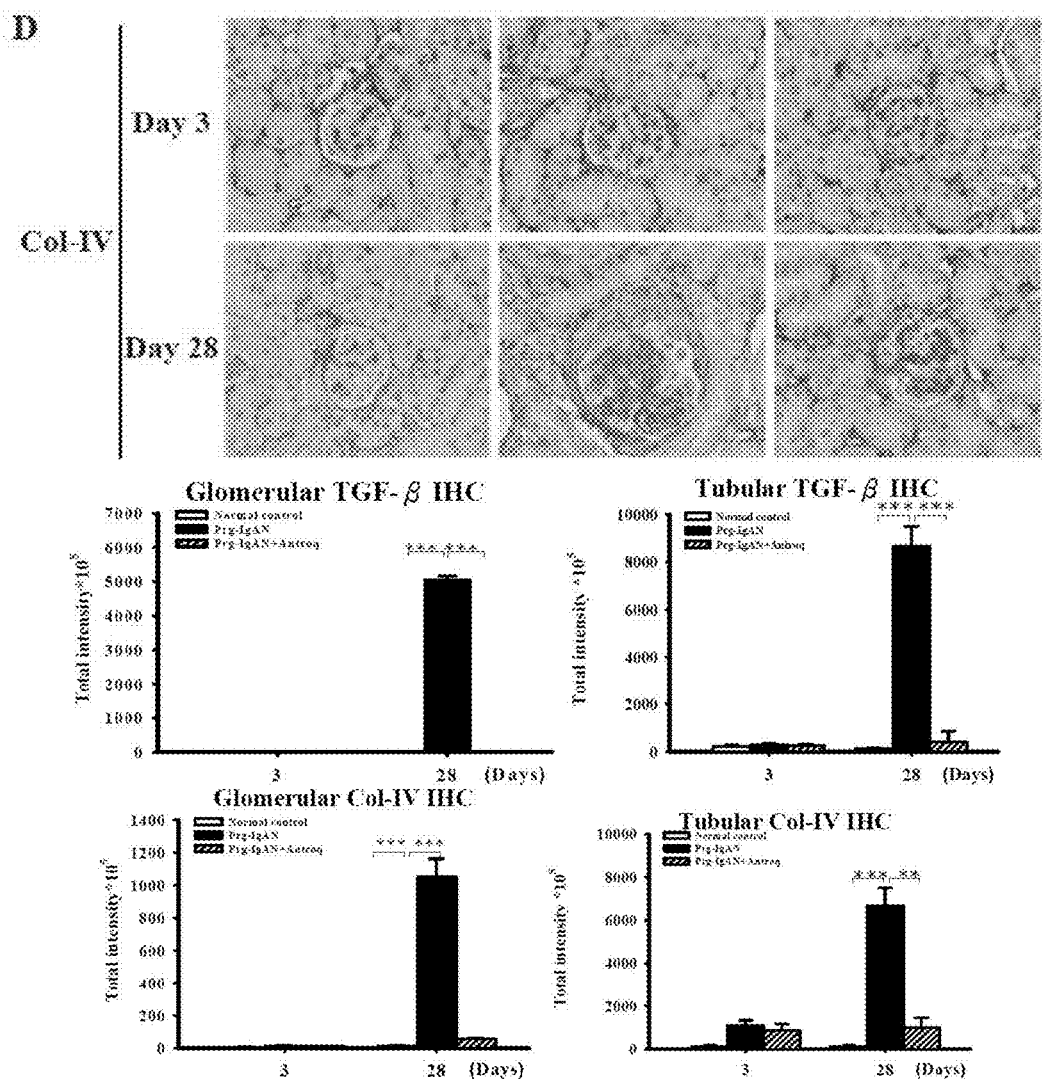

As a disease control, AcP-IgAN mice treated with vehicle (control AcP-IgAN mice) showed increased urine protein levels from day 7 of disease induction and these continued to rise up to the end of the study at day 28 (FIG. 9). This effect was greatly suppressed in AcP-IgAN mice treated with Compound 1 (AcP-IgAN+Antroq mice), although they still showed mild proteinuria compared to normal controls. In addition, compared to control AcP-IgAN mice, which showed significantly increased serum levels of BUN (FIG. 9B) and creatinine (FIG. 9C) at day 28, AcP-IgAN+Antroq mice revealed much better renal function, although there was no significant difference in serum levels of BUN and Cr between control AcP-IgAN, AcP-IgAN+Antroq and normal control mice at day 3.

The body weight of mice was recorded every week. The growth of control AcP-IgAN and AcP-IgAN+Antroq mice was no different from that of normal controls. In addition, all mice of either group showed normal activity and no evidence of hair loss or appetite change.

Renal Pathology

As shown in FIG. 9A-E, at day 28, control AcP-IgAN mice developed a diffuse proliferation associated with neutrophil infiltraiton, focal but typical crescents, and/or segmental sclerosis in the glomerulus, with intense peri-glomerular mononuclear leukocyte infiltration and scattered tubular atrophy associated with protein casts, suggesting an aggressive and exacerbated status of the diseased kidney in comparison with the reported glomerular (Lai, K. N. *Nephron*. 92:263-270 (2002); Lai, et al., *Nephron*. 69:1-8 (1995); Chen, et al., *J. Clin. Lab. Analysis*. 6:35-39 (1992); Kashem, et al., *Kidney Int*. 45: 868-875 (1994)) and interstitial (Falk, et al., *Kidney Int*. 47:177-185 (1995); van Es, et al., *Kidney Int*. 73:1426-1433 (2008); Torres, et al., *Kidney Int*. 73:327-333 (2008); Walsh, et al., *Clin J Am Soc. Nephrol*. 5:425-430 (2010); Fujinaka, et al., *J. Nephrol*. 20:357-363 (2007)) histopathology in the kidney. Except for the renal lesions from the glomerular immune deposits, all of these renal lesions were substantially inhibited in the AcP-IgAN+Antroq mice. At day 3, control AcP-IgAN mice started to develop focal, but this renal histopathology was again significantly inhibited by Compound 1 administration in AcP-IgAN+Antroq mice.

Renal Fibrosis-Related Gene and Protein Expression

Detection of both mRNA and protein levels of TGF-β1 and Col-IV were performed in the mice. Although control AcP-IgAN mice showed greatly enhanced mRNA expression of TGF-β1 and Col-IV, respectively, in the kidney at day 28, compared to normal controls, these two effects were greatly inhibited by Compound 1 administration in AcP-IgAN+Antroq mice (FIG. 10A-D). Only basal mRNA levels of the two fibrosis-related genes were observed in the two groups of mice at day 3. In parallel, both TGF-beta and Col-IV protein levels were greatly increased in control AcP-IgAN mice at day 28, but this effect was substantially inhibited in AcP-IgAN+Antroq mice, as demonstrated by IHC.

Cell Immunity and Renal Inflammation

Figure 11C:
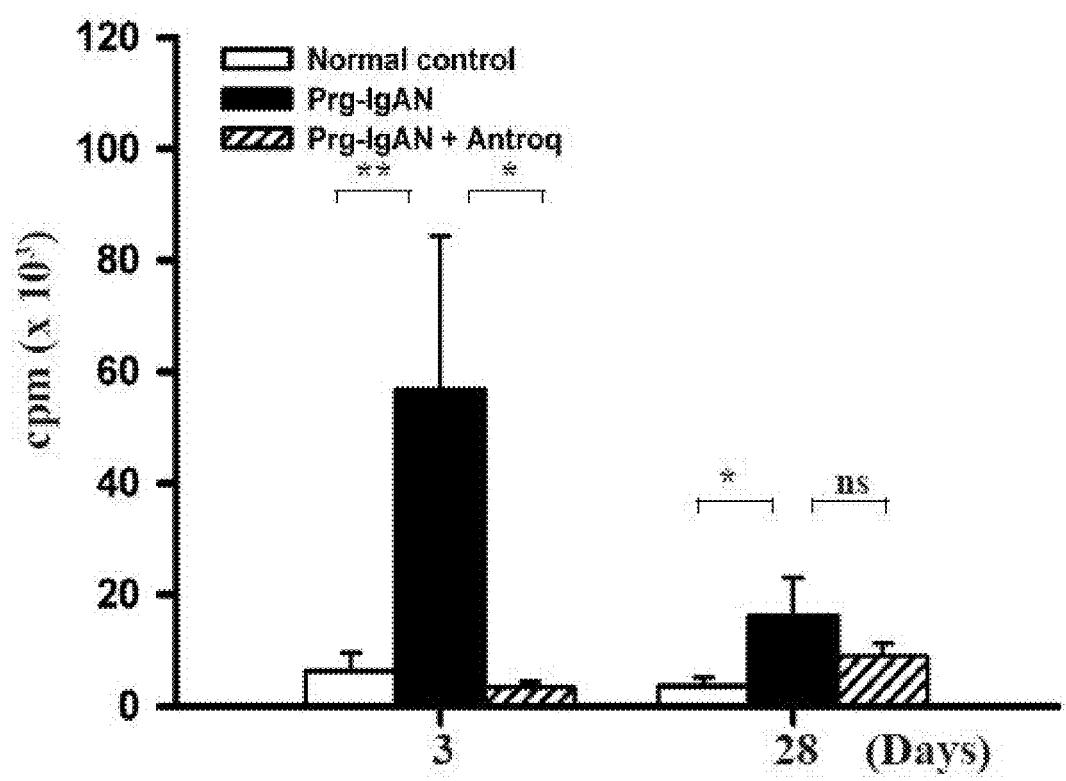
Figure 12C:
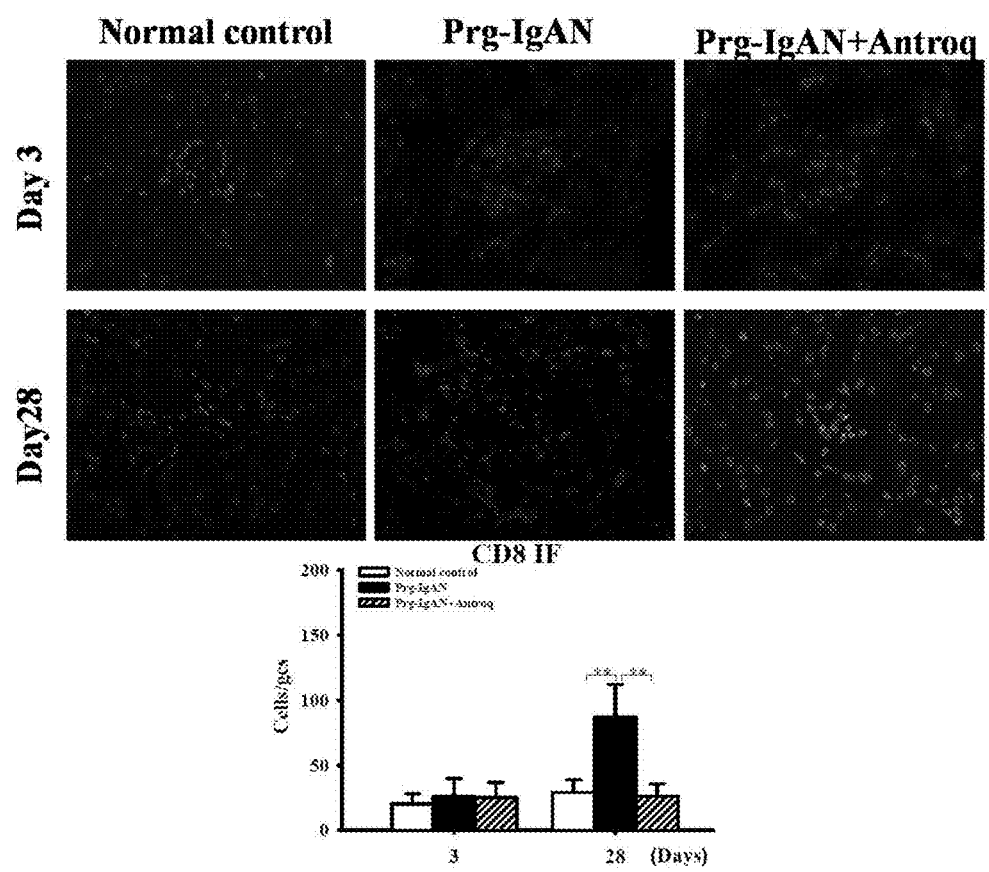
Figure 12D:
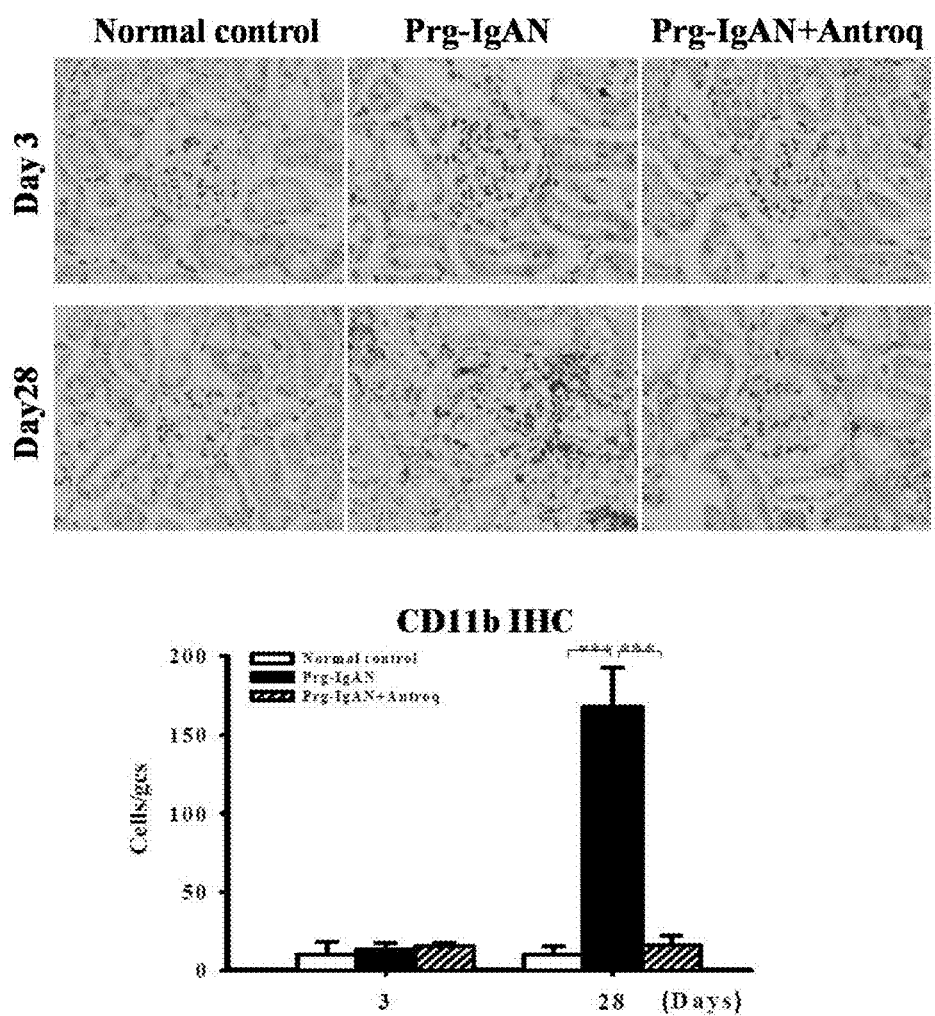
Figure 12E:
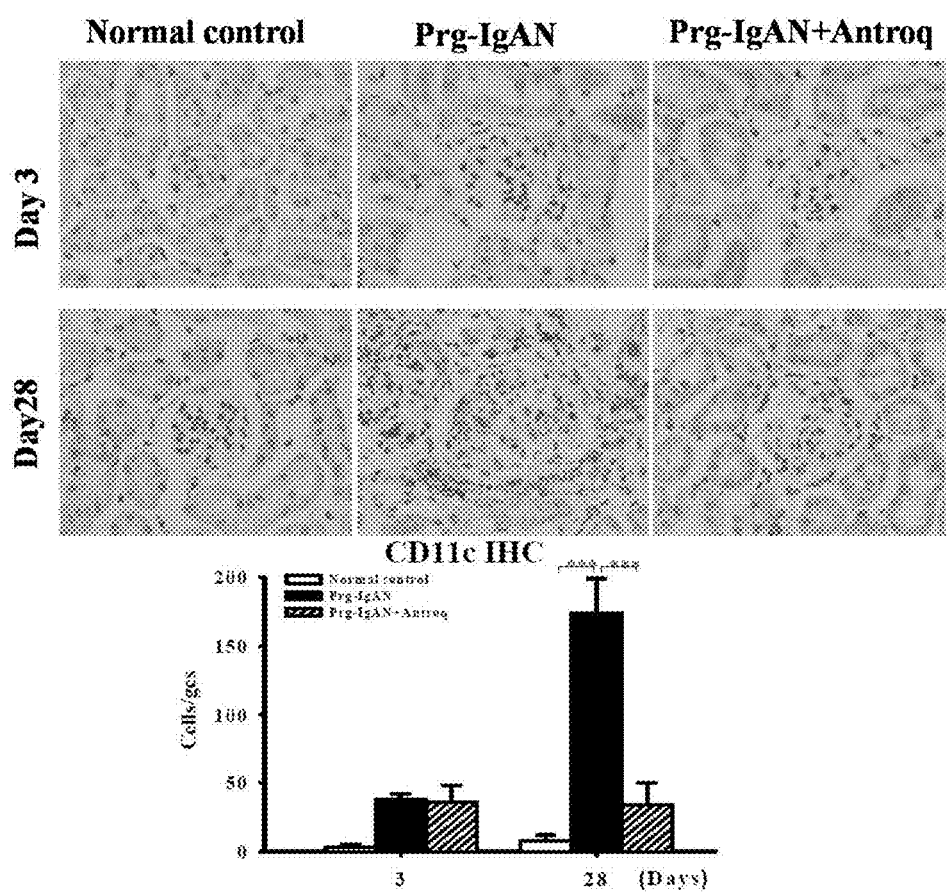
Figure 12F:
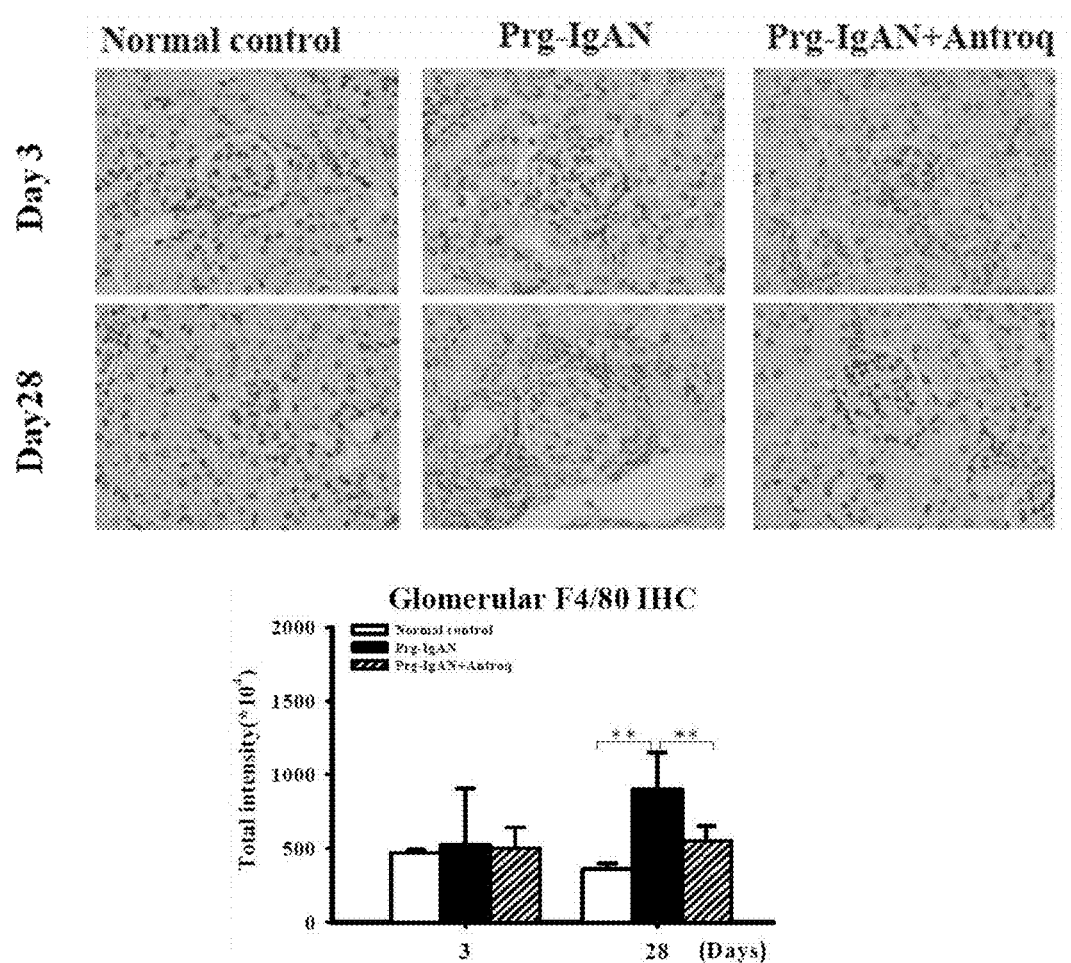

Cell mediated immunity has long been implicated in the pathogenesis of IgAN. Flow cytometry in splenocytes was performed to identify the activation of CD3, CD4 and CD8, respectively. As shown in FIG. 11A-C, an noticeable increase in percentage of $CD3^+/CD69^+$, $CD4^+/CD69^+$ or $CD8^+/CD69^+$ cells was observed in control AcP-IgAN mice at as early as day 3, compared to normal controls, although there was no such effect for all subtypes of T cells later at day 28. In contrast, Compound 1 administration induced a significant reduction in percentage of $CD3^+/CD69^+$ T cells in AcP-IgAN+Antroq mice at day 3, compared to that of control AcP-IgAN mice. There was no significant difference in the percentage of either $CD4^+/CD69^+$ or $CD8^+/CD69^+$ T cells between control AcP-IgAN and AcP-IgAN+Antroq mice at day 3. The percentage of each of all the three subtypes of T cells was no different from that of normal controls at day 28. As demonstrated by thymidine uptake analysis, AcP-IgAN mice revealed a greatly increased proliferation of $CD3^+$ T cell in splenocytes compared to that of AcP-IgAN+Antroq mice early at day 3 (FIGS. 11A-C), and either group of mice showed near baseline levels of proliferation similar to normal controls later at day 28. In parallel, IHC was performed to evaluate the phenotypic expression of mononuclear leukocytes that infiltrated in the kidney of the mice. As shown in FIGS. 12A-F, focal but intense $CD3^+$ (pan-T) cells (FIGS. 12A-C), $CD4^+$ Th cells, $CD8^+$ Tc cells, CD11c+neutrophils, F4/80+monocytes/macrophages, and CD11b+monocytes/macrophages (FIGS. 12D-F) were identified in the renal interstitial tissue, mostly in a peri-glomerular pattern in control AcP-IgAN mice at day 28, compared to normal controls, although only very few inflammatory cells were seen in the kidney at day 3. In contrast, AcP-IgAN+Antroq mice showed significantly decreased infiltration of such inflammatory cells in the kidney, compared to AcP-IgAN mice, at day 28, and there was no detectable signals suggesting infiltration of pan-T cells, neutorphils, and monocytes/macrophages in the kidney of AcP-IgAN+Antroq mice at day 3.

Oxidative Stress, Nrf2 and Related Pathway

ROS has been considered a major detrimental chemical mediator to acceleration and deterioration in various types of renal disorders, including IgAN. The expression levels of ROS were detected systemically in blood and locally in renal tissues. The AcP-IgAN mice showed greatly elevated ROS levels in serum at both day 3 and day 28, and in urine and renal tissues at day 28, compared to normal controls (FIGS. 13A-F). In contrast, the exemplary invention Compound 1 administration caused a substantial reduction in ROS levels in sera at as early as day 3, and in sera, urine and renal tissues of AcP-IgAN+Antroq mice later at day 28, compared to those of control AcP-IgAN mice. In addition, control AcP-IgAN mice showed significantly higher urine nitric oxide (NO) levels than normal controls, at as early as day 3 until day 28. However, AcP-IgAN+Antroq mice showed significantly decreased urine NO levels at both day 3 and day 28, compared to control AcP-IgAN mice. Although there was no significant difference in serum levels of NO at day 3 between control AcP-IgAN and AcP-IgAN+Antroq mice, substantially reduced serum levels of NO were observed at day 28 in AcP-IgAN+Antroq mice, compared to control AcP-IgAN mice.

The potential mechanistic events that might be involved in these findings were further investigated by the administration of an exemplary invention Compound 1. As shown in FIGS. 14A-F, the expression levels of both mRNA and protein of Nrf2 were found greatly increased in AcP-IgAN+Antroq mice, compared to those of control AcP-IgAN mice associated with near normal baseline levels of both mRNA and protein, starting at as early as day 3 until day 28 when the animals were sacrificed. In addition, glutathione peroxidase (GPx), a downstream protein of Nrf2, was found to have significantly higher expression levels in renal tissues of AcP-IgAN+Antroq mice at day 28, compared to control AcP-IgAN mice, while there was no difference at day 3 between the two groups of mice.

Serum Levels of Pro-inflammatory Cytokines

First, as shown in FIG. 15B, serum levels of MCP-1 were significantly elevated at as early as day 3 in control AcP-IgAN mice, and this effect continued to augment until day 28 when the animals were sacrificed. In contrast, this effect was greatly inhibited in AcP-IgAN+Antroq mice, showing only baseline levels. In addition, although there was no difference in serum IL-6 levels between control AcP-IgAN, AcP-IgAN+Antroq and normal control mice at day 3, the AcP-IgAN+Antroq mice showed substantially decreased serum levels of IL-6 at day 28 (FIG. 15A), compared to control AcP-IgAN mice which showed significantly increased serum IL-6 levels compared to normal controls. At day 28, control AcP-IgAN mice showed significantly increased serum levels of IL-10 compared to normal controls, but this effect was greatly inhibited in AcP-IgAN+Antroq mice (FIG. 15C). At day 3, there was no detectable increase in IL-18 levels in both control AcP-IgAN and AcP-IgAN+Antroq mice compared to normal controls (FIG. 15D). At day 28, significantly elevated serum levels of IL-18 were observed in control AcP-IgAN mice, but there was a substantial inhibition in serum IL-18 levels in AcP-IgAN+Antroq mice, although at day 3 both groups of mice had similarly elevated serum IL-18 levels compared to normal controls.

NLRP3 Inflammasome Activation (in the Kidney)

Increasing evidence supports NACHT, LRR and PYD domains-containing protein 3 (NALP3) inflammasome to be an active and crucial player in the innate immune response and link to the adaptive immunity. Although the role of NLRP3 in host response to pathogen associated molecules is well documented, its role in immune complex-mediated glomerular disorders is less studied thus far. Since the development of the AcP-IgAN model in mice involves an enhancement of inflammatory response locally in the kidney, whether NALP3 inflammation activation was operating in the AcP-IgAN mice was determined. At both day 3 and day 28, although greatly increased protein levels of NLRP3 was observed in the kidney of AcP-IgAN mice, compared to normal controls, this effect was significantly inhibited in AcP-IgAN+Antroq mice. mRNA expression levels of NLRP3 in both control AcP-IgAN and AcP-IgAN+Antroq mice were greatly increased at day 3, compared to normal controls, but Compound 1 administration showed no effects on the NLRP3 mRNA expression levels in the AcP-IgAN+Antroq mice. However, at day 28, AcP-IgAN+Antroq mice were found to have substantially reduced renal mRNA levels of NLRP3, compared to control AcP-IgAN mice which still showed greatly higher renal mRNA levels of the gene, compared to normal controls. Importantly, renal mRNA expression levels of both caspase-1 and IL-18 was significantly elevated in AcP-IgAN+Antroq mice at as early as day 3 until later day 28, but these two effects were greatly inhibited in AcP-IgAN+Antroq mice, as demonstrated by quantitative real-time PCR analysis (FIG. 16A-F). In parallel, Antroq administration resulted in a greatly inhibited renal increase in caspase-1 protein levels of AcP-IgAN+Antroq mice, compared to those of control AcP-IgAN mice at both day 3 and day 28, although significantly inhibited renal IL-18 protein production in AcP-IgAN+Antroq mice was observed only at day 28. At day 28, control AcP-IgAN mice revealed a greatly elevated mRNA levels of IL-1beta, but this effect was significantly inhibited in AcP-IgAN+Antroq mice, although there was no detectable increase of renal IL-1beta mRNA expression in all mice at day 3.

Renal NF-κB Activation and its Related Cytokines

Based on the prominent mononuclear leukocytic infiltration in the kidney of AcP-IgAN mice, an active inflammatory response locally in the kidney appeared to be an important pathway in response to the acceleration and progression of IgAN. The role of NF-κB in the kidney was studies and presented herein. First, as shown in FIGS. 17A-F, compared to control AcP-IgAN mice (which showed significantly increased renal levels of nuclear NF-kB protein at day 28 compared to normal controls), AcP-IgAN+Antroq mice exhibited significantly decreased levels of nuclear NF-kB protein in the kidney, although earlier at day 3, there was no detectable increase in renal levels of the protein in both control AcP-IgAN and AcP-IgAN+Antroq mice, compared to normal controls. This effect of Compound 1 was further confirmed by a significantly reduced NF-kB nuclear translocation in AcP-IgAN+Antroq mice, compared to control AcP-IgAN mice (FIGS. 17A and 17B), showing significantly increased nuclear translocation, as demonstrated by IHC of renal tissues at day 28. Next, quantitative analysis of both renal mRNA and protein expression was performed for MCP-1 (FIG. 17C) and IL-6 (FIG. 17D), respectively. The Compound 1 administration significantly reduced the renal expression levels of mRNA and protein of MCP-1 and IL-6 in AcP-IgAN+Antroq mice, compared to control AcP+IgAN mice at day 28, although there was no such effect at day 3 between control AcP-IgAN, AcP-IgAN+Antroq and normal control mice (FIGS. 17E and 17F).

Apoptosis in the Kidney

Apoptosis in the kidney has been implicated in the pathogenesis of IgAN. As shown in FIG. 18A-B, control AcP-IgAN mice showed significantly increased apoptosis in the kidney, as demonstrated by TUNEL, compared to normal controls at day 28, but this effect was greatly inhibited by Antroq administration in AcP-IgAN+Antroq mice, although there was only inconspicuous apoptosis in all the mice examined early at day 3.

Example 15

Parenteral Formulation

To prepare a parenteral pharmaceutical composition suitable for administration by injection, 100 mg of a compound or its salt described herein is dissolved in DMSO and then mixed with 10 mL of 0.9% sterile saline. The mixture is incorporated into a dosage unit form suitable for administration by injection.

Example 16

Oral Formulation

To prepare a pharmaceutical composition for oral delivery, 100 mg of an exemplary Compound 1 was mixed with 100 mg of corn oil. The mixture was incorporated into an oral dosage unit in a capsule, which is suitable for oral administration.

In some instances, 100 mg of a compound described herein is mixed with 750 mg of starch. The mixture is incorporated into an oral dosage unit for, such as a hard gelatin capsule, which is suitable for oral administration.

Example 17

Sublingual (Hard Lozenge) Formulation

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 18

Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 19

Rectal Gel Formulation

To prepare a pharmaceutical composition for rectal delivery, 100 mg of a compound described herein is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 20

Topical Gel Composition

To prepare a pharmaceutical topical gel composition, 100 mg of a compound described herein is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 21

Ophthalmic Solution Composition

To prepare a pharmaceutical ophthalmic solution composition, 100 mg of a compound described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for maintaining IgA nephropathy (IgAN) in remission during the treatment of glomerulonephritis in a subject comprising administering to the subject an effective amount of a cyclohexenone compound having the structure:

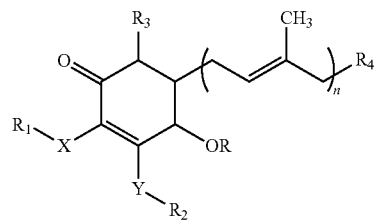

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C_1$-$C_8$ alkyl, $C_2$-$C_8$ alkenyl, $C_2$-$C_8$ alkynyl, $C_3$-$C_8$ cycloalkyl, $C_1$-$C_8$ haloalkyl, and $C_1$-$C_8$ alkoxy;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable solvate thereof.

2. The method of claim 1, said compound attenuating renal dysfunction or glomerular lesions in a subject.

3. The method of claim 1, said compound (a) enhancing renal nuclear factor E2-related factor 2 (Nrf2) activity in a subject; (b) inhibiting renal NF-κB activation and/or transforming growth factor (TGF)-β1 protein expression in a subject; (c) inhibiting ROS/NO and/or p47$^{phox}$ in a subject; (d) reducing CD3$^+$/CD69$^+$ T cells in a subject; (e) reducing pro-inflammatory cytokines in a subject; (f) enhancing glutathione peroxidase (GPx) activity in the kidney; (g) educing renal caspase-1 protein expression and/or inhibiting renal NLRP3 activation in the kidney; (h) reducing renal NF-κB level in the kidney; or (i) inhibiting apoptosis in the kidney.

4. The method of claim 3, wherein the pro-inflammatory cytokines comprise MCP-1, IL-6, IL-1β, IL-18, or combinations thereof.

5. The method of claim 1 wherein said compound (i) blocking renal NLRP3 inflammasome activation and/or (ii) inhibiting the increase in T cell activation in the subject.

6. The method of claim 1, wherein said cyclohexenone compound blocks oxidative stress.

7. The method of claim 6, wherein the oxidative stress is blocked by reducing TGF-β1 and extracellular matrix protein expression.

8. The method of claim 1, wherein the cyclohexenone compound reduces CD3$^+$/CD69$^+$ T cells or pro-inflammatory cytokines in the subject.

9. The method of claim 8, wherein the pro-inflammatory cytokines comprise MCP-1, IL-6, IL-1β, IL-18, or combinations thereof.

10. The method of claim 2, wherein said glomerular lesions comprise epithelial hyperplasia lesion (EPHL).

11. The method of claim 1, wherein said compound is isolated from *Antrodia camphorate*, or prepared synthetically or semi synthetically.

* * * * *